US011241218B2

(12) United States Patent
Emery et al.

(10) Patent No.: US 11,241,218 B2
(45) Date of Patent: Feb. 8, 2022

(54) SYSTEMS AND METHODS FOR COSMETIC ULTRASOUND TREATMENT OF SKIN

(71) Applicant: Ulthera, Inc., Mesa, AZ (US)

(72) Inventors: Charles D. Emery, Gilbert, AZ (US); Stephen John Hsu, Mesa, AZ (US)

(73) Assignee: Ulthera, Inc., Mesa, AZ (US)

( * ) Notice: Subject to any disclaimer, the term of this patent is extended or adjusted under 35 U.S.C. 154(b) by 174 days.

(21) Appl. No.: 15/562,384

(22) PCT Filed: Aug. 14, 2017

(86) PCT No.: PCT/US2017/046703
§ 371 (c)(1),
(2) Date: Sep. 27, 2017

(87) PCT Pub. No.: WO2018/035012
PCT Pub. Date: Feb. 22, 2018

(65) Prior Publication Data
US 2019/0142380 A1    May 16, 2019

Related U.S. Application Data

(60) Provisional application No. 62/375,607, filed on Aug. 16, 2016, provisional application No. 62/482,440, (Continued)

(51) Int. Cl.
*A61B 8/00* (2006.01)
*A61N 7/02* (2006.01)
(Continued)

(52) U.S. Cl.
CPC .............. *A61B 8/4483* (2013.01); *A61B 8/54* (2013.01); *A61N 7/02* (2013.01);
(Continued)

(58) Field of Classification Search
CPC ... A61B 8/4483; A61B 8/54; A61B 2090/378; A61B 8/0858; A61N 7/02;
(Continued)

(56) References Cited

U.S. PATENT DOCUMENTS 2,427,348 A    9/1947   Bond et al.
2,792,829 A    2/1952   Calosi
(Continued)

FOREIGN PATENT DOCUMENTS

CN    2460061    11/2001
CN    1734284    12/2009
(Continued)

OTHER PUBLICATIONS

US 10,398,895 B2, 09/2019, Schwarz (withdrawn)
(Continued)

*Primary Examiner* — Hien N Nguyen
(74) *Attorney, Agent, or Firm* — Knobbe Martens Olson & Bear LLP

(57) ABSTRACT

Embodiments of a dermatological cosmetic treatment and/or imaging system and method adapted for dithering ultrasound beams from a transducer to alter placement and position of one or multiple cosmetic treatment zones in tissue, simultaneous multi-focus therapy using multi-channel signal mixing, and/or dithering ultrasound beams from a transducer to alter placement and position of one or multiple cosmetic treatment zones in tissue, configured for using imaging for improved ultrasound therapy efficacy, and/or adapted for imaging with multiple focal zone sequencing and triggering for mechanically translated and/or steered ultrasound transducers are provided herein. The system can include a hand wand, a removable transducer module, and a control module. In some embodiments, the cosmetic treatment system may be used in various cosmetic procedures.

18 Claims, 29 Drawing Sheets

Related U.S. Application Data filed on Apr. 6, 2017, provisional application No. 62/482,476, filed on Apr. 6, 2017, provisional application No. 62/520,055, filed on Jun. 15, 2017.

(51) Int. Cl.
*A61N 7/00* (2006.01)
*A61B 90/00* (2016.01)

(52) U.S. Cl.
CPC . *A61B 2090/378* (2016.02); *A61N 2007/0008* (2013.01); *A61N 2007/0034* (2013.01); *A61N 2007/0082* (2013.01); *A61N 2007/0091* (2013.01); *A61N 2007/0095* (2013.01)

(58) Field of Classification Search
CPC .... A61N 2007/0095; A61N 2007/0082; A61N 2007/0091; A61N 2007/0034; A61N 2007/0008; A61N 2007/027; A61N 2007/025

See application file for complete search history.

(56) References Cited

U.S. PATENT DOCUMENTS

| | | |
|---|---|---|
| 3,913,386 A | 10/1975 | Saglio |
| 3,965,455 A | 6/1976 | Hurwitz |
| 3,992,925 A | 11/1976 | Perilhou |
| 4,039,312 A | 8/1977 | Patru |
| 4,059,098 A | 11/1977 | Murdock |
| 4,101,795 A | 7/1978 | Fukumoto |
| 4,151,834 A | 5/1979 | Sato et al. |
| 4,166,967 A | 9/1979 | Benes et al. |
| 4,211,948 A | 7/1980 | Smith et al. |
| 4,211,949 A | 7/1980 | Brisken et al. |
| 4,213,344 A | 7/1980 | Rose |
| 4,276,491 A | 6/1981 | Daniel |
| 4,315,514 A | 2/1982 | Drewes et al. |
| 4,325,381 A | 4/1982 | Glenn |
| 4,343,301 A | 8/1982 | Indech |
| 4,372,296 A | 2/1983 | Fahim |
| 4,379,145 A | 4/1983 | Masuho et al. |
| 4,381,007 A | 4/1983 | Doss |
| 4,381,787 A | 5/1983 | Hottinger |
| 4,397,314 A | 8/1983 | Vaguine |
| 4,409,839 A | 10/1983 | Taenzer |
| 4,417,170 A | 11/1983 | Benisncasa |
| 4,431,008 A | 2/1984 | Wanner et al. |
| 4,441,486 A | 4/1984 | Pounds |
| 4,452,084 A | 6/1984 | Taenzer |
| 4,484,569 A | 11/1984 | Driller |
| 4,507,582 A | 3/1985 | Glenn |
| 4,513,749 A | 4/1985 | Kino |
| 4,513,750 A | 4/1985 | Heyman et al. |
| 4,527,550 A | 7/1985 | Ruggera et al. |
| 4,528,979 A | 7/1985 | Marchenko |
| 4,534,221 A | 8/1985 | Fife et al. |
| 4,566,459 A | 1/1986 | Umemura et al. |
| 4,567,895 A | 2/1986 | Putzke |
| 4,586,512 A | 5/1986 | Do-Huu |
| 4,587,971 A | 5/1986 | Stolfi |
| 4,601,296 A | 7/1986 | Yerushalmi |
| 4,620,546 A | 11/1986 | Aida et al. |
| 4,637,256 A | 1/1987 | Sugiyama et al. |
| 4,646,756 A | 3/1987 | Watmough |
| 4,663,358 A | 5/1987 | Hyon |
| 4,668,516 A | 5/1987 | Duraffourd et al. |
| 4,672,591 A | 6/1987 | Breimesser et al. |
| 4,680,499 A | 7/1987 | Umemura et al. |
| 4,697,588 A | 10/1987 | Reichenberger |
| 4,754,760 A | 7/1988 | Fukukita et al. |
| 4,757,820 A | 7/1988 | Itoh |
| 4,771,205 A | 9/1988 | Mequio |
| 4,801,459 A | 1/1989 | Liburdy |
| 4,803,625 A | 2/1989 | Fu et al. |
| 4,807,633 A | 2/1989 | Fry |
| 4,817,615 A | 4/1989 | Fukukita et al. |
| 4,858,613 A | 8/1989 | Fry |
| 4,860,732 A | 8/1989 | Hasegawa et al. |
| 4,865,041 A | 9/1989 | Hassler |
| 4,865,042 A | 9/1989 | Umemura |
| 4,867,169 A | 9/1989 | Machida |
| 4,874,562 A | 10/1989 | Hyon |
| 4,875,487 A | 10/1989 | Seppi |
| 4,881,212 A | 11/1989 | Takeuchi |
| 4,891,043 A | 1/1990 | Zeimer et al. |
| 4,893,624 A | 1/1990 | Lele |
| 4,896,673 A | 1/1990 | Rose |
| 4,900,540 A | 2/1990 | Ryan et al. |
| 4,901,729 A | 2/1990 | Saitoh |
| 4,917,096 A | 4/1990 | Englehart |
| 4,932,414 A | 6/1990 | Coleman et al. |
| 4,938,216 A | 7/1990 | Lele |
| 4,938,217 A | 7/1990 | Lele |
| 4,947,046 A | 8/1990 | Kawabata et al. |
| 4,951,653 A | 8/1990 | Fry |
| 4,955,365 A | 9/1990 | Fry |
| 4,958,626 A | 9/1990 | Nambu |
| 4,976,709 A | 12/1990 | Sand |
| 4,979,501 A | 12/1990 | Valchanov |
| 4,992,989 A | 2/1991 | Watanabe et al. |
| 5,012,797 A | 5/1991 | Liang |
| 5,018,508 A | 5/1991 | Fry et al. |
| 5,030,874 A | 7/1991 | Saito et al. |
| 5,036,855 A | 8/1991 | Fry |
| 5,040,537 A | 8/1991 | Katakura |
| 5,054,310 A | 10/1991 | Flynn |
| 5,054,470 A | 10/1991 | Fry |
| 5,054,491 A | 10/1991 | Saito et al. |
| 5,070,879 A | 12/1991 | Herres |
| 5,088,495 A | 2/1992 | Miyagawa |
| 5,115,814 A | 5/1992 | Griffith |
| 5,117,832 A | 6/1992 | Sanghvi |
| 5,123,418 A | 6/1992 | Saurel |
| 5,142,511 A | 8/1992 | Kanai et al. |
| 5,143,063 A | 9/1992 | Fellner |
| 5,143,074 A | 9/1992 | Dory |
| 5,149,319 A | 9/1992 | Unger |
| 5,150,711 A | 9/1992 | Dory |
| 5,150,714 A | 9/1992 | Green |
| 5,152,294 A | 10/1992 | Mochizuki et al. |
| 5,156,144 A | 10/1992 | Iwasaki |
| 5,158,536 A | 10/1992 | Sekins |
| 5,159,931 A | 11/1992 | Pini |
| 5,163,421 A | 11/1992 | Bernstein |
| 5,163,436 A | 11/1992 | Saitoh et al. |
| 5,178,135 A | 1/1993 | Uchiyama et al. |
| 5,190,518 A | 3/1993 | Takasu |
| 5,190,766 A | 3/1993 | Ishihara |
| 5,191,880 A | 3/1993 | McLeod |
| 5,205,287 A | 4/1993 | Erbel et al. |
| 5,209,720 A | 5/1993 | Unger |
| 5,212,671 A | 5/1993 | Fujii et al. |
| 5,215,680 A | 6/1993 | D'Arrigo |
| 5,224,467 A | 7/1993 | Oku |
| 5,230,334 A | 7/1993 | Klopotek |
| 5,230,338 A | 7/1993 | Allen et al. |
| 5,247,924 A | 9/1993 | Suzuki et al. |
| 5,255,681 A | 10/1993 | Ishimura et al. |
| 5,257,970 A | 11/1993 | Dougherty |
| 5,265,614 A | 11/1993 | Hayakawa |
| 5,267,985 A | 12/1993 | Shimada |
| 5,269,297 A | 12/1993 | Weng |
| 5,282,797 A | 2/1994 | Chess |
| 5,295,484 A | 3/1994 | Marcus |
| 5,295,486 A | 3/1994 | Wollschlager et al. |
| 5,304,169 A | 4/1994 | Sand |
| 5,305,756 A | 4/1994 | Entrekin et al. |
| 5,321,520 A | 6/1994 | Inga et al. |
| 5,323,779 A | 6/1994 | Hardy et al. |
| 5,327,895 A | 7/1994 | Hashimoto et al. |
| 5,329,202 A | 7/1994 | Garlick et al. |
| 5,348,016 A | 9/1994 | Unger et al. |
| 5,358,466 A | 10/1994 | Aida et al. |

(56) References Cited

U.S. PATENT DOCUMENTS

| | | |
|---|---|---|
| 5,360,268 A | 11/1994 | Hayashi |
| 5,370,121 A | 12/1994 | Reichenberger |
| 5,370,122 A | 12/1994 | Kunig |
| 5,371,483 A | 12/1994 | Bhardwaj |
| 5,375,602 A | 12/1994 | Lancee et al. |
| 5,379,773 A | 1/1995 | Hornsby |
| 5,380,280 A | 1/1995 | Peterson |
| 5,380,519 A | 1/1995 | Schneider et al. |
| 5,383,917 A | 1/1995 | Desai et al. |
| 5,391,140 A | 2/1995 | Schaetzle et al. |
| 5,391,197 A | 2/1995 | Burdette et al. |
| 5,392,259 A | 2/1995 | Bolorforosh |
| 5,396,143 A | 3/1995 | Seyed-Bolorforosh et al. |
| 5,398,689 A | 3/1995 | Connor et al. |
| 5,406,503 A | 4/1995 | Williams |
| 5,413,550 A | 5/1995 | Castel |
| 5,417,216 A | 5/1995 | Tanaka |
| 5,423,220 A | 6/1995 | Finsterwald et al. |
| 5,435,311 A | 7/1995 | Umemura |
| 5,438,998 A | 8/1995 | Hanafy |
| 5,443,068 A | 8/1995 | Cline et al. |
| 5,445,611 A | 8/1995 | Eppstein et al. |
| 5,458,596 A | 10/1995 | Lax |
| 5,460,179 A | 10/1995 | Okunuki et al. |
| 5,460,595 A | 10/1995 | Hall et al. |
| 5,419,327 A | 11/1995 | Rohwedder |
| 5,469,854 A | 11/1995 | Unger et al. |
| 5,471,488 A | 12/1995 | Fujio |
| 5,472,405 A | 12/1995 | Buchholtz et al. |
| 5,487,388 A | 1/1996 | Rello et al. |
| 5,492,126 A | 2/1996 | Hennige |
| 5,496,256 A | 3/1996 | Bock |
| 5,501,655 A | 3/1996 | Rolt |
| 5,503,152 A | 4/1996 | Oakley et al. |
| 5,503,320 A | 4/1996 | Webster et al. |
| 5,507,790 A | 4/1996 | Weiss |
| 5,511,296 A | 4/1996 | Dias et al. |
| 5,520,188 A | 5/1996 | Hennige |
| 5,522,869 A | 6/1996 | Burdette |
| 5,523,058 A | 6/1996 | Umemura et al. |
| 5,524,620 A | 6/1996 | Rosenchein |
| 5,524,624 A | 6/1996 | Tepper |
| 5,524,625 A | 6/1996 | Okazaki |
| 5,526,624 A | 6/1996 | Berg |
| 5,526,812 A | 6/1996 | Dumoulin et al. |
| 5,526,814 A | 6/1996 | Cline et al. |
| 5,526,815 A | 6/1996 | Granz |
| 5,529,070 A | 6/1996 | Augustine et al. |
| 5,540,235 A | 7/1996 | Wilson |
| 5,558,092 A | 9/1996 | Unger |
| 5,560,362 A | 10/1996 | Sliwa et al. |
| 5,573,497 A | 11/1996 | Chapelon |
| 5,575,291 A | 11/1996 | Hayakawa |
| 5,575,807 A | 11/1996 | Faller |
| 5,577,502 A | 11/1996 | Darrow et al. |
| 5,577,507 A | 11/1996 | Snyder et al. |
| 5,577,991 A | 11/1996 | Akui et al. |
| 5,580,575 A | 12/1996 | Unger et al. |
| 5,643,179 A | 1/1997 | Fujimoto |
| 5,601,526 A | 2/1997 | Chapelon |
| 5,603,323 A | 2/1997 | Pflugrath et al. |
| 5,605,154 A | 2/1997 | Ries et al. |
| 5,609,562 A | 3/1997 | Kaali |
| 5,615,091 A | 3/1997 | Palatnik |
| 5,618,275 A | 4/1997 | Bock |
| 5,620,479 A | 4/1997 | Diederich |
| 5,622,175 A | 4/1997 | Sudol et al. |
| 5,617,858 A | 5/1997 | Taverna et al. |
| 5,638,819 A | 6/1997 | Manwaring et al. |
| 5,644,085 A | 7/1997 | Lorraine et al. |
| 5,647,373 A | 7/1997 | Paltieli |
| 5,655,535 A | 8/1997 | Frlemel et al. |
| 5,655,538 A | 8/1997 | Lorraine |
| 5,657,760 A | 8/1997 | Ying |
| 5,658,328 A | 8/1997 | Johnson |
| 5,660,836 A | 8/1997 | Knowlton |
| 5,662,116 A | 9/1997 | Kondo |
| 5,665,053 A | 9/1997 | Jacobs |
| 5,665,141 A | 9/1997 | Vago |
| 5,671,746 A | 9/1997 | Dreschel et al. |
| 5,673,699 A | 10/1997 | Trahey et al. |
| 5,676,692 A | 10/1997 | Sanghvi |
| 5,677,491 A * | 10/1997 | Ishrak ............... A61B 8/4483 310/335 |
| 5,685,820 A | 11/1997 | Riek et al. |
| 5,690,608 A | 11/1997 | Watanabe |
| 5,694,936 A | 12/1997 | Fujimoto |
| 5,697,897 A | 12/1997 | Buchholtz |
| 5,701,900 A | 12/1997 | Shehada et al. |
| 5,704,361 A | 1/1998 | Seward et al. |
| 5,706,252 A | 1/1998 | Le Verrier et al. |
| 5,706,564 A | 1/1998 | Rhyne |
| 5,715,823 A | 2/1998 | Wood et al. |
| 5,720,287 A | 2/1998 | Chapelon et al. |
| 5,722,411 A | 3/1998 | Suzuki |
| 5,727,554 A | 3/1998 | Kalend et al. |
| 5,735,280 A | 4/1998 | Sherman et al. |
| 5,740,804 A | 4/1998 | Cerofolini |
| 5,743,863 A | 4/1998 | Chapelon |
| 5,746,005 A | 5/1998 | Steinberg |
| 5,746,762 A | 5/1998 | Bass |
| 5,748,767 A | 5/1998 | Raab |
| 5,749,364 A | 5/1998 | Sliwa et al. |
| 5,755,228 A | 5/1998 | Wilson et al. |
| 5,755,753 A | 5/1998 | Knowlton |
| 5,762,066 A | 6/1998 | Law |
| 5,763,886 A | 6/1998 | Schulte |
| 5,769,790 A | 6/1998 | Watkins |
| 5,779,644 A | 7/1998 | Eberle et al. |
| 5,792,058 A | 8/1998 | Lee |
| 5,795,297 A | 8/1998 | Daigle |
| 5,795,311 A | 8/1998 | Wess |
| 5,810,009 A | 9/1998 | Mine et al. |
| 5,810,888 A | 9/1998 | Fenn |
| 5,814,599 A | 9/1998 | Mitragotri et al. |
| 5,817,013 A | 10/1998 | Ginn et al. |
| 5,817,021 A | 10/1998 | Reichenberger |
| 5,820,564 A | 10/1998 | Slayton |
| 5,823,962 A | 10/1998 | Schaetzle |
| 5,827,204 A | 10/1998 | Grandia et al. |
| 5,840,032 A | 11/1998 | Hatfield et al. |
| 5,844,140 A | 12/1998 | Seale |
| 5,853,367 A | 12/1998 | Chalek et al. |
| 5,866,024 A | 2/1999 | de Villeneuve |
| 5,869,751 A | 2/1999 | Bonin |
| 5,871,524 A | 2/1999 | Knowlton |
| 5,873,902 A | 2/1999 | Sanghvi |
| 5,876,341 A | 3/1999 | Wang et al. |
| 5,879,303 A | 3/1999 | Averkiou et al. |
| 5,882,557 A | 3/1999 | Hayakawa |
| 5,891,034 A | 4/1999 | Bucholz |
| 5,895,356 A | 4/1999 | Andrus et al. |
| 5,899,861 A | 5/1999 | Friemel et al. |
| 5,904,659 A | 5/1999 | Duarte |
| 5,919,219 A | 7/1999 | Knowlton |
| 5,923,099 A | 7/1999 | Bilir |
| 5,924,989 A | 7/1999 | Polz |
| 5,928,169 A | 7/1999 | Schatzle et al. |
| 5,931,805 A | 8/1999 | Brisken |
| 5,938,606 A | 8/1999 | Bonnefous |
| 5,938,612 A | 8/1999 | Kline-Schoder |
| 5,948,011 A | 9/1999 | Knowlton |
| 5,957,844 A | 9/1999 | Dekel |
| 5,957,882 A | 9/1999 | Nita et al. |
| 5,957,941 A | 9/1999 | Ream |
| 5,964,707 A | 10/1999 | Fenster et al. |
| 5,967,980 A | 10/1999 | Ferre et al. |
| 5,968,034 A | 10/1999 | Fullmer |
| 5,971,949 A | 10/1999 | Levin |
| 5,977,538 A | 11/1999 | Unger et al. |
| 5,984,881 A | 11/1999 | Ishibashi et al. |
| 5,984,882 A | 11/1999 | Rosenchein |
| 5,990,598 A | 11/1999 | Sudol et al. |
| 5,997,471 A | 12/1999 | Gumb et al. |

(56) References Cited

U.S. PATENT DOCUMENTS

| | | |
|---|---|---|
| 5,997,497 A | 12/1999 | Nita et al. |
| 5,999,843 A | 12/1999 | Anbar |
| 6,004,262 A | 12/1999 | Putz et al. |
| 6,007,499 A | 12/1999 | Martin et al. |
| 6,013,032 A | 1/2000 | Savord |
| 6,014,473 A | 1/2000 | Hossack et al. |
| 6,016,255 A | 1/2000 | Bolan et al. |
| 6,019,724 A | 2/2000 | Gronningsaeter et al. |
| 6,022,308 A | 2/2000 | Williams |
| 6,022,317 A | 2/2000 | Cruanas et al. |
| 6,022,327 A | 2/2000 | Chang |
| 6,030,374 A | 2/2000 | McDaniel |
| 6,036,646 A | 3/2000 | Barthe |
| 6,039,048 A | 3/2000 | Silberg |
| 6,039,689 A | 3/2000 | Lizzi |
| 6,042,556 A | 3/2000 | Beach |
| 6,049,159 A | 4/2000 | Barthe |
| 6,050,943 A | 4/2000 | Slayton |
| 6,059,727 A | 5/2000 | Fowlkes |
| 6,071,239 A | 6/2000 | Cribbs |
| 6,080,108 A | 6/2000 | Dunham |
| 6,083,148 A | 7/2000 | Williams |
| 6,086,535 A | 7/2000 | Ishibashi |
| 6,086,580 A | 7/2000 | Mordon et al. |
| 6,090,054 A | 7/2000 | Tagishi |
| 6,093,148 A | 7/2000 | Fujimoto |
| 6,093,883 A | 7/2000 | Sanghvi |
| 6,100,626 A | 8/2000 | Frey et al. |
| 6,101,407 A | 8/2000 | Groezinger |
| 6,106,469 A | 8/2000 | Suzuki et al. |
| 6,113,558 A | 9/2000 | Rosenchein |
| 6,113,559 A | 9/2000 | Klopotek |
| 6,120,452 A | 9/2000 | Barthe |
| 6,123,081 A | 9/2000 | Durette |
| 6,126,619 A | 10/2000 | Peterson et al. |
| 6,135,971 A | 10/2000 | Hutchinson |
| 6,139,499 A | 10/2000 | Wilk |
| 6,159,150 A | 12/2000 | Yale et al. |
| 6,171,244 B1 | 1/2001 | Finger et al. |
| 6,176,840 B1 | 1/2001 | Nishimura |
| 6,183,426 B1 | 2/2001 | Akisada |
| 6,183,502 B1 | 2/2001 | Takeuchi |
| 6,183,773 B1 | 2/2001 | Anderson |
| 6,190,323 B1 | 2/2001 | Dias |
| 6,190,336 B1 | 2/2001 | Duarte |
| 6,193,658 B1 | 2/2001 | Wendelken |
| 6,198,956 B1 | 3/2001 | Dunne |
| 6,210,327 B1 | 4/2001 | Brackett et al. |
| 6,213,948 B1 | 4/2001 | Barthe |
| 6,216,029 B1 | 4/2001 | Paltieli |
| 6,233,476 B1 | 5/2001 | Strommer et al. |
| 6,234,990 B1 | 5/2001 | Rowe et al. |
| 6,241,753 B1 * | 6/2001 | Knowlton ............... A61B 18/12 128/898 |
| 6,246,898 B1 | 6/2001 | Vesely et al. |
| 6,251,074 B1 | 6/2001 | Averkiou et al. |
| 6,251,088 B1 | 6/2001 | Kaufman et al. |
| 6,268,405 B1 | 7/2001 | Yao |
| 6,273,864 B1 | 8/2001 | Duarte |
| 6,280,402 B1 | 8/2001 | Ishibashi et al. |
| 6,287,257 B1 | 9/2001 | Matichuk |
| 6,287,304 B1 | 9/2001 | Eggers et al. |
| 6,296,619 B1 | 10/2001 | Brisken |
| 6,301,989 B1 | 10/2001 | Brown et al. |
| 6,307,302 B1 | 10/2001 | Toda |
| 6,309,355 B1 | 10/2001 | Cain et al. |
| 6,311,090 B1 | 10/2001 | Knowlton |
| 6,315,741 B1 | 11/2001 | Martin |
| 6,322,509 B1 | 11/2001 | Pan et al. |
| 6,322,532 B1 | 11/2001 | D'Sa |
| 6,325,540 B1 | 12/2001 | Lounsberry et al. |
| 6,325,758 B1 | 12/2001 | Carol et al. |
| 6,325,769 B1 | 12/2001 | Klopotek |
| 6,325,798 B1 | 12/2001 | Edwards et al. |
| 6,338,716 B1 | 1/2002 | Hossack et al. |
| 6,350,276 B1 | 2/2002 | Knowlton |
| 6,356,780 B1 | 3/2002 | Licato et al. |
| 6,361,531 B1 | 3/2002 | Hissong |
| 6,370,411 B1 | 4/2002 | Osadchy et al. |
| 6,375,672 B1 | 4/2002 | Aksan |
| 6,377,854 B1 | 4/2002 | Knowlton |
| 6,377,855 B1 | 4/2002 | Knowlton |
| 6,381,497 B1 | 4/2002 | Knowlton |
| 6,381,498 B1 | 4/2002 | Knowlton |
| 6,387,380 B1 | 5/2002 | Knowlton |
| 6,390,982 B1 | 5/2002 | Bova et al. |
| 6,405,090 B1 | 6/2002 | Knowlton |
| 6,409,720 B1 | 6/2002 | Hissong |
| 6,413,216 B1 | 7/2002 | Cain et al. |
| 6,413,253 B1 | 7/2002 | Koop |
| 6,413,254 B1 | 7/2002 | Hissong |
| 6,419,648 B1 | 7/2002 | Vitek |
| 6,423,007 B2 | 7/2002 | Lizzi et al. |
| 6,425,865 B1 | 7/2002 | Salcudean |
| 6,425,867 B1 | 7/2002 | Vaezy |
| 6,425,912 B1 | 7/2002 | Knowlton |
| 6,428,477 B1 | 8/2002 | Mason |
| 6,428,532 B1 | 8/2002 | Doukas |
| 6,430,446 B1 | 8/2002 | Knowlton |
| 6,432,057 B1 | 8/2002 | Mazess et al. |
| 6,432,067 B1 | 8/2002 | Martin |
| 6,432,101 B1 | 8/2002 | Weber |
| 6,436,061 B1 | 8/2002 | Costantino |
| 6,438,424 B1 | 8/2002 | Knowlton |
| 6,440,071 B1 | 8/2002 | Slayton |
| 6,440,121 B1 | 8/2002 | Weber |
| 6,443,914 B1 | 9/2002 | Costantino |
| 6,447,443 B1 | 9/2002 | Keogh et al. |
| 6,450,979 B1 | 9/2002 | Miwa et al. |
| 6,451,013 B1 | 9/2002 | Bays et al. |
| 6,453,202 B1 | 9/2002 | Knowlton |
| 6,461,304 B1 | 10/2002 | Tanaka et al. |
| 6,461,378 B1 | 10/2002 | Knowlton |
| 6,470,216 B1 | 10/2002 | Knowlton |
| 6,485,420 B1 | 11/2002 | Bullis |
| 6,488,626 B1 | 12/2002 | Lizzi |
| 6,491,657 B2 | 12/2002 | Rowe |
| 6,500,121 B1 | 12/2002 | Slayton |
| 6,500,141 B1 | 12/2002 | Irion |
| 6,506,171 B1 | 1/2003 | Vitek et al. |
| 6,508,774 B1 | 1/2003 | Acker |
| 6,511,427 B1 | 1/2003 | Sliwa, Jr. et al. |
| 6,511,428 B1 | 1/2003 | Azuma |
| 6,514,244 B2 | 2/2003 | Pope |
| 6,517,484 B1 | 2/2003 | Wilk |
| 6,524,250 B1 | 2/2003 | Weber |
| 6,666,835 B2 | 3/2003 | Martin |
| 6,540,679 B2 | 4/2003 | Slayton |
| 6,540,685 B1 | 4/2003 | Rhoads et al. |
| 6,540,700 B1 | 4/2003 | Fujimoto et al. |
| 6,547,788 B1 | 4/2003 | Maguire et al. |
| 6,554,771 B1 | 4/2003 | Buil et al. |
| 6,569,099 B1 | 5/2003 | Babaev |
| 6,569,108 B2 | 5/2003 | Sarvazyan et al. |
| 6,572,552 B2 | 6/2003 | Fukukita |
| 6,575,956 B1 | 6/2003 | Brisken et al. |
| 6,595,934 B1 | 7/2003 | Hissong |
| 6,599,256 B1 | 7/2003 | Acker |
| 6,605,043 B1 | 8/2003 | Dreschel |
| 6,605,080 B1 | 8/2003 | Altshuler et al. |
| 6,607,498 B2 | 8/2003 | Eshel |
| 6,618,620 B1 | 9/2003 | Freundlich et al. |
| 6,623,430 B1 | 9/2003 | Slayton |
| 6,626,854 B2 | 9/2003 | Friedman |
| 6,626,855 B1 | 9/2003 | Weng |
| 6,638,226 B2 | 10/2003 | He et al. |
| 6,645,145 B1 | 11/2003 | Dreschel et al. |
| 6,645,150 B2 | 11/2003 | Angelsen et al. |
| 6,645,162 B2 | 11/2003 | Friedman |
| 6,662,054 B2 | 12/2003 | Kreindel |
| 6,663,627 B2 | 12/2003 | Francischelli |
| 6,665,806 B1 | 12/2003 | Shimizu |
| 6,669,638 B1 | 12/2003 | Miller |
| 6,685,639 B1 | 2/2004 | Wang et al. |

(56) References Cited

U.S. PATENT DOCUMENTS

| | | |
|---|---|---|
| 6,685,640 B1 | 2/2004 | Fry |
| 6,692,450 B1 | 2/2004 | Coleman |
| 6,699,237 B2 | 3/2004 | Weber |
| 6,716,184 B2 | 4/2004 | Vaezy et al. |
| 6,719,449 B1 | 4/2004 | Laughlin |
| 6,719,694 B2 | 4/2004 | Weng |
| 6,726,627 B1 | 4/2004 | Lizzi et al. |
| 6,733,449 B1 | 5/2004 | Krishnamurthy et al. |
| 6,749,624 B2 | 6/2004 | Knowlton |
| 6,772,490 B2 | 8/2004 | Toda |
| 6,773,409 B2 | 8/2004 | Truckai et al. |
| 6,775,404 B1 | 8/2004 | Pagoulatos et al. |
| 6,790,187 B2 | 9/2004 | Thompson et al. |
| 6,824,516 B2 | 11/2004 | Batten et al. |
| 6,825,176 B2 | 11/2004 | White et al. |
| 6,835,940 B2 | 12/2004 | Morikawa et al. |
| 6,846,290 B2 | 1/2005 | Lizzi et al. |
| 6,875,176 B2 | 4/2005 | Mourad et al. |
| 6,882,884 B1 | 4/2005 | Mosk et al. |
| 6,887,239 B2 | 5/2005 | Elstrom |
| 6,887,260 B1 | 5/2005 | McDaniel |
| 6,889,089 B2 | 5/2005 | Behl |
| 6,896,657 B2 | 5/2005 | Willis |
| 6,902,536 B2 | 6/2005 | Manna |
| 6,905,466 B2 | 6/2005 | Salgo |
| 6,918,907 B2 | 7/2005 | Kelly |
| 6,920,883 B2 | 7/2005 | Bessette |
| 6,921,371 B2 | 7/2005 | Wilson |
| 6,932,771 B2 | 8/2005 | Whitmore |
| 6,932,814 B2 | 8/2005 | Wood |
| 6,936,044 B2 | 8/2005 | McDaniel |
| 6,936,046 B2 | 8/2005 | Hissong |
| 6,945,937 B2 | 9/2005 | Culp et al. |
| 6,948,843 B2 | 9/2005 | Laugharn et al. |
| 6,953,941 B2 | 10/2005 | Nakano et al. |
| 6,958,043 B2 | 10/2005 | Hissong |
| 6,971,994 B1 | 12/2005 | Young et al. |
| 6,974,417 B2 | 12/2005 | Lockwood |
| 6,976,492 B2 | 12/2005 | Ingle |
| 6,992,305 B2 | 1/2006 | Maezawa et al. |
| 6,997,923 B2 | 2/2006 | Anderson |
| 7,006,874 B2 | 2/2006 | Knowlton |
| 7,020,528 B2 | 3/2006 | Neev |
| 7,022,089 B2 | 4/2006 | Ooba |
| 7,058,440 B2 | 6/2006 | Heuscher et al. |
| 7,063,666 B2 | 6/2006 | Weng |
| 7,070,565 B2 | 7/2006 | Vaezy et al. |
| 7,074,218 B2 | 7/2006 | Washington et al. |
| 7,094,252 B2 | 8/2006 | Koop |
| 7,108,663 B2 | 9/2006 | Talish et al. |
| 7,115,123 B2 | 10/2006 | Knowlton |
| 7,122,029 B2 | 10/2006 | Koop et al. |
| 7,142,905 B2 | 11/2006 | Slayton |
| 7,165,451 B1 | 1/2007 | Brooks et al. |
| 7,179,238 B2 | 2/2007 | Hissong |
| 7,189,230 B2 | 3/2007 | Knowlton |
| 7,229,411 B2 | 6/2007 | Slayton |
| 7,235,592 B2 | 6/2007 | Muratoglu |
| 7,258,674 B2 | 8/2007 | Cribbs |
| 7,273,459 B2 | 9/2007 | Desilets |
| 7,294,125 B2 | 11/2007 | Phalen et al. |
| 7,297,117 B2 | 11/2007 | Trucco |
| 7,303,555 B2 | 12/2007 | Makin et al. |
| 7,311,679 B2 | 12/2007 | Desilets et al. |
| 7,327,071 B2 | 2/2008 | Nishiyama et al. |
| 7,331,951 B2 | 2/2008 | Eshel et al. |
| 7,332,985 B2 | 2/2008 | Larson et al. |
| 7,338,434 B1 | 3/2008 | Haarstad et al. |
| 7,347,855 B2 | 3/2008 | Eshel |
| RE40,403 E | 6/2008 | Cho et al. |
| 7,393,325 B2 | 7/2008 | Barthe |
| 7,398,116 B2 | 7/2008 | Edwards |
| 7,399,279 B2 | 7/2008 | Abend et al. |
| 7,491,171 B2 | 2/2009 | Barthe et al. |
| 7,507,235 B2 | 3/2009 | Keogh et al. |
| 7,510,536 B2 | 3/2009 | Foley et al. |
| 7,517,315 B2 | 4/2009 | Willis |
| 7,530,356 B2 | 5/2009 | Slayton |
| 7,530,958 B2 | 5/2009 | Slayton |
| 7,532,201 B2 | 5/2009 | Quistgaard et al. |
| 7,571,336 B2 | 8/2009 | Barthe |
| 7,601,120 B2 | 10/2009 | Moilanen et al. |
| 7,615,015 B2 | 11/2009 | Coleman |
| 7,615,016 B2 | 11/2009 | Barthe |
| 7,652,411 B2 | 1/2010 | Crunkilton et al. |
| 7,662,114 B2 | 2/2010 | Seip et al. |
| 7,674,257 B2 | 3/2010 | Pless et al. |
| 7,686,763 B2 | 3/2010 | Vaezy et al. |
| 7,713,203 B2 | 3/2010 | Lacoste et al. |
| 7,694,406 B2 | 4/2010 | Wildes et al. |
| 7,695,437 B2 | 4/2010 | Quistgaard et al. |
| 7,727,156 B2 | 6/2010 | Angelsen et al. |
| 7,758,524 B2 | 7/2010 | Barthe |
| 7,766,848 B2 | 8/2010 | Desilets et al. |
| 7,789,841 B2 | 9/2010 | Huckle et al. |
| 7,806,839 B2 | 10/2010 | Mast et al. |
| 7,815,570 B2 | 10/2010 | Eshel et al. |
| 7,819,826 B2 | 10/2010 | Diederich et al. |
| 7,828,734 B2 | 10/2010 | Azhari et al. |
| 7,824,348 B2 | 11/2010 | Barthe |
| 7,833,162 B2 | 11/2010 | Hasegawa et al. |
| 7,841,984 B2 | 11/2010 | Cribbs et al. |
| 7,846,096 B2 | 12/2010 | Mast et al. |
| 7,857,773 B2 | 12/2010 | Desilets et al. |
| 7,875,023 B2 | 1/2011 | Eshel et al. |
| 7,901,359 B2 | 3/2011 | Mandrusov et al. |
| 7,905,007 B2 | 3/2011 | Calisti et al. |
| 7,905,844 B2 | 3/2011 | Desilets et al. |
| 7,914,453 B2 | 3/2011 | Slayton et al. |
| 7,914,469 B2 | 3/2011 | Torbati |
| 7,955,281 B2 | 6/2011 | Pedersen et al. |
| 7,967,764 B2 | 6/2011 | Lidgren et al. |
| 7,967,839 B2 | 6/2011 | Flock et al. |
| 7,955,262 B2 | 7/2011 | Rosenberg |
| 7,993,289 B2 | 8/2011 | Quistgaard et al. |
| 8,057,465 B2 | 9/2011 | Sliwa, Jr. et al. |
| 8,057,389 B2 | 11/2011 | Barthe et al. |
| 8,066,641 B2 | 11/2011 | Barthe et al. |
| 8,123,707 B2 | 2/2012 | Huckle et al. |
| 8,128,618 B2 | 3/2012 | Gliklich et al. |
| 8,133,180 B2 | 3/2012 | Slayton et al. |
| 8,133,191 B2 | 3/2012 | Rosenberg et al. |
| 8,142,200 B2 | 3/2012 | Crunkilton et al. |
| 8,152,904 B2 | 4/2012 | Slobodzian et al. |
| 8,162,858 B2 | 4/2012 | Manna et al. |
| 8,166,332 B2 | 4/2012 | Barthe et al. |
| 8,182,428 B2 | 5/2012 | Angelsen et al. |
| 8,197,409 B2 | 6/2012 | Foley et al. |
| 8,206,299 B2 | 6/2012 | Foley et al. |
| 8,208,346 B2 | 6/2012 | Crunkilton |
| 8,211,017 B2 | 7/2012 | Foley et al. |
| 8,262,591 B2 | 9/2012 | Pedersen et al. |
| 8,262,650 B2 | 9/2012 | Zanelli et al. |
| 8,264,126 B2 | 9/2012 | Toda et al. |
| 8,273,037 B2 | 9/2012 | Kreindel et al. |
| 8,282,554 B2 | 10/2012 | Makin et al. |
| 8,292,835 B1 | 10/2012 | Cimino |
| 8,298,163 B1 | 10/2012 | Cimino |
| 8,333,700 B1 | 12/2012 | Barthe et al. |
| 8,334,637 B2 | 12/2012 | Crunkilton et al. |
| 8,337,407 B2 | 12/2012 | Quistgaard et al. |
| 8,343,051 B2 | 1/2013 | Desilets et al. |
| 8,454,540 B2 | 1/2013 | Eshel et al. |
| 8,366,622 B2 | 2/2013 | Slayton et al. |
| 8,398,549 B2 | 3/2013 | Palmeri et al. |
| 8,409,097 B2 | 4/2013 | Slayton et al. |
| 8,425,435 B2 | 4/2013 | Wing et al. |
| 8,388,535 B2 | 5/2013 | Weng et al. |
| 8,444,562 B2 | 5/2013 | Barthe et al. |
| 8,460,193 B2 | 6/2013 | Barthe et al. |
| 8,480,585 B2 | 7/2013 | Slayton et al. |
| 8,486,001 B2 | 7/2013 | Weyant |
| 8,506,486 B2 | 8/2013 | Slayton et al. |
| 8,512,250 B2 | 8/2013 | Quistgaard et al. |

(56) References Cited

U.S. PATENT DOCUMENTS

| | | |
|---|---|---|
| 8,523,775 B2 | 9/2013 | Barthe et al. |
| 8,523,849 B2 | 9/2013 | Liu et al. |
| 8,535,228 B2 | 9/2013 | Slayton et al. |
| 8,570,837 B2 | 10/2013 | Toda et al. |
| 8,573,392 B2 | 11/2013 | Bennett et al. |
| 8,583,211 B2 | 11/2013 | Salomir et al. |
| 8,585,618 B2 | 11/2013 | Hunziker et al. |
| 8,604,672 B2 | 12/2013 | Toda et al. |
| 8,622,937 B2 | 1/2014 | Weng et al. |
| 8,636,665 B2 | 1/2014 | Slayton et al. |
| 8,641,622 B2 | 2/2014 | Barthe et al. |
| 8,663,112 B2 | 3/2014 | Slayton et al. |
| 8,672,848 B2 | 3/2014 | Slayton et al. |
| 8,690,778 B2 | 4/2014 | Slayton et al. |
| 8,690,779 B2 | 4/2014 | Slayton et al. |
| 8,690,780 B2 | 4/2014 | Slayton et al. |
| 8,708,935 B2 | 4/2014 | Barthe et al. |
| 8,715,186 B2 | 5/2014 | Slayton et al. |
| 8,726,781 B2 | 5/2014 | Eckhoff et al. |
| 8,728,071 B2 | 5/2014 | Lischinsky et al. |
| 8,753,295 B2 | 6/2014 | Thierman |
| 8,758,253 B2 | 6/2014 | Sano et al. |
| 8,836,203 B2 | 9/2014 | Nobles et al. |
| 8,857,438 B2 | 10/2014 | Barthe et al. |
| 8,858,471 B2 | 10/2014 | Barthe et al. |
| 8,915,853 B2 | 12/2014 | Barthe et al. |
| 8,915,854 B2 | 12/2014 | Slayton et al. |
| 8,915,870 B2 | 12/2014 | Barthe et al. |
| 8,920,320 B2 | 12/2014 | Stecco et al. |
| 8,920,324 B2 | 12/2014 | Slayton et al. |
| 8,926,533 B2 | 1/2015 | Bockenstedt et al. |
| 8,932,224 B2 | 1/2015 | Barthe et al. |
| 8,932,238 B2 | 1/2015 | Wing et al. |
| 8,968,205 B2 | 3/2015 | Zeng et al. |
| 9,011,336 B2 | 4/2015 | Slayton et al. |
| 9,039,617 B2 | 5/2015 | Slayton et al. |
| 9,039,619 B2 | 5/2015 | Barthe et al. |
| 9,050,116 B2 | 6/2015 | Homer |
| 9,095,697 B2 | 8/2015 | Barthe et al. |
| 9,107,798 B2 | 8/2015 | Azhari et al. |
| 9,114,247 B2 | 8/2015 | Barthe et al. |
| 9,180,314 B2 | 11/2015 | Desilets et al. |
| 9,216,276 B2 | 12/2015 | Slayton et al. |
| 9,220,915 B2 | 12/2015 | Liu et al. |
| 9,272,162 B2 | 3/2016 | Slayton et al. |
| 9,283,409 B2 | 3/2016 | Slayton et al. |
| 9,283,410 B2 | 3/2016 | Slayton et al. |
| 9,295,607 B2 | 3/2016 | Rosenberg |
| 9,308,390 B2 | 4/2016 | Youngquist |
| 9,308,391 B2 | 4/2016 | Liu et al. |
| 9,314,650 B2 | 4/2016 | Rosenberg et al. |
| 9,320,537 B2 | 4/2016 | Slayton et al. |
| 9,345,910 B2 | 5/2016 | Slayton et al. |
| 9,421,029 B2 | 8/2016 | Barthe et al. |
| 9,427,600 B2 | 8/2016 | Barthe et al. |
| 9,427,601 B2 | 8/2016 | Barthe et al. |
| 9,433,803 B2 | 9/2016 | Lin et al. |
| 9,440,093 B2 | 9/2016 | Homer |
| 9,440,096 B2 | 9/2016 | Barthe et al. |
| 9,492,645 B2 | 11/2016 | Zhou et al. |
| 9,492,686 B2 | 11/2016 | Da Silva |
| 9,498,651 B2 | 11/2016 | Sapozhnikov et al. |
| 9,510,802 B2 | 12/2016 | Barthe et al. |
| 9,522,290 B2 | 12/2016 | Slayton et al. |
| 9,532,832 B2 | 1/2017 | Ron Edoute et al. |
| 9,533,174 B2 | 1/2017 | Barthe et al. |
| 9,533,175 B2 | 1/2017 | Slayton et al. |
| 9,545,529 B2 | 1/2017 | Britva et al. |
| 9,566,454 B2 | 2/2017 | Barthe et al. |
| 9,623,267 B2 | 4/2017 | Ulric et al. |
| 9,694,211 B2 | 7/2017 | Barthe et al. |
| 9,694,212 B2 | 7/2017 | Barthe et al. |
| 9,700,340 B2 | 7/2017 | Barthe et al. |
| 9,707,412 B2 | 7/2017 | Slayton et al. |
| 9,710,607 B2 | 7/2017 | Ramdas et al. |
| 9,713,731 B2 | 7/2017 | Slayton et al. |
| 9,802,063 B2 | 10/2017 | Barthe et al. |
| 9,827,449 B2 | 11/2017 | Barthe et al. |
| 9,827,450 B2 | 11/2017 | Slayton et al. |
| 9,833,639 B2 | 12/2017 | Slayton et al. |
| 9,833,640 B2 | 12/2017 | Barthe et al. |
| 9,895,560 B2 | 2/2018 | Barthe et al. |
| 9,907,535 B2 | 3/2018 | Barthe et al. |
| 9,919,167 B2 | 3/2018 | Domankevitz |
| 9,974,982 B2 | 5/2018 | Slayton et al. |
| 9,993,664 B2 | 6/2018 | Aviad et al. |
| 10,010,721 B2 | 7/2018 | Slayton et al. |
| 10,010,724 B2 | 7/2018 | Barthe et al. |
| 10,010,725 B2 | 7/2018 | Slayton et al. |
| 10,010,726 B2 | 7/2018 | Barthe et al. |
| 10,016,626 B2 | 7/2018 | Zovrin et al. |
| 10,046,181 B2 | 8/2018 | Barthe et al. |
| 10,046,182 B2 | 8/2018 | Barthe et al. |
| 10,070,883 B2 | 9/2018 | Barthe et al. |
| 10,183,183 B2 | 1/2019 | Burdette |
| 10,226,645 B2 | 3/2019 | Barthe |
| 10,238,894 B2 | 3/2019 | Slayton et al. |
| 10,245,450 B2 | 4/2019 | Slayton et al. |
| 10,252,086 B2 | 4/2019 | Barthe et al. |
| 10,265,550 B2 | 4/2019 | Barthe et al. |
| 10,272,272 B2 | 4/2019 | Lee et al. |
| 10,300,308 B2 | 5/2019 | Seip et al. |
| 10,328,289 B2 | 6/2019 | Barthe et al. |
| 10,406,383 B2 | 9/2019 | Luebcke |
| 10,420,960 B2 | 9/2019 | Emery |
| 10,420,961 B2 | 9/2019 | Lacoste |
| 10,485,573 B2 | 11/2019 | Clark, III et al. |
| 10,492,862 B2 | 12/2019 | Domankevitz |
| 10,525,288 B2 | 1/2020 | Slayton et al. |
| 10,532,230 B2 | 1/2020 | Barthe et al. |
| 10,537,304 B2 | 1/2020 | Barthe et al. |
| 10,556,123 B2 | 2/2020 | Altshuler et al. |
| 10,583,287 B2 | 3/2020 | Schwarz |
| 10,603,519 B2 | 3/2020 | Slayton et al. |
| 10,603,523 B2 | 3/2020 | Slayton et al. |
| 10,610,705 B2 | 4/2020 | Barthe et al. |
| 10,610,706 B2 | 4/2020 | Barthe et al. |
| 10,639,006 B2 | 5/2020 | Choi et al. |
| 10,639,504 B2 | 5/2020 | Kim |
| 10,751,246 B2 | 8/2020 | Kaila |
| 10,772,646 B2 | 9/2020 | Lu et al. |
| 10,780,298 B2 | 9/2020 | Cain et al. |
| 10,888,716 B2 | 1/2021 | Slayton et al. |
| 10,888,717 B2 | 1/2021 | Slayton et al. |
| 10,888,718 B2 | 1/2021 | Barthe et al. |
| 10,960,236 B2 | 3/2021 | Slayton et al. |
| 2001/0009997 A1 | 7/2001 | Pope |
| 2001/0009999 A1 | 7/2001 | Kaufman et al. |
| 2001/0014780 A1 | 8/2001 | Martin |
| 2001/0014819 A1 | 8/2001 | Ingle |
| 2001/0031922 A1 | 10/2001 | Weng |
| 2001/0039380 A1 | 11/2001 | Larson et al. |
| 2001/0041880 A1 | 11/2001 | Brisken |
| 2002/0000763 A1 | 1/2002 | Jones |
| 2002/0002345 A1 | 1/2002 | Marlinghaus |
| 2002/0040199 A1 | 4/2002 | Klopotek |
| 2002/0040442 A1 | 4/2002 | Ishidera |
| 2002/0055702 A1 | 5/2002 | Atala |
| 2002/0062077 A1 | 5/2002 | Emmenegger |
| 2002/0062142 A1 | 5/2002 | Knowlton |
| 2002/0072691 A1 | 6/2002 | Thompson et al. |
| 2002/0082528 A1 | 6/2002 | Friedman |
| 2002/0082529 A1 | 6/2002 | Suorsa et al. |
| 2002/0082589 A1 | 6/2002 | Friedman |
| 2002/0087080 A1 | 7/2002 | Slayton |
| 2002/0095143 A1 | 7/2002 | Key |
| 2002/0099094 A1 | 7/2002 | Anderson |
| 2002/0111569 A1 | 8/2002 | Rosenschien et al. |
| 2002/0115917 A1 | 8/2002 | Honda et al. |
| 2002/0128639 A1 | 8/2002 | Pless et al. |
| 2002/0128648 A1 | 9/2002 | Weber |
| 2002/0143252 A1 | 10/2002 | Dunne et al. |
| 2002/0156400 A1 | 10/2002 | Babaev |
| 2002/0161357 A1 | 10/2002 | Anderson |

(56) References Cited

U.S. PATENT DOCUMENTS

| | | |
|---|---|---|
| 2002/0165529 A1 | 11/2002 | Danek |
| 2002/0168049 A1 | 11/2002 | Schriever |
| 2002/0169394 A1 | 11/2002 | Eppstein et al. |
| 2002/0169442 A1 | 11/2002 | Neev |
| 2002/0173721 A1 | 11/2002 | Grunwald et al. |
| 2002/0193784 A1 | 12/2002 | McHale et al. |
| 2002/0193831 A1 | 12/2002 | Smith |
| 2003/0009153 A1 | 1/2003 | Brisken et al. |
| 2003/0014039 A1 | 1/2003 | Barzell et al. |
| 2003/0018255 A1 | 1/2003 | Martin |
| 2003/0018270 A1 | 1/2003 | Makin et al. |
| 2003/0023283 A1 | 1/2003 | McDaniel |
| 2003/0028111 A1 | 2/2003 | Vaezy et al. |
| 2003/0028113 A1 | 2/2003 | Gilbert et al. |
| 2003/0032900 A1 | 2/2003 | Ella |
| 2003/0036706 A1 | 2/2003 | Slayton et al. |
| 2003/0040739 A1 | 2/2003 | Koop |
| 2003/0050678 A1 | 3/2003 | Sierra |
| 2003/0055308 A1 | 3/2003 | Friemel et al. |
| 2003/0055417 A1 | 3/2003 | Truckai et al. |
| 2003/0060736 A1 | 3/2003 | Martin et al. |
| 2003/0065313 A1 | 4/2003 | Koop |
| 2003/0066708 A1 | 4/2003 | Allison et al. |
| 2003/0073907 A1 | 4/2003 | Taylor |
| 2003/0074023 A1 | 4/2003 | Kaplan |
| 2003/0083536 A1 | 5/2003 | Eshel |
| 2003/0092988 A1 | 5/2003 | Makin |
| 2003/0097071 A1 | 5/2003 | Halmann et al. |
| 2003/0099383 A1 | 5/2003 | Lefebvre |
| 2003/0125629 A1 | 7/2003 | Ustuner |
| 2003/0135135 A1 | 7/2003 | Miwa et al. |
| 2003/0139790 A1 | 7/2003 | Ingle et al. |
| 2003/0149366 A1 | 8/2003 | Stringer et al. |
| 2003/0153961 A1 | 8/2003 | Babaev |
| 2003/0171678 A1 | 9/2003 | Batten et al. |
| 2003/0171701 A1 | 9/2003 | Babaev |
| 2003/0176790 A1 | 9/2003 | Slayton |
| 2003/0191396 A1 | 10/2003 | Sanghvi |
| 2003/0199794 A1 | 10/2003 | Sakurai et al. |
| 2003/0200481 A1 | 10/2003 | Stanley |
| 2003/0212129 A1 | 11/2003 | Liu et al. |
| 2003/0212351 A1 | 11/2003 | Hissong |
| 2003/0212393 A1 | 11/2003 | Knowlton |
| 2003/0216648 A1 | 11/2003 | Lizzi et al. |
| 2003/0216795 A1 | 11/2003 | Harth |
| 2003/0220536 A1 | 11/2003 | Hissong |
| 2003/0220585 A1 | 11/2003 | Hissong |
| 2003/0229331 A1 | 12/2003 | Brisken et al. |
| 2003/0233085 A1 | 12/2003 | Giammarusti |
| 2003/0236487 A1 | 12/2003 | Knowlton |
| 2004/0000316 A1 | 1/2004 | Knowlton |
| 2004/0001809 A1 | 1/2004 | Brisken |
| 2004/0002658 A1 | 1/2004 | Marian, Jr. |
| 2004/0002705 A1 | 1/2004 | Knowlton |
| 2004/0010222 A1 | 1/2004 | Nunomura et al. |
| 2004/0015079 A1 | 1/2004 | Berger et al. |
| 2004/0015106 A1 | 1/2004 | Coleman |
| 2004/0030227 A1 | 2/2004 | Littrup |
| 2004/0030268 A1 | 2/2004 | Weng et al. |
| 2004/0039312 A1 | 2/2004 | Hillstead |
| 2004/0039418 A1 | 2/2004 | Elstrom |
| 2004/0041563 A1 | 3/2004 | Lewin et al. |
| 2004/0041880 A1 | 3/2004 | Ikeda et al. |
| 2004/0042168 A1 | 3/2004 | Yang et al. |
| 2004/0044375 A1 | 3/2004 | Diederich et al. |
| 2004/0049134 A1 | 3/2004 | Tosaya et al. |
| 2004/0049734 A1 | 3/2004 | Tosaya et al. |
| 2004/0059266 A1 | 3/2004 | Fry |
| 2004/0068186 A1 | 4/2004 | Ishida et al. |
| 2004/0073079 A1 | 4/2004 | Altshuler et al. |
| 2004/0073113 A1 | 4/2004 | Salgo |
| 2004/0073115 A1 | 4/2004 | Horzewski et al. |
| 2004/0073116 A1 | 4/2004 | Smith |
| 2004/0073204 A1 | 4/2004 | Ryan et al. |
| 2004/0077977 A1 | 4/2004 | Ella et al. |
| 2004/0082857 A1 | 4/2004 | Schonenberger |
| 2004/0082859 A1 | 4/2004 | Schaer |
| 2004/0102697 A1 | 5/2004 | Evron |
| 2004/0105559 A1 | 6/2004 | Aylward et al. |
| 2004/0106867 A1 | 6/2004 | Eshel et al. |
| 2004/0122323 A1 | 6/2004 | Vortman et al. |
| 2004/0122493 A1 | 6/2004 | Ishibashi et al. |
| 2004/0143297 A1 | 7/2004 | Ramsey |
| 2004/0152982 A1 | 8/2004 | Hwang et al. |
| 2004/0158150 A1 | 8/2004 | Rabiner et al. |
| 2004/0186535 A1 | 9/2004 | Knowlton |
| 2004/0189155 A1 | 9/2004 | Funakubo |
| 2004/0206365 A1 | 10/2004 | Knowlton |
| 2004/0210214 A1 | 10/2004 | Knowlton |
| 2004/0217675 A1 | 11/2004 | Desilets |
| 2004/0249318 A1 | 12/2004 | Tanaka |
| 2004/0254620 A1 | 12/2004 | Lacoste |
| 2004/0267252 A1 | 12/2004 | Washington et al. |
| 2005/0007879 A1 | 1/2005 | Nishida |
| 2005/0033201 A1 | 2/2005 | Takahashi |
| 2005/0033316 A1 | 2/2005 | Kertz |
| 2005/0038340 A1 | 2/2005 | Vaezy et al. |
| 2005/0055018 A1 | 3/2005 | Kreindel |
| 2005/0055073 A1 | 3/2005 | Weber |
| 2005/0061834 A1 | 3/2005 | Garcia et al. |
| 2005/0070961 A1 | 3/2005 | Maki |
| 2005/0074407 A1 | 4/2005 | Smith |
| 2005/0080469 A1 | 4/2005 | Larson |
| 2005/0085731 A1 | 4/2005 | Miller et al. |
| 2005/0091770 A1 | 5/2005 | Mourad et al. |
| 2005/0096542 A1 | 5/2005 | Weng et al. |
| 2005/0104690 A1 | 5/2005 | Larson et al. |
| 2005/0113689 A1 | 5/2005 | Gritzky |
| 2005/0131302 A1 | 6/2005 | Poland |
| 2005/0137656 A1 | 6/2005 | Malak |
| 2005/0143677 A1 | 6/2005 | Young et al. |
| 2005/0154313 A1 | 7/2005 | Desilets |
| 2005/0154314 A1 | 7/2005 | Quistgaard |
| 2005/0154332 A1 | 7/2005 | Zanelli |
| 2005/0154431 A1 | 7/2005 | Quistgaard |
| 2005/0187495 A1 | 8/2005 | Quistgaard |
| 2005/0191252 A1 | 9/2005 | Mitsui |
| 2005/0193451 A1 | 9/2005 | Quistgaard |
| 2005/0193820 A1 | 9/2005 | Sheljaskow et al. |
| 2005/0197681 A1 | 9/2005 | Barolet et al. |
| 2005/0203399 A1* | 9/2005 | Vaezy ............ A61B 8/08 600/439 |
| 2005/0228281 A1 | 10/2005 | Nefos |
| 2005/0240127 A1 | 10/2005 | Seip et al. |
| 2005/0240170 A1 | 10/2005 | Zhang et al. |
| 2005/0251120 A1 | 11/2005 | Anderson et al. |
| 2005/0251125 A1 | 11/2005 | Pless et al. |
| 2005/0256406 A1 | 11/2005 | Barthe |
| 2005/0261584 A1 | 11/2005 | Eshel |
| 2005/0261585 A1 | 11/2005 | Makin et al. |
| 2005/0267454 A1 | 12/2005 | Hissong |
| 2005/0288748 A1 | 12/2005 | Li et al. |
| 2006/0004306 A1 | 1/2006 | Altshuler |
| 2006/0020260 A1 | 1/2006 | Dover et al. |
| 2006/0025756 A1 | 2/2006 | Francischelli |
| 2006/0042201 A1 | 3/2006 | Curry |
| 2006/0058664 A1 | 3/2006 | Barthe |
| 2006/0058671 A1 | 3/2006 | Vitek et al. |
| 2006/0058707 A1 | 3/2006 | Barthe |
| 2006/0058712 A1 | 3/2006 | Altshuler et al. |
| 2006/0074309 A1 | 4/2006 | Bonnefous |
| 2006/0074313 A1 | 4/2006 | Slayton et al. |
| 2006/0074314 A1 | 4/2006 | Slayton |
| 2006/0074355 A1 | 4/2006 | Slayton |
| 2006/0079816 A1 | 4/2006 | Barthe |
| 2006/0079868 A1 | 4/2006 | Makin |
| 2006/0084891 A1 | 4/2006 | Barthe |
| 2006/0089632 A1 | 4/2006 | Barthe |
| 2006/0089688 A1 | 4/2006 | Panescu |
| 2006/0094988 A1 | 5/2006 | Tosaya |
| 2006/0106325 A1 | 5/2006 | Perrier |
| 2006/0111744 A1 | 5/2006 | Makin |
| 2006/0116583 A1 | 6/2006 | Ogasawara et al. |
| 2006/0116671 A1 | 6/2006 | Slayton |

(56) References Cited

U.S. PATENT DOCUMENTS

| | | |
|---|---|---|
| 2006/0122508 A1 | 6/2006 | Slayton |
| 2006/0122509 A1 | 6/2006 | Desilets |
| 2006/0161062 A1 | 7/2006 | Arditi et al. |
| 2006/0184069 A1 | 8/2006 | Vaitekunas |
| 2006/0184071 A1 | 8/2006 | Klopotek |
| 2006/0189972 A1 | 8/2006 | Grossman |
| 2006/0206105 A1 | 9/2006 | Chopra |
| 2006/0224090 A1 | 10/2006 | Ostrovsky et al. |
| 2006/0229514 A1 | 10/2006 | Wiener |
| 2006/0238068 A1 | 10/2006 | May et al. |
| 2006/0241440 A1 | 10/2006 | Eshel |
| 2006/0241442 A1 | 10/2006 | Barthe |
| 2006/0241470 A1 | 10/2006 | Novak et al. |
| 2006/0241576 A1 | 10/2006 | Diederich et al. |
| 2006/0250046 A1 | 11/2006 | Koizumi et al. |
| 2006/0282691 A1 | 12/2006 | Barthe |
| 2006/0291710 A1 | 12/2006 | Wang et al. |
| 2007/0016039 A1 | 1/2007 | Vortman et al. |
| 2007/0032784 A1 | 2/2007 | Gilklich et al. |
| 2007/0035201 A1 | 2/2007 | Desilets |
| 2007/0055154 A1 | 3/2007 | Torbati |
| 2007/0055155 A1 | 3/2007 | Owen et al. |
| 2007/0055156 A1 | 3/2007 | Desilets et al. |
| 2007/0065420 A1 | 3/2007 | Johnson |
| 2007/0083120 A1 | 4/2007 | Cain et al. |
| 2007/0087060 A1 | 4/2007 | Dietrich |
| 2007/0088245 A1 | 4/2007 | Babaev et al. |
| 2007/0088346 A1 | 4/2007 | Mirizzi et al. |
| 2007/0161902 A1 | 7/2007 | Dan |
| 2007/0166357 A1 | 7/2007 | Shaffer et al. |
| 2007/0167709 A1 | 7/2007 | Slayton |
| 2007/0018553 A1 | 8/2007 | Kennedy |
| 2007/0208253 A1 | 9/2007 | Slayton |
| 2007/0219448 A1* | 9/2007 | Seip ............ A61B 8/06 600/454 |
| 2007/0219604 A1 | 9/2007 | Yaroslavsky et al. |
| 2007/0219605 A1 | 9/2007 | Yaroslavsky et al. |
| 2007/0238994 A1 | 10/2007 | Stecco et al. |
| 2007/0239075 A1 | 10/2007 | Rosenberg |
| 2007/0239077 A1 | 10/2007 | Azhari et al. |
| 2007/0239079 A1 | 10/2007 | Manstein et al. |
| 2007/0239142 A1 | 10/2007 | Altshuler |
| 2008/0015435 A1 | 1/2008 | Cribbs et al. |
| 2008/0027328 A1 | 1/2008 | Klopotek |
| 2008/0033458 A1 | 2/2008 | McLean et al. |
| 2008/0039724 A1 | 2/2008 | Seip et al. |
| 2008/0071255 A1 | 3/2008 | Barthe |
| 2008/0086054 A1 | 4/2008 | Slayton |
| 2008/0086056 A1 | 4/2008 | Chang et al. |
| 2008/0097214 A1 | 4/2008 | Meyers et al. |
| 2008/0097253 A1 | 4/2008 | Pedersen et al. |
| 2008/0114251 A1 | 5/2008 | Weymer |
| 2008/0139943 A1 | 6/2008 | Deng et al. |
| 2008/0139974 A1 | 6/2008 | Da Silva |
| 2008/0146970 A1 | 6/2008 | Litman et al. |
| 2008/0167556 A1 | 7/2008 | Thompson |
| 2008/0183077 A1 | 7/2008 | Moreau-Gobard et al. |
| 2008/0183110 A1 | 7/2008 | Davenport et al. |
| 2008/0188745 A1 | 8/2008 | Chen et al. |
| 2008/0194964 A1 | 8/2008 | Randall et al. |
| 2008/0195000 A1 | 8/2008 | Spooner et al. |
| 2008/0200810 A1 | 8/2008 | Buchalter |
| 2008/0200813 A1 | 8/2008 | Quistgaard |
| 2008/0214966 A1 | 9/2008 | Slayton |
| 2008/0214988 A1 | 9/2008 | Altshuler et al. |
| 2008/0221491 A1 | 9/2008 | Slayton |
| 2008/0223379 A1 | 9/2008 | Stuker et al. |
| 2008/0242991 A1 | 10/2008 | Moon et al. |
| 2008/0243035 A1 | 10/2008 | Crunkilton |
| 2008/0269608 A1 | 10/2008 | Anderson et al. |
| 2008/0275342 A1 | 11/2008 | Barthe |
| 2008/0281206 A1 | 11/2008 | Bartlett et al. |
| 2008/0281236 A1 | 11/2008 | Eshel et al. |
| 2008/0281237 A1 | 11/2008 | Slayton |
| 2008/0281255 A1 | 11/2008 | Slayton |
| 2008/0294072 A1 | 11/2008 | Crutchfield, III |
| 2008/0294073 A1 | 11/2008 | Barthe |
| 2008/0319356 A1 | 12/2008 | Cain |
| 2009/0005680 A1 | 1/2009 | Jones et al. |
| 2009/0012394 A1 | 1/2009 | Hobelsberger et al. |
| 2009/0043198 A1 | 2/2009 | Milner et al. |
| 2009/0043293 A1 | 2/2009 | Pankratov et al. |
| 2009/0048514 A1 | 2/2009 | Azhari et al. |
| 2009/0069677 A1 | 3/2009 | Chen et al. |
| 2009/0093737 A1 | 4/2009 | Chomas et al. |
| 2009/0156969 A1 | 6/2009 | Santangelo |
| 2009/0163807 A1 | 6/2009 | Sliwa |
| 2009/0171252 A1 | 7/2009 | Bockenstedt et al. |
| 2009/0171266 A1 | 7/2009 | Harris |
| 2009/0177122 A1 | 7/2009 | Peterson |
| 2009/0177123 A1 | 7/2009 | Peterson |
| 2009/0182231 A1 | 7/2009 | Barthe et al. |
| 2009/0198157 A1 | 8/2009 | Babaev et al. |
| 2009/0216159 A1 | 8/2009 | Slayton et al. |
| 2009/0226424 A1 | 9/2009 | Hsu |
| 2009/0227910 A1 | 9/2009 | Pedersen et al. |
| 2009/0230823 A1 | 9/2009 | Kushculey et al. |
| 2009/0253988 A1 | 10/2009 | Slayton et al. |
| 2009/0281463 A1 | 11/2009 | Chapelon et al. |
| 2009/0312693 A1 | 12/2009 | Thapliyal et al. |
| 2009/0318909 A1 | 12/2009 | Debenedictis et al. |
| 2009/0326420 A1 | 12/2009 | Moonen et al. |
| 2010/0011236 A1 | 1/2010 | Barthe et al. |
| 2010/0022919 A1 | 1/2010 | Peterson |
| 2010/0022921 A1 | 1/2010 | Seip et al. |
| 2010/0022922 A1 | 1/2010 | Barthe et al. |
| 2010/0030076 A1 | 2/2010 | Vortman et al. |
| 2010/0042020 A1 | 2/2010 | Ben-Ezra |
| 2010/0049178 A1 | 2/2010 | Deem et al. |
| 2010/0056925 A1 | 3/2010 | Zhang et al. |
| 2010/0056962 A1 | 3/2010 | Vortman et al. |
| 2010/0100014 A1 | 4/2010 | Eshel et al. |
| 2010/0113983 A1 | 5/2010 | Heckerman et al. |
| 2010/0130891 A1 | 5/2010 | Taggart et al. |
| 2010/0160782 A1 | 6/2010 | Slayton et al. |
| 2010/0160837 A1 | 6/2010 | Hunziker et al. |
| 2010/0168576 A1 | 7/2010 | Poland et al. |
| 2010/0191120 A1 | 7/2010 | Kraus et al. |
| 2010/0241035 A1 | 9/2010 | Barthe et al. |
| 2010/0249602 A1 | 9/2010 | Buckley et al. |
| 2010/0249669 A1 | 9/2010 | Ulric et al. |
| 2010/0256489 A1 | 10/2010 | Pedersen et al. |
| 2010/0274161 A1 | 10/2010 | Azhari et al. |
| 2010/0280420 A1 | 11/2010 | Barthe et al. |
| 2010/0286518 A1 | 11/2010 | Lee et al. |
| 2010/0312150 A1 | 12/2010 | Douglas et al. |
| 2011/0040171 A1 | 2/2011 | Foley et al. |
| 2011/0040190 A1 | 2/2011 | Jahnke et al. |
| 2011/0040213 A1 | 2/2011 | Dietz et al. |
| 2011/0040214 A1 | 2/2011 | Foley et al. |
| 2011/0066084 A1 | 3/2011 | Desilets et al. |
| 2011/0072970 A1 | 3/2011 | Slobodzian et al. |
| 2011/0077514 A1 | 3/2011 | Ulric et al. |
| 2011/0079083 A1* | 4/2011 | Yoo ............ G01S 7/52065 73/632 |
| 2011/0087099 A1 | 4/2011 | Eshel et al. |
| 2011/0087255 A1 | 4/2011 | McCormack et al. |
| 2011/0112405 A1 | 5/2011 | Barthe et al. |
| 2011/0144490 A1 | 6/2011 | Davis et al. |
| 2011/0178444 A1 | 7/2011 | Slayton et al. |
| 2011/0178541 A1 | 7/2011 | Azhari |
| 2011/0190745 A1 | 8/2011 | Uebelhoer et al. |
| 2011/0201976 A1 | 8/2011 | Sanghvi et al. |
| 2011/0251524 A1 | 10/2011 | Azhari et al. |
| 2011/0251527 A1 | 10/2011 | Kushculey et al. |
| 2011/0270137 A1 | 11/2011 | Goren et al. |
| 2011/0319793 A1 | 12/2011 | Henrik et al. |
| 2011/0319794 A1 | 12/2011 | Gertner |
| 2012/0004549 A1 | 1/2012 | Barthe et al. |
| 2012/0016239 A1 | 1/2012 | Barthe et al. |
| 2012/0029353 A1 | 2/2012 | Slayton et al. |
| 2012/0035473 A1 | 2/2012 | Sanghvi et al. |
| 2012/0035475 A1 | 2/2012 | Barthe et al. |
| 2012/0035476 A1 | 2/2012 | Barthe et al. |

(56) References Cited

U.S. PATENT DOCUMENTS

| | | |
|---|---|---|
| 2012/0046547 A1 | 2/2012 | Barthe et al. |
| 2012/0053458 A1 | 3/2012 | Barthe et al. |
| 2012/0059288 A1 | 3/2012 | Barthe et al. |
| 2012/0111339 A1 | 5/2012 | Barthe et al. |
| 2012/0123304 A1 | 5/2012 | Rybyanets et al. |
| 2012/0136280 A1 | 5/2012 | Rosenberg et al. |
| 2012/0136282 A1 | 5/2012 | Rosenberg et al. |
| 2012/0143056 A1 | 6/2012 | Slayton et al. |
| 2012/0143100 A1 | 6/2012 | Jeong et al. |
| 2012/0165668 A1 | 6/2012 | Slayton et al. |
| 2012/0165848 A1 | 6/2012 | Slayton et al. |
| 2012/0191019 A1 | 7/2012 | Desilets et al. |
| 2012/0191020 A1 | 7/2012 | Vitek et al. |
| 2012/0197120 A1 | 8/2012 | Makin et al. |
| 2012/0197121 A1 | 8/2012 | Slayton et al. |
| 2012/0209150 A1 | 8/2012 | Zeng et al. |
| 2012/0215105 A1 | 8/2012 | Slayton et al. |
| 2012/0271202 A1 | 10/2012 | Wisdom |
| 2012/0271294 A1* | 10/2012 | Barthe .................. A61B 8/461 606/28 |
| 2012/0277639 A1 | 11/2012 | Pollock et al. |
| 2012/0296240 A1 | 11/2012 | Azhari et al. |
| 2012/0302883 A1 | 11/2012 | Kong et al. |
| 2012/0316426 A1 | 12/2012 | Foley et al. |
| 2012/0330197 A1 | 12/2012 | Makin et al. |
| 2012/0330222 A1 | 12/2012 | Makin et al. |
| 2012/0330223 A1 | 12/2012 | Makin et al. |
| 2012/0330283 A1 | 12/2012 | Hyde et al. |
| 2012/0330284 A1 | 12/2012 | Hyde et al. |
| 2013/0012755 A1 | 1/2013 | Slayton |
| 2013/0012816 A1 | 1/2013 | Slayton et al. |
| 2013/0012838 A1 | 1/2013 | Jaeger et al. |
| 2013/0012842 A1 | 1/2013 | Barthe |
| 2013/0018285 A1 | 1/2013 | Park et al. |
| 2013/0018286 A1 | 1/2013 | Slayton et al. |
| 2013/0046209 A1 | 2/2013 | Slayton et al. |
| 2013/0051178 A1 | 2/2013 | Rybyanets |
| 2013/0060170 A1 | 3/2013 | Lee et al. |
| 2013/0066208 A1 | 3/2013 | Barthe et al. |
| 2013/0066237 A1 | 3/2013 | Smotrich et al. |
| 2013/0072826 A1 | 3/2013 | Slayton et al. |
| 2013/0073001 A1 | 3/2013 | Campbell |
| 2013/0096471 A1 | 4/2013 | Slayton et al. |
| 2013/0096596 A1 | 4/2013 | Schafer |
| 2013/0190659 A1 | 7/2013 | Slayton et al. |
| 2013/0211293 A1 | 8/2013 | Auboiroux et al. |
| 2013/0225994 A1 | 8/2013 | Hsu et al. |
| 2013/0268032 A1 | 10/2013 | Neev |
| 2013/0274603 A1 | 10/2013 | Barthe et al. |
| 2013/0278111 A1 | 10/2013 | Sammoura |
| 2013/0281853 A1 | 10/2013 | Slayton et al. |
| 2013/0281891 A1 | 10/2013 | Slayton et al. |
| 2013/0296697 A1 | 11/2013 | Slayton et al. |
| 2013/0296700 A1 | 11/2013 | Slayton et al. |
| 2013/0296743 A1 | 11/2013 | Lee et al. |
| 2013/0303904 A1 | 11/2013 | Barthe et al. |
| 2013/0303905 A1 | 11/2013 | Barthe et al. |
| 2013/0310714 A1 | 11/2013 | Eshel et al. |
| 2013/0310863 A1 | 11/2013 | Makin et al. |
| 2013/0345562 A1 | 12/2013 | Barthe et al. |
| 2014/0024974 A1 | 1/2014 | Slayton et al. |
| 2014/0050054 A1 | 2/2014 | Toda et al. |
| 2014/0081300 A1 | 3/2014 | Melodelima et al. |
| 2014/0082907 A1 | 3/2014 | Barthe et al. |
| 2014/0117814 A1 | 5/2014 | Toda et al. |
| 2014/0142430 A1 | 5/2014 | Slayton et al. |
| 2014/0148834 A1 | 5/2014 | Barthe et al. |
| 2014/0155747 A1 | 6/2014 | Bennett |
| 2014/0180174 A1 | 6/2014 | Slayton et al. |
| 2014/0187944 A1 | 7/2014 | Slayton et al. |
| 2014/0188015 A1 | 7/2014 | Slayton et al. |
| 2014/0188145 A1 | 7/2014 | Slayton et al. |
| 2014/0194723 A1 | 7/2014 | Herzog et al. |
| 2014/0208856 A1 | 7/2014 | Schmid |
| 2014/0221823 A1 | 8/2014 | Keogh et al. |
| 2014/0236049 A1 | 8/2014 | Barthe et al. |
| 2014/0236061 A1 | 8/2014 | Lee et al. |
| 2014/0243713 A1 | 8/2014 | Slayton et al. |
| 2014/0257145 A1 | 9/2014 | Emery |
| 2014/0276055 A1 | 9/2014 | Barthe et al. |
| 2014/0330124 A1* | 11/2014 | Carol .................. A61B 8/12 600/439 |
| 2015/0000674 A1 | 1/2015 | Barthe et al. |
| 2015/0025420 A1 | 1/2015 | Slayton et al. |
| 2015/0064165 A1 | 3/2015 | Perry et al. |
| 2015/0080723 A1 | 3/2015 | Barthe et al. |
| 2015/0080771 A1 | 3/2015 | Barthe et al. |
| 2015/0080874 A1 | 3/2015 | Slayton et al. |
| 2015/0088182 A1 | 3/2015 | Slayton et al. |
| 2015/0141734 A1 | 5/2015 | Chapelon et al. |
| 2015/0164734 A1 | 6/2015 | Slayton et al. |
| 2015/0165238 A1 | 6/2015 | Slayton et al. |
| 2015/0165243 A1 | 6/2015 | Slayton et al. |
| 2015/0174388 A1 | 6/2015 | Slayton |
| 2015/0202468 A1 | 7/2015 | Slayton et al. |
| 2015/0217141 A1 | 8/2015 | Barthe et al. |
| 2015/0224347 A1* | 8/2015 | Barthe .................. G01S 15/8909 601/2 |
| 2015/0238258 A1 | 8/2015 | Palero et al. |
| 2015/0297188 A1 | 10/2015 | Konofagou |
| 2015/0321026 A1 | 11/2015 | Branson et al. |
| 2015/0360058 A1 | 12/2015 | Barthe et al. |
| 2015/0374333 A1 | 12/2015 | Barthe et al. |
| 2015/0375014 A1 | 12/2015 | Slayton et al. |
| 2016/0001097 A1 | 1/2016 | Cho et al. |
| 2016/0016015 A1 | 1/2016 | Slayton et al. |
| 2016/0027994 A1 | 1/2016 | Toda et al. |
| 2016/0151618 A1 | 6/2016 | Powers et al. |
| 2016/0158580 A1 | 6/2016 | Slayton et al. |
| 2016/0175619 A1 | 6/2016 | Lee et al. |
| 2016/0206335 A1 | 7/2016 | Slayton |
| 2016/0206341 A1 | 7/2016 | Slayton |
| 2016/0256675 A1 | 9/2016 | Slayton |
| 2016/0296769 A1 | 10/2016 | Barthe et al. |
| 2016/0310444 A1 | 10/2016 | Dobak, III |
| 2016/0361571 A1 | 12/2016 | Bernabei |
| 2016/0361572 A1 | 12/2016 | Slayton |
| 2017/0028227 A1 | 2/2017 | Emery et al. |
| 2017/0043190 A1 | 2/2017 | Barthe et al. |
| 2017/0050019 A1 | 2/2017 | Ron Edoute et al. |
| 2017/0080257 A1 | 3/2017 | Paunescu et al. |
| 2017/0100585 A1 | 4/2017 | Hall et al. |
| 2017/0119345 A1* | 5/2017 | Levien .................. A61B 8/085 |
| 2017/0136263 A1 | 5/2017 | Reil |
| 2017/0209201 A1 | 7/2017 | Slayton et al. |
| 2017/0209202 A1 | 7/2017 | Friedrichs et al. |
| 2017/0304654 A1 | 10/2017 | Blanche et al. |
| 2017/0368574 A1 | 12/2017 | Sammoura |
| 2018/0001113 A1 | 1/2018 | Streeter |
| 2018/0015308 A1 | 1/2018 | Reed et al. |
| 2018/0043147 A1 | 2/2018 | Slayton |
| 2018/0099162 A1 | 4/2018 | Bernabei |
| 2018/0099163 A1 | 4/2018 | Bernabei |
| 2018/0126190 A1 | 5/2018 | Aviad et al. |
| 2018/0154184 A1 | 6/2018 | Kong et al. |
| 2018/0207450 A1 | 7/2018 | Sanchez et al. |
| 2018/0272156 A1 | 9/2018 | Slayton et al. |
| 2018/0272157 A1 | 9/2018 | Barthe et al. |
| 2018/0272158 A1 | 9/2018 | Barthe et al. |
| 2018/0272159 A1 | 9/2018 | Slayton et al. |
| 2018/0317884 A1 | 11/2018 | Chapelon et al. |
| 2018/0333595 A1 | 11/2018 | Barthe et al. |
| 2018/0360420 A1 | 12/2018 | Vortman et al. |
| 2019/0000498 A1 | 1/2019 | Barthe et al. |
| 2019/0009110 A1 | 1/2019 | Gross et al. |
| 2019/0009111 A1 | 1/2019 | Myhr et al. |
| 2019/0022405 A1 | 1/2019 | Greenbaum et al. |
| 2019/0038921 A1 | 2/2019 | Domankevitz |
| 2019/0060675 A1 | 2/2019 | Krone et al. |
| 2019/0091490 A1 | 3/2019 | Alexander et al. |
| 2019/0142380 A1 | 5/2019 | Emery et al. |
| 2019/0143148 A1 | 5/2019 | Slayton |
| 2019/0184202 A1 | 6/2019 | Zereshkian et al. |
| 2019/0184203 A1 | 6/2019 | Slayton et al. |

(56) References Cited

U.S. PATENT DOCUMENTS

| | | | |
|---|---|---|---|
| 2019/0184205 A1 | 6/2019 | Slayton et al. | |
| 2019/0184207 A1 | 6/2019 | Barthe et al. | |
| 2019/0184208 A1 | 6/2019 | Barthe et al. | |
| 2019/0224501 A1 | 7/2019 | Burdette | |
| 2019/0262634 A1 | 8/2019 | Barthe et al. | |
| 2019/0282834 A1 | 9/2019 | Zawada et al. | |
| 2019/0290939 A1* | 9/2019 | Watson | A61N 7/02 |
| 2019/0350562 A1 | 11/2019 | Slayton et al. | |
| 2019/0366126 A1 | 12/2019 | Pahk et al. | |
| 2019/0366127 A1 | 12/2019 | Emery | |
| 2019/0366128 A1 | 12/2019 | Slayton et al. | |
| 2020/0094083 A1 | 3/2020 | Slayton et al. | |
| 2020/0100762 A1 | 4/2020 | Barthe et al. | |
| 2020/0129759 A1 | 4/2020 | Schwarz | |
| 2020/0171330 A1 | 6/2020 | Barthe et al. | |
| 2020/0179727 A1 | 6/2020 | Slayton et al. | |
| 2020/0179729 A1 | 6/2020 | Slayton et al. | |
| 2020/0188703 A1 | 6/2020 | Barthe et al. | |
| 2020/0188704 A1 | 6/2020 | Barthe et al. | |
| 2020/0206072 A1 | 7/2020 | Capelli et al. | |
| 2020/0222728 A1 | 7/2020 | Khokhlova et al. | |
| 2021/0038925 A1 | 2/2021 | Emery | |

FOREIGN PATENT DOCUMENTS

| | | |
|---|---|---|
| CN | 104027893 | 9/2014 |
| DE | 4029175 | 3/1992 |
| DE | 10140064 | 3/2003 |
| DE | 10219297 | 11/2003 |
| DE | 10219217 | 12/2004 |
| DE | 20314479 | 12/2004 |
| EP | 0142215 | 5/1984 |
| EP | 0344773 | 12/1989 |
| EP | 1479412 | 11/1991 |
| EP | 0473553 | 4/1992 |
| EP | 670147 | 2/1995 |
| EP | 0661029 | 7/1995 |
| EP | 724894 | 2/1996 |
| EP | 763371 | 11/1996 |
| EP | 1044038 | 10/2000 |
| EP | 1050322 | 11/2000 |
| EP | 1234566 | 8/2002 |
| EP | 1262160 | 12/2002 |
| EP | 0659387 | 4/2003 |
| EP | 1374944 | 1/2004 |
| EP | 1028660 | 1/2008 |
| EP | 1874241 | 1/2008 |
| EP | 1362223 | 5/2008 |
| EP | 1750804 | 7/2008 |
| EP | 1283690 | 11/2008 |
| EP | 1811901 | 4/2009 |
| EP | 1785164 | 8/2009 |
| EP | 2230904 | 9/2010 |
| EP | 1501331 | 6/2011 |
| EP | 2066405 | 11/2011 |
| EP | 2474050 | 7/2012 |
| EP | 2709726 | 11/2015 |
| EP | 1538980 | 1/2017 |
| EP | 3124047 | 1/2017 |
| EP | 2897547 | 11/2017 |
| EP | 2173261 B1 | 8/2018 |
| EP | 3417911 | 12/2018 |
| FR | 2552851 | 9/1983 |
| FR | 2685872 | 1/1992 |
| FR | 2672486 | 8/1992 |
| FR | 2703254 | 3/1994 |
| GB | 2113099 | 8/1983 |
| IL | 102516 | 1/1996 |
| IL | 112369 | 8/1999 |
| IL | 120079 | 3/2001 |
| JP | 63036171 | 2/1988 |
| JP | 03048299 | 3/1991 |
| JP | 3123559 | 5/1991 |
| JP | 03136642 | 6/1991 |
| JP | 4089058 | 3/1992 |
| JP | 04150847 | 5/1992 |
| JP | 7080087 | 3/1995 |
| JP | 07505793 | 6/1995 |
| JP | 7184907 | 7/1995 |
| JP | 7222782 | 8/1995 |
| JP | 09047458 | 2/1997 |
| JP | 9108288 | 4/1997 |
| JP | 9503926 | 4/1997 |
| JP | 3053069 | 10/1998 |
| JP | 11123226 | 5/1999 |
| JP | 11505440 | 5/1999 |
| JP | 11506636 | 6/1999 |
| JP | 10248850 | 9/1999 |
| JP | 2000126310 | 5/2000 |
| JP | 2000166940 | 6/2000 |
| JP | 2000233009 | 8/2000 |
| JP | 2001-46387 | 2/2001 |
| JP | 2001136599 A | 5/2001 |
| JP | 2001170068 | 6/2001 |
| JP | 2002505596 | 2/2002 |
| JP | 2002078764 | 3/2002 |
| JP | 2002515786 | 5/2002 |
| JP | 2002537013 | 5/2002 |
| JP | 2002521118 | 7/2002 |
| JP | 2002537939 | 11/2002 |
| JP | 2003050298 | 7/2003 |
| JP | 2003204982 | 7/2003 |
| JP | 2004-504898 | 2/2004 |
| JP | 2004-507280 | 3/2004 |
| JP | 2004154256 | 3/2004 |
| JP | 2004-509671 | 4/2004 |
| JP | 2004-512856 | 4/2004 |
| JP | 2004147719 | 5/2004 |
| JP | 2005503388 | 2/2005 |
| JP | 2005527336 | 9/2005 |
| JP | 2005323213 | 11/2005 |
| JP | 2006520247 | 9/2006 |
| JP | 2008515559 | 5/2008 |
| JP | 2009518126 | 5/2009 |
| JP | 2010517695 | 5/2010 |
| KR | 2001-0019317 | 3/2001 |
| KR | 1020010024871 | 3/2001 |
| KR | 2002-0038547 | 5/2002 |
| KR | 100400870 | 10/2003 |
| KR | 20060121267 | 11/2006 |
| KR | 1020060113930 | 11/2006 |
| KR | 1020070065332 | 6/2007 |
| KR | 1020070070161 | 7/2007 |
| KR | 1020070098856 | 10/2007 |
| KR | 1020070104878 | 10/2007 |
| KR | 1020070114105 | 11/2007 |
| KR | 1020000059516 | 4/2012 |
| KR | 10-2013-0124598 | 11/2013 |
| KR | 10-1365946 | 2/2014 |
| TW | 386883 | 9/2000 |
| TW | 201208734 A | 3/2012 |
| WO | WO9312742 | 7/1993 |
| WO | WO9524159 | 9/1995 |
| WO | WO9625888 | 8/1996 |
| WO | WO9634568 | 11/1996 |
| WO | WO9639079 | 12/1996 |
| WO | WO9735518 | 10/1997 |
| WO | WO9832379 | 7/1998 |
| WO | WO9852465 | 11/1998 |
| WO | WO9933520 | 7/1999 |
| WO | WO9939677 | 8/1999 |
| WO | WO9949788 | 10/1999 |
| WO | WO200006032 | 2/2000 |
| WO | WO0015300 | 3/2000 |
| WO | WO0021612 | 4/2000 |
| WO | WO0048518 | 8/2000 |
| WO | WO0053113 | 9/2000 |
| WO | WO200071021 | 11/2000 |
| WO | WO0128623 | 4/2001 |
| WO | WO01045550 | 6/2001 |
| WO | WO0182777 | 11/2001 |
| WO | WO0182778 | 11/2001 |
| WO | WO0187161 | 11/2001 |
| WO | WO01080709 | 11/2001 |

(56) References Cited

FOREIGN PATENT DOCUMENTS

| | | |
|---|---|---|
| WO | WO02/09812 | 2/2002 |
| WO | WO0209813 | 2/2002 |
| WO | WO02015768 | 2/2002 |
| WO | WO0224050 | 3/2002 |
| WO | WO2002054018 | 7/2002 |
| WO | WO2002092168 | 11/2002 |
| WO | WO03053266 | 7/2003 |
| WO | WO03065347 | 8/2003 |
| WO | WO03070105 | 8/2003 |
| WO | WO03077833 | 9/2003 |
| WO | WO03086215 | 10/2003 |
| WO | WO03096883 | 11/2003 |
| WO | WO03099177 | 12/2003 |
| WO | WO03099382 | 12/2003 |
| WO | WO03101530 | 12/2003 |
| WO | WO2004000116 | 12/2003 |
| WO | WO2004080147 | 9/2004 |
| WO | WO2004110558 | 12/2004 |
| WO | WO2005/011804 | 2/2005 |
| WO | WO2005065408 | 7/2005 |
| WO | WO2005065409 | 7/2005 |
| WO | WO2005090978 | 9/2005 |
| WO | WO2005113068 | 12/2005 |
| WO | WO2006/042163 | 4/2006 |
| WO | WO2006036870 | 4/2006 |
| WO | WO2006042168 | 4/2006 |
| WO | WO2006042201 | 4/2006 |
| WO | WO2006065671 | 6/2006 |
| WO | WO2006082573 | 8/2006 |
| WO | WO2006104568 | 10/2006 |
| WO | WO2007067563 | 6/2007 |
| WO | WO2008036479 | 3/2008 |
| WO | WO2008036622 | 3/2008 |
| WO | WO2008144274 | 11/2008 |
| WO | WO2009013729 | 1/2009 |
| WO | WO2009149390 | 10/2009 |
| WO | WO2012134645 | 10/2012 |
| WO | WO2013048912 | 4/2013 |
| WO | WO2013178830 | 12/2013 |
| WO | WO2014045216 | 3/2014 |
| WO | WO2014055708 | 4/2014 |
| WO | WO2014057388 | 4/2014 |
| WO | WO2014127091 | 8/2014 |
| WO | WO2015160708 | 10/2015 |
| WO | WO2016054155 | 4/2016 |
| WO | WO2016115363 | 7/2016 |
| WO | WO2017127328 | 7/2017 |
| WO | WO2017149506 | 9/2017 |
| WO | WO2017165595 | 9/2017 |
| WO | WO 2017/212489 | 12/2017 |
| WO | WO2017212489 | 12/2017 |
| WO | WO2018035012 | 2/2018 |
| WO | WO2018158355 | 9/2018 |
| WO | WO2019008573 | 1/2019 |
| WO | WO 2019147596 | 8/2019 |
| WO | WO2019147596 | 8/2019 |
| WO | WO2019164836 | 8/2019 |
| WO | WO2020009324 | 1/2020 |
| WO | WO2020075906 | 4/2020 |
| WO | WO2020080730 | 4/2020 |
| WO | WO2020121307 | 6/2020 |

OTHER PUBLICATIONS

PCT/US2017/46703 International Search Report dated Jan. 12, 2018, 32 pages.

Agren, Magnus S. et al., Collagenase in Wound Healing: Effect of Wound Age and Type. The Journal of Investigative Dermatology, vol. 99/No. 6, (Dec. 1992).

Alam, M., "The future of noninvasive procedural dermatology". Semin Cutan Med Surg. Mar. 2013; 32(1):59-61.

Alam, M., et al., "Ultrasound tightening of facial and neck skin: a rater-blinded prospective cohort study". J Am Acad Dermatol, 2010. 62(2): p. 262-9.

Alexiades-Armenakas, M., "Ultrasound Technologies for Dermatologic Techniques". J Drugs Derm. 2014. 12 (11): p. 1305.

Alster, T.S., et. al., "Noninvasive lifting of arm, thigh, and knee skin with transcutaneousintense focused ultrasound". Dermatol Surg, 2012. 38(5): p. 754-9.

Alster, Tinas S., Tanzi, Elizabeth L., "Cellulite Treatment using a Novel Combination Radiofrequency, Infrared Light, and Mechanical Tissue Manipulation Device," Journal of Cosmetic & Laser Therapy, Jun. 2005, vol. 7, Issue 2, pp. 81-85.

Arosarena, O., "Options and Challenges for Facial Rejuvenation in Patients With Higher Fitzpatrick Skin Phototypes". JAMA Facial Plastic Surgery, 2015.

Arthur et al., "Non-invasive estimation of hyperthermia temperatures with ultrasound," Int. J. Hyperthermia, Sep. 2005, 21(6), pp. 589-600.

Barthe et al., "Ultrasound therapy system and ablation results utilizing miniature imaging/therapy arrays," Ultrasonics Symposium, 2004 IEEE, Aug. 23, 2004, pp. 1792-1795, vol. 3.

Bozec, Laurent et al., Thermal Denaturation Studies of Collagen by Microthermal Analysis and Atomic Force Microscopy, Biophysical Journal, vol. 101, pp. 228-236. (Jul. 2001).

Brobst, R.W., et al., "Noninvasive Treatment of the Neck". Facial Plast Surg Clin North Am, 2014. 22(2): p. 191-202.

Brobst, R.W., et., al., "Ulthera: initial and six month results". Facial Plast Surg Clin North Am, 2012. 20(2): p. 163-76.

Calderhead et al., "One Mechanism Behind LED Photo-Therapy for Wound Healing and Skin Rejuvenation: Key Role of the Mast Cell" Laser Therapy 17.3: 141-148 (2008).

Casabona, G., et al., "Microfocused Ultrasound With Visualization and Fillers for Increased Neocollagenesis: Clinical and Histological Evaluation". Dermatol Surg 2014;40:S194-S198.

Casabona, G., et al., "Microfocused Ultrasound with Visualization and Calcium Hydroxylapatite for Improving Skin Laxity and Cellulite Appearance"; Plast Reconstr Surg Glob Open. Jul. 25, 2017;5(7):e1388, 8 pages.

Chan, N.P., et al., "Safety study of transcutaneous focused ultrasound for non-invasive skin tightening in Asians". Lasers Surg Med, 2011. 43(5): p. 366-75.

Chapelon et al., "Effects of Cavitation In The High Intensity Therapeutic Ultrasound", Ultrasonics Symposium—1357 (1991).

Chapelon, et al., "Thresholds for Tissue Ablation by Focused Ultrasound" (1990).

Chen, L. et al., "Effect of Blood Perfusion on the ablation of liver parenchyma with high intensity focused ultrasound," Phys. Med. Biol; 38:1661-1673; 1993b.

Coon, Joshua et al., "Protein identification using sequential ion/ion reactions and tandem mass spectrometry" Proceedings of the National Academy of Sciences of the USA, vol. 102, No. 27, Jul. 27, 2005, pp. 9463-9468.

Corry, Peter M., et al., "Human Cancer Treatment with Ultrasound", IEEE Transactions on Sonics and Ultrasonics, vol. SU-31, No. 5, Sep. 1984, pp. 444, 456.

Damianou et al., "Application of the Thermal Dose Concept for Predicting the Necrosed Tissue Volume During Ultrasound Surgery," 1993 IEEE Ultrasound Symposium, pp. 1199-1202.

Daum et al., Design and Evaluation of a Feedback Based Phased Array System for Ultrasound Surgery, IEEE Transactions on Ultrasonics, Ferroelectrics, and Frequency Control, vol. 45, No. 2, Mar. 1998, pp. 431-438.

Davis, Brian J., et al., "An Acoustic Phase Shift Technique for the Non-Invasive Measurement of Temperature Changes in Tissues", 1985 Ultrasonics Symposium, pp. 921-924.

Dayan, S.H., et al., "Prospective, Multi-Center, Pivotal Trial Evaluating the Safety and Effectiveness of Micro-Focused Ultrasound with Visualization (MFU-V) for Improvement in Lines and Wrinkles of the Décolletage". Plast Reconstr Surg. Oct. 2014; 134(4 Suppl 1):123-4.

Decision of the Korean Intellectual Property Tribunal dated Jun. 28, 2013 regarding Korean Patent No. 10-1142108, which is related to the pending application and/or an application identified in the Table on pp. 1-4 of the Information Disclosure Statement herein (English translation, English translation certification, and Korean decision included).

(56) References Cited

OTHER PUBLICATIONS

Delon Martin, C., et al, "Venous Thrombosis Generation By Means of High-Intensity Focused Ultrasound" Ultrasound in Med. & Biol., vol. 21, No. 1, pp. 113-119 (1995).
Dierickx, Christine C., "The Role of Deep Heating for Noninvasive Skin Rejuvenation" Lasers in Surgery and Medicine 38:799-807 (2006).
Dobke, M.K., et al., "Tissue restructuring by energy-based surgical tools". Clin Plast Surg, 2012. 39(4): p. 399-408.
Dong, Yuan-Lin et al., "Effect of Ibuprofen on the Inflammatory Response To Surgical Wounds" The Journal of Trauma, vol. 35, No. 3. (1993).
Dvivedi, Sanjay, et al. "Effect of Ibuprofen and diclofenac sodium on experimental wound healing" Indian Journal of Experimental Biology, vol. 35, pp. 1243-1245. (Nov. 1997).
Fabi, S.G., "Microfocused Ultrasound With Visualization for Skin Tightening and Lifting: My Experience and a Review of the Literature". Dermatol Surg. Dec. 2014; 40 Suppl 12:S164-7.
Fabi, S.G., "Noninvasive skin tightening: focus on new ultrasound techniques". Clin Cosmet Investig Dermatol. Feb. 5, 2015; 8:47-52.
Fabi, S.G., et. al., "A prospective multicenter pilot study of the safety and efficacy of microfocused ultrasound with visualization for improving lines and wrinkles of the décolleté". Dermatol Surg. Mar. 2015; 41(3):327-35.
Fabi, S.G., et. al., "Evaluation of microfocused ultrasound with visualization for lifting, tightening, and wrinkle reduction of the decolletage". J Am Acad Dermatol, 2013. 69(6): p. 965-71.
Fabi, S.G., et. al., "Future directions in cutaneous laser surgery". Dermatol Clin, 2014. 32(1): p. 61-9.
Fabi, S.G., et. al., "Retrospective Evaluation of Micro-focused Ultrasound for Lifting and Tightening the Face and Neck". Dermatol Surg, 2014.
Friedmann D.P., "Comments on evaluation of microfocused ultrasound system for improving skin laxity and tightening in the lower face". Aesthet Surg J. Mar. 2015;35(3):NP81-2.
Friedmann, D.P., et. al., "Combination of intense pulsed light, Sculptra, and Ultherapy for treatment of the aging face". J Cosmet Dermatol, 2014. 13(2): p. 109-18.
Fry, W.J. et al., "Production of Focal Destructive Lesions in the Central Nervous System with Ultrasound," J. Neurosurg., 11:471-478; 1954.
Fujimoto, et al., "A New Cavitation Suppression Technique for Local Ablation Using High-Intensity Focused Ultrasound" Ultrasonics Symposium—1629 (1995).
Gliklich et al., Clinical Pilot Study of Intense Ultrasound therapy to Deep Dermal Facial Skin and Subcutaneous Tissues, Arch Facial Plastic Surgery, Mar. 1, 2007, vol. 9, No. 1.
Gold, M.H., et. al., "Use of Micro-Focused Ultrasound with Visualization to Lift and Tighten Lax Knee Skin". J Cosmet Laser Ther, 2014: p. 1-15.
Goldberg, D.J., et. al., "Safety and Efficacy of Microfocused Ultrasound to Lift, Tighten, and Smooth the Buttocks". Dermatol Surg 2014; 40:1113-1117.
Greene, R.M., et al., "Skin tightening technologies". Facial Plast Surg. Feb. 2014; 30(1):62-7.
Greenhalgh, David G., "Wound healing and diabetes mellitus" Clinics in Plastic Surgery 30; 37-45. (2003).
Guo, S. et al., "Factors Affecting Wound Healing" Critical Reviews in Oral Biology & Medicine, J Dent Res 89(3), pp. 219-229. (2010).
Haar, G.R et al., "Tissue Destruction with Focused Ultrasound in Vivo," Eur. Urol. 23 (suppl. 1):8-11; 1993.
Hantash, Basil M. et al., "Bipolar Fractional Radiofrequency Treatment Induces Neoelastogenesis and Neocollagenesis" Lasers in Surgery and Medicine 41:1-9 (2009).
Hantash, Basil M. et al., "In Vivo Histological Evaluation of a Novel Ablative Fractional Resurfacing Device" Lasers in Surgery and Medicine 39:96-107 (2007).
Harris, M.O., "Safety of Microfocused Ultrasound With Visualization in Patients With Fitzpatrick Skin Phototypes III to VI". JAMA Facial Plast. Surg, 2015.

Hart, et. al., "Current Concepts in the Use of PLLA:Clinical Synergy Noted with Combined Use of Microfocused Ultrasound and Poly-I-Lactic Acid on the Face, Neck, and Décolletage". Amer. Soc. Plast. Surg. 2015. 136; 180-187S.
Hassan et al., "Structure and Applications of Poly(vinyl alcohol) Hydrogels Produced by Conventional Crosslinking or by Freezing/Thawing Methods," advanced in Polymer Science, 2000, pp. 37-65, vol. 153.
Hassan et al., "Structure and Morphology of Freeze/Thawed PVA Hydrogels," Macromolecules, Mar. 11, 2000, pp. 2472-2479, vol. 33, No. 7.
Hexsel et al., "A Validated Photonumeric Cellulite Severity Scale"; J Eur Acad Dermatol Venereol. May 2009; 23(5):523-8, 6 pages.
Hitchcock, T.M. et. al., "Review of the safety profile for microfocused ultrasound with Visualization". Journal of Cosmetic Dermatology, 13, 329-335. (2014).
Husseini et al, "The Role of Cavitation in Acoustically Activated Drug Delivery," J. Control Release, Oct. 3, 2005, pp. 253-261, vol. 107(2).
Husseini et al. "Investigating the mechanism of acoustically activated uptake of drugs from Plutonic micelles," BMD Cancer 2002, 2:20k, Aug. 30, 2002, pp. 1-6.
Hynynen et al., Temperature Distributions During Local Ultrasound Induced Hyperthermia In Vivo, Ultrasonics Symposium—745 (1982).
Jeffers et al., "Evaluation of the Effect of Cavitation Activity on Drug-Ultrasound Synergisms," 1993 IEEE Ultrasonics Symposium, pp. 925-928.
Jenne, J., et al., "Temperature Mapping for High Energy US-Therapy", 1994 Ultrasonics Symposium, pp. 1879-1882.
Jeong, K.H., et al., "Neurologic complication associated with intense focused ultrasound". J Cosmet Laser Ther, 2013.
Johnson, S.A., et al., "Non-Intrusive Measurement of Microwave and Ultrasound-Induced Hyperthermia by Acoustic Temperature Tomography", Ultrasonics Symposium Proceedings, pp. 977-982. (1977).
Kim, H.J., et al., "Coagulation and ablation patterns of high-intensity focused ultrasound on a tissue mimicking phantom and cadaveric skin". Laser Med Sci. Sep. 4, 2015.
Kornstein, A.N., "Ulthera for silicone lip correction". Plast Reconstr Surg, 2012. 129(6): p. 1014e-1015e.
Kornstein, A.N., "Ultherapy shrinks nasal skin after rhinoplasty following failure of conservative measures". Plast Reconstr Surg, 2013. 131(4): p. 664e-6e.
Krischak, G.D., et al., "The effects of non-steroidal anti-inflammatory drug application on incisional wound healing in rats" Journal of Wound Care, vol. 6, No. 2, (Feb. 2007).
Laubach, H.J., et. al., "Confined Thermal Damage with Intense Ultrasound (IUS)" [abstr.] American Society for Laser Medicine and Surgery Abstracts, p. 15 #43 (Apr. 2006).
Laubach, H.J., et. al., "Intense focused ultrasound: evaluation of a new treatment modality for precise microcoagulation within the skin". Dermatol Surg, 2008. 34(5): p. 727-34.
Lee, H.J., et. al., "The efficacy and safety of intense focused ultrasound in the treatment of enlarged facial pores in Asian skin". J Dermatolog Treat, 2014.
Lee, H.S., et. al., "Multiple Pass Ultrasound Tightening of Skin Laxity of the Lower Face and Neck". Dermatol Surg, 2011.
Lin, Sung-Jan, et al., "Monitoring the thermally induced structural transitions of collagen by use of second-harmonic generation microscopy" Optics Letters, vol. 30, No. 6, (Mar. 15, 2005).
Macgregor J.L., et. al., "Microfocused Ultrasound for Skin Tightening". Semin Cutan Med Surg 32:18-25. (2013).
Madersbacher, S. et al., "Tissue Ablation in Benign Prostatic Hyperplasia with High Intensity Focused Ultrasound," Dur. Urol., 23 (suppl. 1):39-43; 1993.
Makin et al, "B-Scan Imaging and Thermal Lesion Monitoring Using Miniaturized Dual-Functionality Ultrasound Arrays," Ultrasonics Symposium, 2004 IEEE, Aug. 23, 2004, pp. 1788-1791, vol. 3.
Makin et al, "Confirmed Bulk Ablation and Therapy Monitoring Using Intracorporeal Image-Treat Ultrasound Arrays," 4th International Symposium on Therapeutic Ultrasound, Sep. 19, 2004.

(56) References Cited

OTHER PUBLICATIONS

Makin et al., "Miniaturized Ultrasound Arrays for Interstitial Ablation and Imaging," UltraSound Med. Biol. 2005, Nov. 1, 2005, pp. 1539-1550, vol. 31(11).
Manohar et al, "Photoacoustic mammography laboratory prototype: imaging of breast tissue phantoms," Journal of Biomedical Optics, Nov./Dec. 2004, pp. 1172-1181, vol. 9, No. 6.
Mast et al, "Bulk Ablation of Soft Tissue with Intense Ultrasound; Modeling and Experiments," J. Acoust. Soc. Am., Oct. 1, 2005, pp. 2715-2724, vol. 118(4).
Meshkinpour, Azin, et al., "Treatment of Hypertrophic Scars and Keloids With a Radiofrequency Device: A Study of Collagen Effects" Lasers in Surgery and Medicine 37:343-349 (2005).
Minkis, K., et. al., "Ultrasound skin tightening". Dermatol Clin, 2014. 32(1): p. 71-7.
Mitragotri, S., "Healing sound: the use of ultrasound in drug delivery and other therapeutic applications," Nature Reviews; Drug Delivery, pp. 255-260, vol. 4 (Mar. 2005).
Mosser, David M. et al., "Exploring the full spectrum of macrophage activation" Nat Rev Immunol; 8(12): 958-969. (Dec. 2008).
Murota, Sei-Itsu, et al., "Stimulatory Effect of Prostaglandins on the Production of Hexosamine-Containing Substances by Cultured Fibroblasts (3) Induction of Hyaluronic Acid Synthetase by Prostaglandin" Department of Pharmacology, Tokyo Metropolitan Institute of Gerontology, Itabashiku, Tokyo-173, Japan. (Nov. 1977, vol. 14, No. 5).
Murota, Sei-Itsu, et al., "The Stimulatory Effect of Prostaglandins on Production of Hexosamine-Containing Substances by Cultured Fibroblasts" Department of Pharmacology, Tokyo Metropolitan Institute of Gerontology, Itabashiku, Tokyo-173, Japan. (Aug. 1976, vol. 12, No. 2).
Nestor, M.S. et. al., "Safety and Efficacy of Micro-focused Ultrasound Plus Visualization for the Treatment of Axillary Hyperhidrosis". J Clin Aesthet Dermatol, 2014. 7(4): p. 14-21.
Oni, G., et. al. "Response to 'comments on evaluation of microfocused ultrasound system for improving skin laxity and tightening in the lower face'". Aesthet Surg J. Mar. 2015;35(3):NP83-4.
Oni, G., et. al., "Evaluation of a Microfocused Ultrasound System for Improving Skin Laxity and Tightening in the Lower Face". Aesthet Surg J, 2014. 38:861-868.
Pak, C.S., et. al., "Safety and Efficacy of Ulthera in the Rejuvenation of Aging Lower Eyelids: A Pivotal Clinical Trial". Aesthetic Plast Surg, 2014.
Paradossi et al., "Poly(vinyl alcohol) as versatile biomaterial for potential biomedical applications," Journal of Materials Science: Materials in Medicine, 2003, pp. 687-691, vol. 14.
Pritzker, R.N., et. al, "Updates in noninvasive and minimally invasive skin tightening". Semin Cutan Med Surg. Dec. 2014;33(4):182-7.
Pritzker, R.N., et. al., "Comparison of different technologies for noninvasive skin tightening". Journal of Cosmetic Dermatology, 13, 315-323. (2014).
Rappolee, Daniel A., et al., "Wound Macrophages Express TGF and Other Growth Factors in Vivo: Analysis by mRNA Phenotyping" Science, vol. 241, No. 4866 (Aug. 1988).
Reid, Gavin, et al., "Tandem Mass spectrometry of ribonuclease A and B: N-linked glycosylation site analysis of whole protein ions," Analytical Chemistry. Feb. 1, 2002, vol. 74, No. 3, pp. 577-583.
Righetti et al, "Elastographic Characterization of HIFU-lnduced Lesions in Canine Livers," 1999, Ultrasound in Med & Bio, vol. 25, No. 7, pp. 1099-1113.
Rokhsar, C., et. al., "Safety and efficacy of microfocused ultrasound in tightening of lax elbow skin". Dermatol Surg. 2015; 41(7):821-6.
Rosenberg, Carol S. "Wound Healing in the Patient with Diabetes Mellitus" Nursing Clinics of North America, vol. 25, No. 1, (Mar. 1990).
Saad et al., "Ultrasound-Enhanced Effects of Adriamycin Against Murine Tumors," Ultrasound in Med. & Biol. vol. 18, No. 8, pp. 715-723 (1992).
Sabet-Peyman, E.J. et. al., "Complications Using Intense Ultrasound Therapy to TreatDeep Dermal Facial Skin and Subcutaneous Tissues". Dermatol Surg 2014; 40:1108-1112.
Sandulache, Vlad C. et al., "Prostaglandin E2 inhibition of keloid fibroblast migration, contraction, and transforming growth factor (TGF)-B1-induced collagen synthesis" Wound Rep Reg 15 122-133, 2007. (2007).
Sanghvi, N.T., et al., "Transrectal Ablation of Prostate Tissue Using Focused Ultrasound," 1993 Ultrasonics Symposium, IEEE, pp. 1207-1210.
Sasaki, G.H. et. al., "Clinical Efficacy and Safety of Focused-lmage Ultrasonography: A 2-Year Experience". Aesthet Surg J, 2012.
Sasaki, G.H. et. al., "Microfocused Ultrasound for Nonablative Skin and Subdermal Tightening to the Periorbitum and Body Sites: Preliminary Report on Eighty-Two Patients". Journal of Cosmetics, Dermatological Sciences and Applications, 2012, 2, 108-116.
Sassen, Sander, "ATI's R520 architecture, the new king of the hill?" http://www.hardwareanalysis.com/content/article/1813, Sep. 16, 2005, 2 pages.
Seip, Ralf, et al., "Noninvasive Detection of Thermal Effects Due to Highly Focused Ultrasonic Fields," IEEE Symposium, pp. 1229-1232, vol. 2, Oct. 3-Nov. 1993.
Seip, Ralf, et al., "Noninvasive Estimation of Tissue Temperature Response to Heating Fields Using Diagnostic Ultrasound," IEEE Transactions on Biomedical Engineering, vol. 42, No. 8, Aug. 1995, pp. 828-839.
Simon et al., "Applications of Lipid-Coated Microbubble Ultrasonic Contrast to Tumor Therapy," Ultrasound in Med. & Biol. vol. 19, No. 2, pp. 123-125 (1993).
Sklar, L.R., et. al., "Use of transcutaneous ultrasound for lipolysis and skin tightening: a review". Aesthetic Plast Surg, 2014. 38(2): p. 429-41.
Smith, Nadine Barrie, et al., "Non-invasive In Vivo Temperature Mapping of Ultrasound Heating Using Magnetic Resonance Techniques", 1994 Ultrasonics Symposium, pp. 1829-1832, vol. 3.
Suh, D.H., et. al., "A intense-focused ultrasound tightening for the treatment of infraorbital laxity". J Cosmet Laser Ther, 2012. 14(6): p. 290-5.
Suh, D.H., et. al., "Comparative histometric analysis of the effects of high-intensity focused ultrasound and radiofrequency on skin". J Cosmet Laser Ther. Mar. 24, 2015:1-7.
Suh, D.H., et. al., "Intense Focused Ultrasound Tightening in Asian Skin: Clinical and Pathologic Results" American Society for Dermatologic Surgery, Inc.; 37:1595-1602. (2011).
Surry et al., "Poly(vinyl alcohol) cryogel phantoms for use in ultrasound and MR imaging," Phys. Med. Biol., Dec. 6, 2004, pp. 5529-5546, vol. 49.
Syka J. E. P. et al., "Peptide and Protein Sequence Analysis by Electron Transfer Dissociation Mass Spectrometry," Proceedings of the National Academy of Sciences of USA, National Academy of Science, Washington, DC, vol. 101, No. 26, Jun. 29, 2004, pp. 9528-9533.
Talbert, D. G., "An Add-On Modification for Linear Array Real-Time Ultrasound Scanners to Produce 3D Displays," UTS Int'l 1977 Brighton, England (Jun. 28-30, 1977) pp. 57-67.
Tata et al., "Interaction of Ultrasound and Model Membrane Systems: Analyses and Predictions," American Chemical Society, Phys. Chem. 1992, 96, pp. 3548-3555.
Ueno, S., et al., "Ultrasound Thermometry in Hyperthermia", 1990 Ultrasonic Symposium, pp. 1645-1652.
Verhofstad, Michiel H.J. et al., "Collagen Synthesis in rat skin and ileum fibroblasts is affected differently by diabetes-related factors" Int. J. Exp. Path. (1998), 79, 321-328.
Wang, H., et al., "Limits on Focused Ultrasound for Deep Hyperthermia", 1994 Ultrasonic Symposium, Nov. 1-4, 1994, pp. 1869-1872, vol. 3.
Wasson, Scott, "NVIDIA's GeForce 7800 GTX graphics processor Power MADD," http://techreport.com/reviews/2005q2/geforce-7800gtx/index.x?pg=1, Jun. 22, 2005, 4 pages.
Weiss, M., "Commentary: noninvasive skin tightening: ultrasound and other technologies: where are we in 2011?" Dermatol Surg, 2012. 38(1): p. 28-30.

(56) References Cited

OTHER PUBLICATIONS

White et al. "Selective Creating of Thermal Injury Zones in the Superficial Musculoaponeurotic System Using Intense Ultrasound Therapy," Arch Facial Plastic Surgery, Jan./Feb. 2007, vol. 9, No. 1 (pp. 22-29).

White, W. M., et al., "Selective Transcutaneous Delivery of Energy to Facial Subdermal Tissues Using the Ultrasound Therapy System" [abstr]. American Society for Laser Medicine and Surgery Abstracts, p. 37 #113 (Apr. 2006).

White, W. Matthew, et al., "Selective Transcutaneous Delivery of Energy to Porcine Soft Tissues Using Intense Ultrasound (IUS)" Lasers in Surgery and Medicine 40:67-75 (2008).

Woodward, J.A., et. al. "Safety and Efficacy of Combining Microfocused Ultrasound With Fractional CO2 Laser Resurfacing for Lifting and Tightening the Face and Neck". Dermatol Surg, Dec. 2014 40:S190-S193.

Zelickson, Brian D. et al., "Histological and Ultrastructural Evaluation of the Effects of a Radiofrequency-Based Nonablative Dermal Remodeling Device, A Pilot Study" Arch Dermatol, vol. 140, (Feb. 2004).

Ulthera, Inc., Petition for Inter Partes Review filed Jul. 19, 2016 in Re U.S. Pat. No. 6,113,559; IPR2016-01459; 63 pages (Filed Jul. 19, 2016).

ULTHERA Exhibit 1001, U.S. Pat. No. 6,113,559 to Klopotek, filed Jul. 19, 2016 in re IPR2016-01459.

ULTHERA Exhibit 1002, Patent file history of U.S. Pat. No. 6,113,559 Klopotek filed Jul. 19, 2016 in re IPR2016-01459.

ULTHERA Exhibit 1003, Declaration of Expert Witness Mark E. Schafer, Ph.D. filed Jul. 19, 2016 in re IPR2016-01459.

ULTHERA Exhibit 1004, Curriculum Vitae of Mark E. Schafer, Ph.D. filed Jul. 19, 2016 in re IPR2016-01459.

ULTHERA Exhibit 1005, International PCT Publication WO96/34568 Knowlton filed Jul. 19, 2016 in re IPR2016-01459.

ULTHERA Exhibit 1006, French Patent No. 2,672,486, Technomed patent filed Jul. 19, 2016 in re IPR2016-01459.

ULTHERA Exhibit 1007, English translation of French Patent No. 2,672,486, Technomed filed Jul. 19, 2016 in re IPR2016-01459.

ULTHERA Exhibit 1008, International PCT Publication WO93/12742, Technomed PCT filed Jul. 19, 2016 in re IPR2016-01459.

ULTHERA Exhibit 1009, English translation of International PCT Publication WO93/12742, Technomed PCT filed Jul. 19, 2016 in re IPR2016-01459.

ULTHERA Exhibit 1010, U.S. Pat. No. 5,601,526, which claims priority to Technomed PCT filed Jul. 19, 2016 in re IPR2016-01459.

ULTHERA Exhibit 1011, Patent file history for European Patent Application No. 98964890.2, Klopotek filed Jul. 19, 2016 in re IPR2016-01459.

ULTHERA Exhibit 1012, Translator Declaration filed Jul. 19, 2016 in re IPR2016-01459.

ULTHERA Exhibit 1013, U.S. Pat. No. 5,230,334 to Klopotek filed Jul. 19, 2016 in re IPR2016-01459.

ULTHERA Exhibit 1014, U.S. Pat. No. 5,755,753 to Knowlton filed Jul. 19, 2016 in re IPR2016-01459.

ULTHERA Exhibit 1015, Excerpts from The American Medical Association Encyclopedia of Medicine (1989) filed Jul. 19, 2016 in re IPR2016-01459.

ULTHERA Exhibit 1016, The Simultaneous Study of Light Emissions and Shock Waves Produced by Cavitation Bubbles, G. Gimenez, J. Acoust. Soc. Am. 71(4), Apr. 1982, pp. 839-847 (filed Jul. 19, 2016 in re IPR2016-01459).

ULTHERA Exhibit 1017, Excerpts from Gray's Anatomy (1995) (filed Jul. 19, 2016 in re IPR2016-01459).

ULTHERA Exhibit 1018, Anatomy of the Superficial Venous System, Comjen G.M., Dermatol. Surg., 1995; 21:35-45 (filed Jul. 19, 2016 in re IPR2016-01459).

ULTHERA Exhibit 1019, Section 2.6 from Ultrasonics Theory and Application, by G.L. Gooberman (Hart Publishing Co., 1969) (filed Jul. 19, 2016 in re IPR2016-01459).

ULTHERA Exhibit 1020, Deep Local Hyperthermia for Cancer Therapy: External Electromagnetic and Ultrasound Techniques, A.Y. Cheung and A. Neyzari, Cancer Research (Suppl.), vol. 44, pp. 4736-4744 (1984) (filed Jul. 19, 2016 in re IPR2016-01459).

Decision on Institution of Inter Partes Review in Re U.S. Pat. No. 6,113,559; IPR2016-01459; 20 pages [011] (Dated Jan. 23, 2017).

DERMAFOCUS Response to Institution of Inter Partes Review in Re U.S. Pat. No. 6,113,559; IPR2016-01459; 73 pages [018] (Dated Apr. 26, 2017).

DERMAFOCUS Exhibit List in Re U.S. Pat. No. 6,113,559; IPR2016-01459; 5 pages [019] (Dated Apr. 26, 2017).

DERMAFOCUS Exhibit 2002, Declaration of Mark Palmeri, in Re U.S. Pat. No. 6,113,559; IPR2016-01459; 136 pages (Filed Apr. 26, 2017).

DERMAFOCUS Exhibit 2003, Deposition of Dr. Mark Schafer, in Re U.S. Pat. No. 6,113,559; IPR2016-01459; 327 pages (Filed Apr. 26, 2017).

DERMAFOCUS Exhibit 2004, Amendment No. 4 to Ulthera Form S-1, in Re U.S. Pat. No. 6,113,559; IPR2016-01459; 308 pages (Filed Apr. 26, 2017).

DERMAFOCUS Exhibit 2005, Excerpt from Churchill Livingstone, Gray's Anatomy (38th ed. 1995), in Re U.S. Pat. No. 6,113,559; IPR2016-01459; 7 pages (Filed Apr. 26, 2017).

DERMAFOCUS Exhibit 2006, Bo Eklof et al., "Revision of the CEAP Classification for Chronic Venous Disorders: Consensus Statement," ACTA FAC MED NAISS, vol. 25, No. 1 (2008), 3-10 in Re U.S. Pat. No. 6,113,559; IPR2016-01459; 7 pages (Filed Apr. 26, 2017).

DERMAFOCUS Exhibit 2007, WebMD, "Varicose Veins and Spider Veins" downloaded from http://www.webmd.com/skin-problems-andtreatments/guide/varicose-spider-veins#1 in Re U.S. Pat. No. 6,113,559; IPR2016-01459; 3 pages (Filed Apr. 26, 2017).

DERMAFOCUS Exhibit 2008, John M. Porter et al, "Reporting Standards in Venous Disease: An Update," Journal of Vascular Surgery, vol. 21, No. 4 (1995), 635-645 in Re U.S. Pat. No. 6,113,559; IPR2016-01459; 11 pages (Filed Apr. 26, 2017).

DERMAFOCUS Exhibit 2009, Kullervo Hynynen, "Review of Ultrasound Therapy," 1997 Ultrasonics Symposium (1997), 1305-1313, in Re U.S. Pat. No. 6,113,559; IPR2016-01459; 9 pages (Filed Apr. 26, 2017).

DERMAFOCUS Exhibit 2010, A.G. Visioli et al, "Preliminary Results of a Phase I Dose Escalation Clinical Trial Using Focused Ultrasound in the Treatment of Localised Tumours," European Journal of Ultrasound, vol. 9 (1999), 11-18, in Re U.S. Pat. No. 6,113,559; IPR2016-01459; 8 pages (Filed Apr. 26, 2017).

DERMAFOCUS Exhibit 2011, U.S. Pat. No. 5,143,063, issued on Sep. 1, 1992, Fellner, in Re U.S. Pat. No. 6,113,559; IPR2016-01459; 6 pages (Filed Apr. 26, 2017).

DERMAFOCUS Exhibit 2012, Hugh G. Beebe et al, "Consensus Statement: Classification and Grading of Chronic Venous Disease in the Lower Limbs," European Journal of Vascular and Endovascular Surgery, vol. 12 (1996), 487-492, in Re U.S. Pat. No. 6,113,559; IPR2016-01459; 6 pages (Filed Apr. 26, 2017).

DERMAFOCUS Exhibit 2013, Excerpt from Mosby's Medical Dictionary (3rd ed. 1990), in Re U.S. Pat. No. 6,113,559; IPR2016-01459; 4 pages (Filed Apr. 26, 2017).

DERMAFOCUS Exhibit 2014, Excerpt from Miller-Keane Encyclopedia & Dictionary of Medicine, Nursing, & Allied Health (5th ed. 1992), in Re U.S. Pat. No. 6,113,559; IPR2016-01459; 6 pages (Filed Apr. 26, 2017).

DERMAFOCUS Exhibit 2015, David J. Tibbs et al, Varicose Veins, Venous Disorders, and Lymphatic Problems in the Lower Limbs (1997), Chapter 4: Clinical Patterns of Venous Disorder I, 47-67, in Re U.S. Pat. No. 6,113,559; IPR2016-01459; 24 pages (Filed Apr. 26, 2017).

DERMAFOCUS Exhibit 2016, Mitchel P. Goldman et al, Varicose Veins and Telangiectasias (2nd ed. 1999), Chapter 22: Treatment of Leg Telangiectasias with Laser and High-Intensity Pulsed Light, 470-497, in Re U.S. Pat. No. 6,113,559; IPR2016-01459; 31 pages (Filed Apr. 26, 2017).

DERMAFOCUS Exhibit 2017, Email from Anderson to Klopotek dated May 25, 2004, in Re U.S. Pat. No. 6,113,559; IPR2016-01459; 1 page (Filed Apr. 26, 2017).

(56) References Cited

OTHER PUBLICATIONS

DERMAFOCUS Exhibit 2018, List of Klopotek Patents, in Re U.S. Pat. No. 6,113,559; IPR2016-01459; 411 pages (Filed Apr. 26, 2017).
DERMAFOCUS Exhibit 2019, Declaration of Peter Klopotek Civil Action 15-cv-654-SLR, dated Nov. 2, 2016, in Re U.S. Pat. No. 6,113,559; IPR2016-01459; 1 page (Filed Apr. 26, 2017).
DERMAFOCUS Exhibit 2020, "Our Technology," downloaded from http://jobs.ulthera.com/about on Apr. 10, 2017, in Re U.S. Pat. No. 6,113,559; IPR2016-01459; 4 pages (Filed Apr. 26, 2017).
DERMAFOCUS Exhibit 2021, C. Damianou and K. Hynynen, "Focal Spacing and Near-Field Heating During Pulsed High Temperature Ultrasound Therapy," Ultrasound in Medicine & Biology, vol. 19, No. 9 (1993), 777-787, in Re U.S. Pat. No. 6,113,559; IPR2016-01459; 11 pages (Filed Apr. 26, 2017).
DERMAFOCUS Exhibit 2022, Excerpt from Mosby's Medical Dictionary (5th ed. 1997), in Re U.S. Pat. No. 6,113,559; IPR2016-01459; 5 pages (Filed Apr. 26, 2017).
DERMAFOCUS Exhibit 2023, Excerpt from Miller-Keane Encyclopedia & Dictionary of Medicine, Nursing, & Allied Health (6th ed. 1997), in Re U.S. Pat. No. 6,113,559; IPR2016-01459; 7 pages (Filed Apr. 26, 2017).
DERMAFOCUS Exhibit 2024, Excerpt from Stedman's Concise Medical Dictionary (3 rd ed. 1997), in Re U.S. Pat. No. 6,113,559; IPR2016-01459; 4 pages (Filed Apr. 26, 2017).
DERMAFOCUS Exhibit 2025, Excerpt from Taber's Cyclopedic Medical Dictionary (18th ed. 1997), in Re U.S. Pat. No. 6,113,559; IPR2016-01459; 9 pages (Filed Apr. 26, 2017).
DERMAFOCUS Exhibit 2026, Bo Eklof et al, "Revision of the CEAP Classification for Chronic Venous Disorders: Consensus Statement," Journal ofVascular Surgery, vol. 40, No. 6 (2004), 1248-1252.el, in Re U.S. Pat. No. 6,113,559; IPR2016-01459; 6 pages (Filed Apr. 26, 2017).
Ulthera, Inc., Reply in Support of Petition for Inter Partes Review in Re U.S. Pat. No. 6,113,559; IPR2016-01459; 33 pages (Filed Aug. 2, 2017).
ULTHERA Exhibit 1022, Use of the Argon and Carbon Dioxide Lasers for Treatment of Superficial Venous Varicosities of the Lower Extremity, D. Apfelberg et al., Lasers in Surgery and Medicine, vol. 4.3, pp. 221-231 (1984) (filed Aug. 2, 2017 in re IPR2016-01459).
ULTHERA Exhibit 1023, 532-Nanometer Green Laser Beam Treatment of Superficial Varicosities of the Lower Extremities, T. Smith et al., Lasers in Surgery and Medicine, vol. 8.2, pp. 130-134 (1988) (filed Aug. 2, 2017 in re IPR2016-01459).
ULTHERA Exhibit 1024, Deposition Transcript of Dr. Mark Palmeri on Jul. 11, 2017 (filed Aug. 2, 2017 in re IPR2016-01459).
ULTHERA Exhibit 1025, Ulthera Oral Proceeding Demonstrative Slides (filed Oct. 2, 2017 in re IPR2016-01459).
DERMAFOCUS Exhibit 2027, DermaFocus Oral Proceeding Demonstrative Slides (filed Oct. 2, 2017 in re IPR2016-01459).
PTAB Record of Oral Hearing held Oct. 4, 2017 in Re U.S. Pat. No. 6,113,559; IPR2016-01459; 67 pages (PTAB Document sent to Ulthera on Nov. 1, 2017).
Final Written Decision of Inter Partes Review in Re U.S. Pat. No. 6,113,559; IPR2016-01459; 37 pages [030] (Entered Jan. 19, 2018).
Adams et al., "High Intensity Focused Ultrasound Ablation of Rabbit Kidney Tumors" Sonablate High-Intensity Focused Ultrasound device; Journal of Endourology vol. 10, No. 1, (Feb. 1996).
Brown J A et al: "Fabrication and performance of 40-60 MHz annular arrays", 2003 IEEE Ultrasonics Symposium Proceedings. Honolulu, Hawaii, Oct. 5-8, 2003; [IEEE Ultrasonics Symposium Proceedings], New York, NY : IEEE, US, vol. 1, Oct. 5, 2003 (Oct. 5, 2003), pp. 869-872.
Carruthers et al., "Consensus Recommendations for Combined Aesthetic Interventions in the Face Using Botulinum Toxin, Fillers,and Energy-Based Devices" Dermatol Surg 2016 (pp. 1-12).
Driller et al., "Therapeutic Applications of Ultrasound: A Review" IEEE Engineering in Medicine and Biology; (Dec. 1987) pp. 33-40.
Ketterling J. A. et al.: "Design and fabrication of a 40-MHz annular array transducer", IEEE Transactions On Ultrasonics, Ferroelectrics And Frequency Control, IEEE, US, vol. 52, No. 4, Apr. 1, 2005 (Apr. 1, 2005), pp. 672-681.
MICROCHIP microID 125 kHz EFID System Design Guide, Microchip Technology Inc. (2004).
Sonocare, Inc. Therapeutic Ultrasound System Model CST-100 Instruction Manual (1985).
Webster et al. "The role of ultrasound-induced cavitation in the 'in vitro' stimulation of collagen synthesis in human fibroblasts"; Ultrasonics pp. 33-37(Jan. 1980).
Ulthera, Inc., Petitioner Notice of Appeal to Federal Circuit 2018-1542 re: IPR2016-01459; 4 pages from [001] (no appendices) (Filed Feb. 9, 2018).
Federal Circuit Order Granting Ulthera Motion to Remand, re: 2018-1542; 4 pages [022] (Dated May 25, 2018).
Ulthera Brief (Corrected), Fed. Cir. Appeal Case 19-1006 from re: IPR2016-01459; 136 pages [030] (Dated Apr. 3, 2019).
DermaFocus Brief (Corrected), Fed. Cir. Appeal Case 19-1006 from re: IPR2016-01459; 73 pages [032] (Dated Apr. 4, 2019).

\* cited by examiner

TABLE 4

| f [MHz] | $k_x = 0.5$ mm$^{-1}$ | | $k_x = 1.0$ mm$^{-1}$ | | $k_x = 1.5$ mm$^{-1}$ | | $k_x = 2.0$ mm$^{-1}$ | |
|---|---|---|---|---|---|---|---|---|
| | spacing [mm] | spread [mm] | spacing [mm] | spread [mm] | spacing [mm] | spread [mm] | spacing [mm] | spread [mm] |
| 2.5 | 1.43 | 0.72 | 2.86 | 1.43 | 4.30 | 2.15 | 5.73 | 2.86 |
| 2.75 | 1.30 | 0.59 | 2.60 | 1.17 | 3.91 | 1.76 | 5.21 | 2.34 |
| 3 | 1.19 | 0.48 | 2.39 | 0.95 | 3.58 | 1.43 | 4.77 | 1.91 |
| 3.25 | 1.10 | 0.39 | 2.20 | 0.77 | 3.31 | 1.16 | 4.41 | 1.54 |
| 3.5 | 1.02 | 0.31 | 2.05 | 0.61 | 3.07 | 0.92 | 4.09 | 1.23 |
| 3.75 | 0.95 | 0.24 | 1.91 | 0.48 | 2.86 | 0.72 | 3.82 | 0.95 |
| 4 | 0.90 | 0.18 | 1.79 | 0.36 | 2.69 | 0.54 | 3.58 | 0.72 |
| 4.25 | 0.84 | 0.13 | 1.69 | 0.25 | 2.53 | 0.38 | 3.37 | 0.51 |
| 4.5 | 0.80 | 0.08 | 1.59 | 0.16 | 2.39 | 0.24 | 3.18 | 0.32 |
| 4.75 | 0.75 | 0.04 | 1.51 | 0.08 | 2.26 | 0.11 | 3.02 | 0.15 |
| 5 | 0.72 | 0.00 | 1.43 | 0.00 | 2.15 | 0.00 | 2.86 | 0.00 |
| 5.25 | 0.68 | -0.03 | 1.36 | -0.07 | 2.05 | -0.10 | 2.73 | -0.14 |
| 5.5 | 0.65 | -0.07 | 1.30 | -0.13 | 1.95 | -0.20 | 2.60 | -0.26 |
| 5.75 | 0.62 | -0.09 | 1.25 | -0.19 | 1.87 | -0.28 | 2.49 | -0.37 |
| 6 | 0.60 | -0.12 | 1.19 | -0.24 | 1.79 | -0.36 | 2.39 | -0.48 |
| 6.25 | 0.57 | -0.14 | 1.15 | -0.29 | 1.72 | -0.43 | 2.29 | -0.57 |
| 6.5 | 0.55 | -0.17 | 1.10 | -0.33 | 1.65 | -0.50 | 2.20 | -0.66 |
| 6.75 | 0.53 | -0.19 | 1.06 | -0.37 | 1.59 | -0.56 | 2.12 | -0.74 |
| 7 | 0.51 | -0.20 | 1.02 | -0.41 | 1.53 | -0.61 | 2.05 | -0.82 |
| 7.25 | 0.49 | -0.22 | 0.99 | -0.44 | 1.48 | -0.67 | 1.98 | -0.89 |
| 7.5 | 0.48 | -0.24 | 0.95 | -0.48 | 1.43 | -0.72 | 1.91 | -0.95 |

FIG. 5

Poled Ceramic with Spatial Frequency of $k_x$

| 0 DEGREES | 180 DEGREES | 0 DEGREES | 180 DEGREES | 0 DEGREES | 180 DEGREES | 0 DEGREES | 180 DEGREES |
|---|---|---|---|---|---|---|---|
| Channel 1 / Channel 2 | Channel 3 / Channel 4 | Channel 5 / Channel 6 | Channel 7 / Channel 8 | Channel 9 / Channel 10 | Channel 11 / Channel 12 | Channel 13 / Channel 14 | Channel 15 / Channel 16 |

FIG. 8

Poled Ceramic with Spatial Frequency of $2k_x$

FIG. 9

SYSTEMS AND METHODS FOR COSMETIC ULTRASOUND TREATMENT OF SKIN

CROSS-REFERENCE TO RELATED APPLICATIONS

This application is a U.S. National Phase of PCT Application No. PCT/US2017/046703, filed Aug. 14, 2017, which claims the benefit of priority from U.S. Provisional Application No. 62/375,607 filed Aug. 16, 2016, U.S. Provisional Application No. 62/482,476 filed Apr. 6, 2017, U.S. Provisional Application No. 62/482,440 filed Apr. 6, 2017, and U.S. Provisional Application No. 62/520,055 filed Jun. 15, 2017, each of which is incorporated in its entirety by reference, herein. Any and all priority claims identified in the Application Data Sheet, or any correction thereto, are hereby incorporated by reference under 37 CFR 1.57.

BACKGROUND

Field

Several embodiments of the invention relate to energy-based noninvasive treatments for obtaining aesthetically and/or cosmetically enhancing effects on skin and/or tissue near the skin of a human face, head, neck, and/or body.

Description of the Related Art

Some cosmetic procedures involve invasive procedures that may require invasive surgery. Patients not only have to endure weeks of recovery time, but also are frequently required to undergo risky anesthetic procedures. Non-invasive energy-based therapeutic devices and methods are available, but may have various shortcomings with respect to efficiency and effectiveness. Some cosmetic procedures create a sequential series of treatment points or lines. In those procedures, the period of time for treatment is the sum of the sequential treatments.

SUMMARY

In several embodiments, provided are systems and methods that successfully achieve an aesthetic effect using targeted and precise ultrasound to cause a visible and effective cosmetic result via a thermal pathway by splitting an ultrasound therapy beam to two, three, four, or more simultaneous focal zones for performing various treatment and/or imaging procedures. In various embodiments, an ultrasound system is configured for focusing ultrasound to produce localized, mechanical motion within tissues and cells for the purpose of producing either localized heating for tissue coagulation or for mechanical cellular membrane disruption intended for non-invasive aesthetic use. In various embodiments, an ultrasound system is configured for lifting a brow (e.g., an eyebrow). In various embodiments, an ultrasound system is configured for lifting lift lax tissue, such as submental (beneath the chin) and neck tissue. In various embodiments, an ultrasound system is configured for improving lines and wrinkles of the décolleté. In various embodiments, an ultrasound system is configured for reducing fat. In various embodiments, an ultrasound system is configured for reducing the appearance of cellulite.

In various embodiments, an ultrasound system is configured for imaging to visualize tissue (e.g., dermal and subdermal layers of tissue) to ensure proper coupling of the transducer to the skin. In various embodiments, an ultrasound system is configured for imaging to visualize tissue (e.g., dermal and subdermal layers of tissue) to confirm appropriate depth of treatment such as to avoid certain tissues (e.g., bone).

In various embodiments, treating tissue, such as skin tissue, with multiple beams provides one or more advantages, such as, for example, reducing treatment time, creating unique heating patterns, leveraging multiple channels for greater power, the option to treat skin at two or more depths with the same or different power levels, (e.g., a thermal coagulation point in the superficial muscular aponeurotic system ("SMAS") and another defocused energy at the surface of the skin, or other combinations), optional simultaneous treatment at different depths (e.g., such as at depths below a skin surface of 3 mm and 4.5 mm thermal coagulation points simultaneously or in an overlapping time period); and/or treatment with one, two, or more simultaneous linear or line focuses, such as at different depths below the skin surface or spaced apart. In some embodiments simultaneous multi-focus therapy uses dithering.

In several embodiments, provided are systems and methods that successfully improve the effectiveness and/or efficiency of an aesthetic effect using targeted and precise ultrasound to cause a visible and effective cosmetic result via a thermal pathway. In some embodiments, a single focal zone targeted. In some embodiments an ultrasound therapy beam is split into two, three, four, or more simultaneous focal zones for performing various treatment and/or imaging procedures. In particular, embodiments of the invention improve effectiveness and/or efficiency in confirming the proper coupling between the treatment device and tissue for treatment in a treatment zone.

In several embodiments, provided are systems and methods that successfully improve the effectiveness and/or efficiency of an aesthetic effect using targeted and precise ultrasound to cause a visible and effective cosmetic result via a thermal pathway by splitting an ultrasound therapy beam to two, three, four, or more simultaneous focal zones for performing various treatment and/or imaging procedures.

According to one embodiment, an ultrasound treatment system creates two or more simultaneous therapeutic treatment points and/or focal zones under the skin surface for a cosmetic treatment, wherein the treatment points are enlarged by dithering the ultrasound beams. In one embodiment, a focal zone is a point. In one embodiment, a focal zone is a line. In one embodiment, a focal zone is a plane. In one embodiment, a focal zone is a three-dimensional volume or shape. The dithering of the ultrasound beam focus points enlarges the treatment area by shaking, blurring, or splattering the focus point or focus zone (e.g., a focus point, line, plane, or volume) like paint through an air brush by mechanically and/or electronically scattering the location of the focus points by varying the frequency, and therefore focal point, of the ultrasound treatment beams. In some embodiments, dithering increases efficacy by making a larger treatment points and/or focal zones. In some embodiments, dithering reduces pain since the temperature of the hot spot is spread over a larger volume of tissue, allowing a potential reduction in dose. In some embodiments, mechanical dithering is one method of spreading the acoustic energy from the ultrasound beam so there is less reliance on tissue thermal conduction away from the focus. In one embodiment of mechanical dithering, the therapy transducer is moved locally around the intended center of the thermal coagulation point (TCP). The acoustic beam movement can be side-to-side, up-down, and/or angular. In one embodiment of mechanical dithering, the movement of the motion mechanism is sufficiently fast enough to create a flatter temperature profile around the intended TCP which either allows a reduction of total acoustic energy for the same effected tissue volume or the same total acoustic energy for a larger effected tissue volume or any combination thereof.

In accordance with various embodiments, frequency modulation modifies the location of a focal zone and/or spacing between the focal zones, such that electronic dithering of beam via modulation of the frequency precisely alters and/or moves the position of the beam focus point(s). For example, in one embodiment, a spacing of 1.5 mm can be dithered with +/−0.1 mm using a small frequency swing. In various embodiments, any one or more spacings of 0.5, 0.75, 1.0, 1.2, 1.5, 2.0 mm can be dithered with +/−0.01, 0.05, 0.1, 0.12, 0.15, 0.20, 0.25, 0.30 mm using a frequency swing. In various embodiments, a frequency is modulated by 1-200% (e.g., 1%, 5%, 10%, 15%, 20%, 25%, 30%, 35%, 40%, 45%, 50%. 100%, 120%, 150%, 180%, 200% and any range therein).

Several embodiments relate to devices, systems and methods for providing one or more (e.g., a plurality or multiple) focus zones and/or ultrasound treatment points in performing various ultrasound treatment and/or imaging procedures quickly, safely, efficiently, and effectively. In some embodiments, no imaging is used. Some embodiments relate to splitting an ultrasound therapy beam to two, three, four, or more focal zones from a single ultrasound transducer and/or single ultrasound transduction element. In some embodiments, multiple ultrasound beams are electronically manipulated with frequency modulation. In some embodiments, dithering (e.g., electronic dithering) of multiple and/or split ultrasound beam apertures using frequency modulation provide treatment zones or points in multiple locations. In some embodiments, dithering relates to intentional movement of the position/location of a focal point of an energy beam. For example, in one embodiment, dithering involves shaking, moving, vibrating, altering the location and/or position of a single focal zone, and/or a relative spacing between two or more focal zones. In various embodiments, the relative position of a focal zones is dithered by 1-50% (e.g., 1%, 5%, 10%, 15%, 20%, 25%, 30%, 35%, 40%, 45%, 50% and any range therein, such as a percentage of a mean location by a certain percentage). In various embodiments, spacing between focal zones is dithered by a range of between 1-50% (e.g., 1%, 5%, 10%, 15%, 20%, 25%, 30%, 35%, 40%, 45%, 50% and any range therein). In some embodiments, dithering may be achieved through mechanical, electronic, or combinations of mechanical and electronic means depending on the system design. In one embodiment of mechanical dithering, the ultrasound beam is moved locally around the intended TCP center through a mechanical translation or tilt of the therapy transducer or patient or any combination thereof. The mechanical translation and/or tilt enable(s) the spread of the acoustic energy such that thermal conduction limitations of tissue are overcome. This creates a flatter temperature profile in tissue to either reduce the total acoustic energy to create the same effected tissue volume or have the same total acoustic energy to increase the effected tissue volume when compared to a stationary ultrasound therapy device. In various embodiments of electronic dithering, frequency, phase, amplitude modulations or time based techniques are used to in combination with a uniquely defined transducer to move the ultrasound beam in tissue without any mechanical movement. In one embodiment, electronic movement of the ultrasound beam occurs significantly faster than mechanical movement to overcome the thermal conductivity limitation of tissue. In various embodiments, a ratio of relative focal zone positioning via dithering is 1:1000, 1:500, 1:200; 1:100, 1:50, 1:25, 1:10, 1:2 or any ratio between 1:1000 and 1:1. In various embodiments, a ratio of spacing between relative focal zone positioning via dithering is 1:1000, 1:500, 1:200; 1:100, 1:50, 1:25, 1:10, 1:2 or any ratio between 1:1000 and 1:1. For example, in some embodiments, a focal zone is activated at "1" and an open spacing ratio of untreated tissue is provided in the second number of the ratio. For example, in one embodiment, a dithering spacing is e.g., 1 mm, and a dithering distance is 0.1 mm, so a ratio is 1:10. In various embodiments, a ratio of spacing between focal zones via dithering is 1:1000, 1:500, 1:200; 1:100, 1:50, 1:25, 1:10, 1:2 or any ratio between 1:1000 and 1:1. In some embodiments, the spacing of simultaneous focal zones is dithered. In some embodiments, the treatment points and/or zones are formed simultaneously in tissue. In various embodiments, dithering for performing various treatment and/or imaging procedures is with modulated and/or multiphased with controlled variance in frequency. Some embodiments relate to splitting an ultrasound therapy beam to two, three, four, or more focal zones for performing various treatment with, for example, dithering, poling, phasing, and/or modulation techniques and/or imaging procedures.

In several embodiments disclosed herein, non-invasive ultrasound systems are adapted to be used in achieving one or more of the following beneficial aesthetic and/or cosmetic improvement effects: a face lift, a brow lift, a chin lift, an eye treatment (e.g., malar bags, treat infraorbital laxity), a wrinkle reduction, fat reduction (e.g., treatment of adipose and/or cellulite), cellulite (which may be called gynoid lipodystrophy) treatment (e.g., dimple or non-dimple type female gynoid lipodystrophy), décolletage improvement (e.g., upper chest), a buttock lift (e.g., buttock tightening), skin tightening (for example, treating laxity to cause tightening on the face or body, such as the face, neck, chest, arms, thighs, abdomen, buttocks, etc.), a scar reduction, a burn treatment, a tattoo removal, a vein removal, a vein reduction, a treatment on a sweat gland, a treatment of hyperhidrosis, a sun spot removal, an acne treatment, a pimple reduction. Several embodiments of the invention are particularly advantageous because they include one, several or all of the following benefits: faster treatment time, (ii) less pain during treatment, (iii) less pain after treatment, (iv) shorter recovery time, (v) more efficient treatment, (vi) higher customer satisfaction, (vii) less energy to complete a treatment, and/or (viii) larger treatment area by dithered focal regions.

In accordance with various embodiments, a cosmetic ultrasound treatment system and/or method can non-invasively produce single or multiple dithered cosmetic treatment zones and/or thermal coagulation points where ultrasound is focused in one or more locations in a region of treatment in tissue under a skin surface, and moved via changes in frequency (e.g., via frequency modulation). Some systems and methods provide cosmetic treatment at different locations in tissue, such as at different depths, heights, widths, and/or positions. In one embodiment, a method and system comprise a multiple depth/height/width transducer system configured for providing ultrasound treatment to one or more region of interest, such as between at least one depth of treatment region of interest, a superficial region of interest, and/or a subcutaneous region of interest. In one embodiment, a method and system comprise a transducer system configured for providing ultrasound treatment to more than one region of interest, such as between at least two points in various locations (e.g. at a fixed or variable depth, height, width, and/or orientation, etc.) in a region of interest in tissue. Some embodiments can split a beam to focus at two, three, four, or more focal points (e.g., multiple focal points, multi-focal points) for cosmetic treatment zones and/or for imaging in a region of interest in tissue. Position and/or dithering of the focal points can be positioned axially, laterally, or otherwise within the tissue. Some embodiments can be configured for spatial control, such as by the location and/or dithering of a focus point, changing the distance from a transducer to a reflecting surface, and/or changing the angles of energy focused or unfocused to the region of interest, and/or configured for temporal control, such as by controlling changes in the frequency, drive amplitude and timing of the transducer. In some embodiments the position and/or dithering of multiple treatment zones or focal points is achieved with poling, phasic poling, biphasic poling, and/or multi-phasic poling. In some embodiments the position of multiple treatment zones or focal points with phasing, such as in one embodiment, electrical phasing. As a result, changes in the location of the treatment region, the number, shape, size and/or volume of treatment zones or lesions in a region of interest, as well as the thermal conditions, can be dynamically controlled over time.

In accordance with various embodiments, a cosmetic ultrasound treatment system and/or method can create multiple cosmetic treatment zones using one or more of frequency modulation, phase modulation, poling, nonlinear acoustics, and/or Fourier transforms to create any spatial periodic pattern with one or multiple ultrasound portions. In one embodiment, a system simultaneously or sequentially delivers single or multiple treatment zones using poling at a ceramic level. In one embodiment, a poling pattern is function of focal depth and frequency, and the use of odd or even functions. In one embodiment, a poling pattern, which can be a combination of odd or even functions, is applied, and based on focal depth and/or frequency. In one embodiment, a process can be used in two or more dimensions to create any spatial periodic pattern. In one embodiment, an ultrasound beam is split axially and laterally to significantly reduce treatment time through the use of nonlinear acoustics and Fourier transforms. In one embodiment, modulation from a system and amplitude modulation from a ceramic or a transducer can be used to place multiple treatments zones in tissue, either sequentially or simultaneously.

In one embodiment, an aesthetic imaging and treatment system includes an ultrasonic probe that includes an ultrasound transducer configured to apply ultrasonic therapy to tissue at a plurality of locations at a focal depth with electronic dithering of multiple energy beam apertures with frequency modulation. In one embodiment, the system includes a control module coupled to the ultrasonic probe for controlling the ultrasound transducer.

In one embodiment, the system includes dithering configured to provide variable spacing between a plurality of individual cosmetic treatment zones. In one embodiment, a sequence of individual cosmetic treatment zones has a treatment spacing in a range from about 0.01 mm to about 25 mm (e.g., 1 mm, 1.5 mm, 2 mm, 2.5 mm, 3 mm, 5 mm, 10 mm, 20 mm and any value ranges therein), with a dithering alteration of the spacing by 1-50% (e.g., 1%, 5%, 10%, 15%, 20%, 25%, 30%, 35%, 40%, 45%, 50% and any range therein). In one embodiment, a sequence of individual cosmetic treatment zones has a treatment spacing in a range from about 0.01 mm to about 100 mm (e.g., 1 mm, 1.5 mm, 2 mm, 2.5 mm, 3 mm, 5 mm, 10 mm, 20 mm, 25 mm, 30 mm, 35 mm, 40 mm, 45, mm, 50 mm, 60 mm, 70 mm, 80 mm, 90 mm, and 100 mm, and any value ranges therein), with a dithering alteration of the spacing by 1-50% (e.g., 1%, 5%, 10%, 15%, 20%, 25%, 30%, 35%, 40%, 45%, 50% and any range therein).

In one embodiment, the system further includes a movement mechanism configured to be programmed to provide constant or variable spacing between the plurality of individual cosmetic treatment zones. In one embodiment, a sequence of individual cosmetic treatment zones has a treatment spacing in a range from about 0.01 mm to about 25 mm (e.g., 0.1, 0.5, 1, 2, 3, 4, 5, 6, 7, 8, 9, 10, 15, 19 mm or any range or value therein). In one embodiment, a sequence of individual cosmetic treatment zones has a treatment spacing in a range from about 0.01 mm to about 100 mm (e.g., 0.1, 0.5, 1, 2, 3, 4, 5, 6, 7, 8, 9, 10, 15, 20, 25, 30, 35, 40, 50, 100 mm or any range or value therein). In one embodiment, treatment zones are provided along a distance of about 25 mm. In one embodiment, treatment zones are provided along a distance of about 50 mm. In various embodiments, treatment zones are provided along a distance of 5 mm to 100 mm (e.g., 10 mm, 20 mm, 25 mm, 35 mm, 50 mm, 75 mm, 100 mm, and any amounts or ranges therein. In various embodiments, treatment zones are provided along a linear and/or curved distance.

For example, in some non-limiting embodiments transducers can be configured for a tissue depth of 0.5 mm, 1.0 mm, 1.5 mm, 2 mm, 3 mm, 4.5 mm, 6 mm, less than 3 mm, between 0.5 mm and 5 mm, between 1.5 mm and 4.5 mm, more than more than 4.5 mm, more than 6 mm, and anywhere in the ranges of 0.1 mm-3 mm, 0.1 mm-4.5 mm, 0.1 mm-25 mm, 0.1 mm-100 mm, and any depths therein (e.g., 6 mm, 10 mm, 13 mm, 15 mm). In several embodiments, tissue is treated at a depth below a skin surface and the skin surface is not impaired. Instead, the therapeutic effect achieved at the depth below the skin surface results in a favorable cosmetic appearance of the skin surface. In other embodiments, the skin surface is treated with ultrasound (e.g., at a depth less than 0.5 mm).

One benefit of a motion mechanism is that it can provide for a more efficient, accurate and precise use of an ultrasound transducer, for imaging and/or therapy purposes. One advantage this type of motion mechanism has over conventional fixed arrays of multiple transducers fixed in space in a housing is that the fixed arrays are a fixed distance apart. In one embodiment, the transducer module is configured to provide an acoustic power of the ultrasonic therapy in a range of between about 1 W to about 100 W (e.g., 3-30 W, 7-30 W, 21-33 W) and a frequency of about 1 MHz to about 10 MHz to thermally heat the tissue to cause coagulation. In one embodiment, the transducer module is configured to provide an acoustic power of the ultrasonic therapy in a range of between about 1 W to about 500 W for peak or average energy, (e.g., 3-30 W, 7-30 W, 21-33 W, 100 W, 220 W, or more) and a frequency of about 1 MHz to about 10 MHz to thermally heat the tissue to cause coagulation. In some embodiments, an instantaneous energy is delivered. In some embodiments, an average energy is delivered. In one embodiment, the acoustic power can be from a range of 1 W to about 100 W in a frequency range from about 1 MHz to about 12 MHz (e.g., 1 MHz, 3 MHz, 4 MHz, 4.5 MHz, 7 MHz, 10 MHz, 2-12 MHz), or from about 10 W to about 50 W at a frequency range from about 3 MHz to about 8 MHz (e.g., 3 MHz, 4 MHz, 4.5 MHz, 7 MHz). In one embodiment, the acoustic power can be from a range of 1 W to about 500 W in a frequency range from about 1 MHz to about 12 MHz (e.g., 1 MHz, 4 MHz, 7 MHz, 10 MHz, 2-12 MHz), or from about 10 W to about 220 W at a frequency range from about 3 MHz to about 8 MHz, or 3 MHz to 10

MHz. In one embodiment, the acoustic power and frequencies are about 40 W at about 4.3 MHz and about 30 W at about 7.5 MHz. An acoustic energy produced by this acoustic power can be between about 0.01 joule ("J") to about 10 J or about 2 J to about 5 J. An acoustic energy produced by this acoustic power can be between about 0.01 J to about 60,000 J (e.g., via bulk heating, for body shaping, submental fat, abdomen and/or flanks, arms, inner thigh, outer thigh, buttocks, abdominal laxity, cellulite), about 10 J or about 2 J to about 5 J. In one embodiment, the acoustic energy is in a range less than about 3 J. In various embodiments, a treatment power is 1 kW/cm$^2$ to 100 kW/cm$^2$, 15 kW/cm$^2$ to 75 kW/cm$^2$, 1 kW/cm$^2$ to 5 kW/cm$^2$, 500 W/cm$^2$ to 10 kW/cm$^2$, 3 kW/cm$^2$ to 10 kW/cm$^2$, 15 kW/cm$^2$ to 50 kW/cm$^2$, 20 kW/cm$^2$ to 40 kW/cm$^2$, and/or 15 kW/cm$^2$ to 35 kW/cm$^2$.

In various embodiments, an ultrasound treatment system for dithering multiple simultaneous focus points from an ultrasound transducer includes an ultrasonic probe and a control module coupled to the ultrasonic probe for controlling the ultrasound transducer. The ultrasonic probe includes an ultrasound transducer with a single transduction element adapted to simultaneously apply ultrasonic therapy to tissue at a plurality of spaced locations at a focal depth. The ultrasound transducer is poled with at least a first poling configuration and a second poling configuration. The control module modifies the spacing between the spaced locations via dithering of a first focal zone and a second focal zone, such that dithering via modulation of a frequency precisely moves a position of a beam focus point at the spaced locations.

In one embodiment, the plurality of locations are positioned in a linear sequence within a cosmetic treatment zone, wherein the spaced locations are separated with a spacing dithered via a frequency swing. In one embodiment, a first set of locations is positioned within a first cosmetic treatment zone and a second set of locations is positioned within a second cosmetic treatment zone, the first zone being different from the second zone. In one embodiment, the ultrasound transducer is adapted to apply ultrasonic therapy using amplitude modulation whereby a plurality of portions of the ultrasound transducer are adapted to emit ultrasonic therapy at a plurality of amplitudes of acoustic intensity, wherein a first amplitude is different than a second amplitude. In one embodiment, at least one portion of the ultrasonic transducer is adapted to emit ultrasonic therapy at two or more amplitudes of acoustic intensity, and wherein the amplitude of ultrasonic therapy emitted by the at least one portion of the piezoelectric varies over time. In one embodiment, the ultrasound transducer comprises piezoelectric material and the plurality of portions of the ultrasound transducer are adapted to create a plurality of corresponding piezoelectric material variations in response to an electric field applied to the ultrasound transducer. In one embodiment, the plurality of piezoelectric material variations comprise at least one of expansion of the piezoelectric material and contraction of the piezoelectric material. In one embodiment, the ultrasound transducer is adapted to apply ultrasonic therapy via phase shifting whereby a plurality of portions of the ultrasound transducer are adapted to emit ultrasonic therapy at a plurality of phases of acoustic intensity, wherein a first phase is different than a second phase. In one embodiment, the plurality of phases comprises discrete phase values. In one embodiment, the ultrasound transducer is adapted to apply ultrasonic therapy using amplitude modulation whereby a plurality of portions of the ultrasound transducer are adapted to emit ultrasonic therapy at a plurality of amplitudes of acoustic intensity, wherein a first amplitude is different than a second amplitude, and apply ultrasonic therapy whereby a plurality of portions of the ultrasound transducer are adapted to emit ultrasonic therapy at a plurality of phases of acoustic intensity, wherein a first phase is different than a second phase. In various embodiments, the ultrasonic treatment is at least one of: a face lift, a brow lift, a chin lift, an eye treatment (e.g., malar bags, treat infraorbital laxity), a wrinkle reduction, a décolletage improvement, a buttock lift, a scar reduction, a burn treatment, a skin tightening (e.g., abdominal laxity treatment or treating laxity in other locations), a blood vessel reduction, a treatment of a sweat gland, a sun spot removal, a fat treatment, and a cellulite treatment. Skin tightening by reducing skin laxity is accomplished in some embodiments to treat subject with excess or loose skin post weight loss, whether such weight loss occurs naturally or is performed surgically.

In various embodiments, an ultrasound treatment system for use in cosmetic treatment for dithering multiple simultaneous focal points from an ultrasound transducer includes an ultrasonic probe including a control module adapted to modify a spacing between a first focal zone and a second focal zone via dithering, a switch operably controlling an ultrasonic treatment function for providing an ultrasonic treatment, and a movement mechanism adapted to direct ultrasonic treatment in at least one pair of simultaneous sequences of individual thermal cosmetic treatment zones, and a transducer module adapted to apply ultrasonic therapy. The transducer module is adapted for both ultrasonic imaging and ultrasonic treatment. The transducer module is adapted for coupling to the ultrasonic probe. The transducer module includes an ultrasound transducer adapted to apply ultrasonic therapy to tissue at a plurality of locations at a focal depth. The transducer module is adapted to be operably coupled to at least one of the switch and the movement mechanism. The control module includes a processor and a display for controlling the transducer module.

In one embodiment, the transducer module is adapted to apply ultrasonic therapy using amplitude modulation whereby a plurality of portions of the transducer module are adapted to emit ultrasonic therapy at a plurality of amplitudes of acoustic intensity, wherein a first amplitude is different than a second amplitude. In one embodiment, the transducer module is adapted to apply ultrasonic therapy whereby a plurality of portions of the transducer module are adapted to emit ultrasonic therapy at a plurality of phases of acoustic intensity, wherein a first phase is different than a second phase.

In various embodiments, an ultrasound treatment system for dithering multi-focus treatment includes a module comprising an ultrasound transducer. The ultrasound transducer is adapted to simultaneously apply ultrasonic therapy to tissue at a plurality of spaced locations in tissue, wherein the module modifies a spacing between the plurality of spaced locations via dithering of a first focal zone and a second focal zone, such that dithering via modulation of a frequency precisely moves a position of a beam focus point at the plurality of spaced locations, wherein the module further comprises an interface guide designed to for removable coupling to a hand wand to provide electronic communication and power between the module and the hand wand.

In one embodiment, the ultrasound transducer is adapted to apply ultrasonic therapy using amplitude modulation whereby a plurality of portions of the ultrasound transducer are adapted to emit ultrasonic therapy at a plurality of amplitudes of acoustic intensity, wherein a first amplitude is different than a second amplitude. In one embodiment, the ultrasound transducer is adapted to apply ultrasonic therapy whereby a plurality of portions of the ultrasound transducer are adapted to emit ultrasonic therapy at a plurality of phases of acoustic intensity, wherein a first phase is different than a second phase. In one embodiment, the ultrasound transducer comprises piezoelectric material and the plurality of portions of the ultrasound transducer are adapted to create a plurality of corresponding piezoelectric material variations in response to an electric field applied to the ultrasound transducer. In one embodiment, at least one portion of the ultrasonic transducer is adapted to emit ultrasonic therapy at two or more amplitudes of acoustic intensity, and wherein the amplitude of ultrasonic therapy emitted by the at least one portion of the ultrasonic transducer remains constant over time. In one embodiment, the ultrasonic treatment is at least one of a face lift, a brow lift, a chin lift, an eye treatment (e.g., malar bags, treat infraorbital laxity), a wrinkle reduction, a décolletage improvement, a buttock lift, a scar reduction, a burn treatment, a tattoo removal, a skin tightening (e.g., abdominal laxity treatment or tightening of the skin on other areas of the body and face, such as any excess skin or tissue, such as during or after weight loss, such as, for example, the abdomen, buttocks, thighs, arms, and other areas), a vein removal, a vein reduction, a treatment on a sweat gland, a treatment of hyperhidrosis, a sun spot removal, a fat treatment, a vaginal rejuvenation, and an acne treatment.

In various embodiments, a method of dithering simultaneous focused ultrasound treatment beams includes providing an ultrasonic probe comprising an ultrasound transducer comprising a single transduction element adapted to simultaneously apply ultrasonic therapy to tissue at a plurality of spaced locations at a focal depth and a control module coupled to the ultrasonic probe for controlling the ultrasound transducer, and dithering the spacing between the spaced locations of a first focal zone and a second focal zone via modulation of a frequency to move a position of an ultrasound focus point at the spaced locations.

In one embodiment, the method includes imaging the first focal zone with an ultrasound imaging element. In one embodiment, the method includes imaging the second focal zone with an ultrasound imaging element. In one embodiment, the spacing between the first focal zone and the second focal zone is dithered in a range of between 1-50%. In one embodiment, the spacing between the first focal zone and the second focal zone is 1.5 mm and is by 0.1 mm. In one embodiment, the modulation of frequency is in a range of between 1-50%. In one embodiment, the ultrasound treatment is at least one of a face lift, a brow lift, a chin lift, an eye treatment (e.g., malar bags, treat infraorbital laxity), a wrinkle reduction, a décolletage improvement, a buttock lift, a scar reduction, a burn treatment, a tattoo removal, a skin tightening (e.g., treating laxity on the face and body, such as abdominal laxity treatment, tightening of the skin on other areas of the body and face, such as any excess skin or tissue, such as during or after weight loss, such as, for example, the abdomen, buttocks, thighs, arms, and other areas), a vein removal, a vein reduction, a treatment on a sweat gland, a treatment of hyperhidrosis, a sun spot removal, a fat treatment, a vaginal rejuvenation, and an acne treatment.

In various embodiments, a method of dithering a focused ultrasound beam includes providing an ultrasonic probe comprising a single transduction element and a control module, wherein the single transduction element is adapted to apply ultrasonic therapy to tissue at a focal zone at a focal depth, wherein the control module is coupled to the ultrasonic probe for controlling the single transduction element, and dithering the focal zone via modulation of a frequency to alter a size of the focal zone at the tissue.

In one embodiment, the relative position of the focal zone is dithered in a range of between 1-50%. In one embodiment, a second focal zone is emitted simultaneously from the single transduction element. In one embodiment, the method includes imaging the focal zone with an ultrasound imaging element. In one embodiment, the modulation of the frequency is in a range of between 1-50%.

In several of the embodiments described herein, the procedure is entirely cosmetic and not a medical act. For example, in one embodiment, the methods described herein need not be performed by a doctor, but at a spa or other aesthetic institute. In some embodiments, a system can be used for the non-invasive cosmetic treatment of skin.

In some embodiments simultaneous multi-focus therapy using multi-channel signal mixing. In several embodiments, a treatment system utilizes multiple therapy channels to enable electronic focusing and/or steering. For example, a treatment system that utilizes multiple therapy channels to enable electronic focusing and/or steering allows for faster electronic dithering to either create more thermal coagulation using the same amount of energy as other treatment devices or equal thermal coagulation using electronic dithering with less energy than other treatment devices.

In various embodiments, an ultrasound treatment system configured for generating multiple simultaneous focus points from an ultrasound transducer includes an ultrasonic probe comprising an ultrasound transducer with a multiple transduction elements adapted to simultaneously apply ultrasonic therapy to tissue at a plurality of spaced locations, wherein each transduction element comprises a channel wherein the ultrasonic probe has a geometric focus; wherein the ultrasonic probe has a first electronic focus; and wherein the ultrasonic probe has a second electronic focus; a control module coupled to the ultrasonic probe for controlling the ultrasound transducer, wherein the control module modifies the spacing between the spaced locations via dithering of a first focal zone and a second focal zone, such that dithering via an excitation function that moves a position of a beam focus point at the spaced locations.

In one embodiment, the plurality of locations are positioned in a linear sequence within a cosmetic treatment zone, wherein the spaced locations are separated. In one embodiment, a first set of locations is positioned within a first cosmetic treatment zone and a second set of locations is positioned within a second cosmetic treatment zone, the first zone being different from the second zone. In one embodiment, the ultrasound transducer is adapted to apply ultrasonic therapy whereby a plurality of portions of the ultrasound transducer are adapted to emit ultrasonic therapy at a plurality of amplitudes of acoustic intensity, wherein a first amplitude is different than a second amplitude. In one embodiment, at least one portion of the ultrasonic transducer is adapted to emit ultrasonic therapy at two or more amplitudes of acoustic intensity, and wherein the amplitude of ultrasonic therapy emitted by the at least one portion of the piezoelectric varies over time. In one embodiment, the ultrasound transducer comprises piezoelectric material and the plurality of portions of the ultrasound transducer are adapted to create a plurality of corresponding piezoelectric material variations in response to an electric field applied to the ultrasound transducer. In one embodiment, the plurality of piezoelectric material variations comprise at least one of expansion of the piezoelectric material and contraction of the piezoelectric material. In one embodiment, the ultrasound transducer is adapted to apply ultrasonic therapy via phase shifting whereby a plurality of portions of the ultrasound transducer are adapted to emit ultrasonic therapy at a plurality of phases of acoustic intensity, wherein a first phase is different than a second phase. In one embodiment, the plurality of phases comprises discrete phase values. In one embodiment, the ultrasound transducer is adapted to apply ultrasonic therapy using amplitude modulation whereby a plurality of portions of the ultrasound transducer are adapted to emit ultrasonic therapy at a plurality of amplitudes of acoustic intensity, wherein a first amplitude is different than a second amplitude; and apply ultrasonic therapy whereby a plurality of portions of the ultrasound transducer are adapted to emit ultrasonic therapy at a plurality of phases of acoustic intensity, wherein a first phase is different than a second phase.

In various embodiments, the ultrasonic treatment is at least one of: a face lift, a brow lift, a chin lift, an eye (e.g., malar bags, treat infraorbital laxity) treatment, a wrinkle reduction, a décolletage improvement, a buttock lift, a scar reduction, a burn treatment, a skin tightening (e.g., abdominal, thigh, buttock, arm, neck or other laxity treatment), a blood vessel reduction, a treatment of a sweat gland, a sun spot removal, a fat treatment, and a cellulite treatment.

In various embodiments, an ultrasound treatment system for use in cosmetic treatment for forming multiple simultaneous focal zones from an ultrasound transducer, the system includes an ultrasonic probe including a control module adapted to modify a spacing between a first focal zone and a second focal zone, a switch operably controlling an ultrasonic treatment function for providing an ultrasonic treatment; and a movement mechanism adapted to direct ultrasonic treatment in at least one pair of simultaneous sequences of individual thermal cosmetic treatment zones; and a transducer module adapted to apply ultrasonic therapy, wherein the transducer module is adapted for ultrasonic imaging and/or ultrasonic treatment, wherein the transducer module is adapted for coupling to the ultrasonic probe, wherein the transducer module comprises an ultrasound transducer adapted to simultaneously apply ultrasonic therapy to tissue at a plurality of locations, wherein the transducer module is adapted to be operably coupled to at least one of the switch and the movement mechanism; and wherein the control module comprises a processor and a display for controlling the transducer module.

In one embodiment, the transducer module is adapted to apply ultrasonic therapy whereby a plurality of portions of the transducer module are adapted to emit ultrasonic therapy at a plurality of amplitudes of acoustic intensity, wherein a first amplitude is different than a second amplitude. In one embodiment, the transducer module is adapted to apply ultrasonic therapy whereby a plurality of portions of the transducer module are adapted to emit ultrasonic therapy at a plurality of acoustic intensities. In various embodiments, an ultrasound treatment system for generating a multi-focus treatment using multi-channel signal mixing including a module comprising an ultrasound transducer, wherein the ultrasound transducer is adapted to simultaneously apply ultrasonic therapy to tissue at a plurality of spaced locations in tissue, wherein the module modifies a spacing between the plurality of spaced locations between a first focal zone and a second focal zone, such that multi-channel signal mixing precisely moves a position of a beam focus point at the plurality of spaced locations, wherein the module further comprises an interface guide designed to for removable coupling to a hand wand to provide electronic communication and power between the module and the hand wand. In one embodiment, the ultrasound transducer is adapted to apply ultrasonic therapy whereby a plurality of portions of the ultrasound transducer are adapted to emit ultrasonic therapy at a plurality of amplitudes of acoustic intensity, wherein a first amplitude is different than a second amplitude. In one embodiment, the ultrasound transducer is adapted to apply ultrasonic therapy whereby a plurality of portions of the ultrasound transducer are adapted to emit ultrasonic therapy at a plurality of phases of acoustic intensity, wherein a first phase is different than a second phase. In one embodiment, the ultrasound transducer comprises piezoelectric material and the plurality of portions of the ultrasound transducer are adapted to create a plurality of corresponding piezoelectric material variations in response to an electric field applied to the ultrasound transducer. In one embodiment, at least one portion of the ultrasonic transducer is adapted to emit ultrasonic therapy at two or more amplitudes of acoustic intensity, and wherein the amplitude of ultrasonic therapy emitted by the at least one portion of the ultrasonic transducer remains constant over time. In one embodiment, the ultrasonic treatment is at least one of a face lift, a brow lift, a chin lift, an eye treatment (e.g., malar bags, treat infraorbital laxity), a wrinkle reduction, a décolletage improvement, a buttock lift, a scar reduction, a burn treatment, a tattoo removal, a skin tightening (e.g., a laxity treatment, a tissue laxity treatment, an abdominal laxity treatment, and any tightening of the skin on other areas of the body and face, such as any excess skin or tissue, such as during or after weight loss, such as, for example, the abdomen, buttocks, thighs, arms, and other areas) a vein removal, a vein reduction, a treatment on a sweat gland, a treatment of hyperhidrosis, a sun spot removal, a fat treatment, a vaginal rejuvenation, and an acne treatment. In various embodiments, a method of generating simultaneous focused ultrasound treatment beams using multi-channel signal mixing includes providing an ultrasonic probe comprising an ultrasound transducer comprising a plurality of transduction elements adapted to simultaneously apply ultrasonic therapy to tissue at a plurality of spaced locations at a plurality of focal depths and a control module coupled to the ultrasonic probe for controlling the ultrasound transducer, and modifying the spacing between the spaced locations of a first focal zone and a second focal zone via multi-channel signal mixing to move a position of an ultrasound focus point at the spaced locations. In one embodiment, the method includes imaging the first focal zone with an ultrasound imaging element. In one embodiment, the method includes imaging the second focal zone with an ultrasound imaging element. In one embodiment, the spacing between the first focal zone and the second focal zone is varied in a range of between 1-50%. In one embodiment, the spacing between the first focal zone and the second focal zone is 1.5 mm and is by 0.1 mm. In one embodiment, the spacing between electrical foci ranges of between 10-50% of the nominal distance between the electrical foci. In one embodiment, the ultrasound treatment is at least one of a face lift, a brow lift, a chin lift, an eye treatment, a wrinkle reduction, a décolletage improvement, a buttock lift, a scar reduction, a burn treatment, a tattoo removal, a skin tightening (e.g., tightening of tissue on a human or an abdominal laxity treatment), a vein removal, a vein reduction, a treatment on a sweat gland, a treatment of hyperhidrosis, a sun spot removal, a fat treatment, a vaginal rejuvenation, and an acne treatment.

In various embodiments, a method of generating simultaneous focused ultrasound beams includes providing an ultrasonic probe comprising an array of transduction elements and a control module, wherein the array of transduction elements is adapted to apply ultrasonic therapy to tissue at a focal zone at a plurality of foci, wherein the control module is coupled to the ultrasonic probe for controlling the array of transduction elements, and moving the focal zone.

In one embodiment, the relative position of the focal zone is moved in a range of between 10-50%. In one embodiment, a second focal zone is emitted simultaneously from the single transduction element. In one embodiment, the method includes imaging the focal zone with an ultrasound imaging element. In one embodiment, the system is designed to work non-invasively to treat tissue. In one embodiment, the method functions in a non-invasive manner to treat tissue.

In various embodiments, ultrasound imaging is employed to ensure sufficient acoustic coupling during delivery of an ultrasound therapy treatment. In various embodiments, ultrasound imaging is employed to prevent treatment at an undesired area in a body, such as a bone or an implant. Sound, unlike light, needs a medium for propagation. In an embodiment, an ultrasound treatment system acoustically couples ultrasound energy from the transducer to the body through an acoustic window using gel. In this embodiment, the gel is the medium which mimics the acoustic impedance properties of tissue so there is efficient transfer of energy from the device into tissue. Unfortunately, any pockets of air between the transducer and tissue prevent proper coupling and can therefore cause an inadequate transfer of the ultrasound therapy energy. The ultrasound imaging checks this coupling. Inadequate coupling may show up as shadows or vertical stripes in the ultrasound images or a completely dark image. Even if there is sufficient coupling, tissues or objects, such as bone or an implant can cause challenges since these objects can have a different acoustic impedance and absorption characteristics than soft tissue (e.g. skin, muscle). Because of this, objects (such as bone or an implant) in between the device and intended therapy focus may cause significant reflection and the appearance heating at a shallower depth than intended. Objects (e.g., bone, etc.) slightly beyond the focus may also cause issues since the object reflects and readily absorbs the ultrasound from the soft tissue. The reflected energy may inadvertently add to the energy already at the therapy focus causing a higher temperature rise than intended. The absorbed energy at the bone may cause heating or discomfort in the bone.

In various embodiments, advantages of the present invention include using image to assess coupling of an ultrasound therapy beam to the intended treatment tissue. In various embodiments, higher resolution imaging is advantageous to provide more detail in an image of the tissue in and near the target tissue for treatment. In various embodiments, the invention improves safety characteristics, improves efficacy performance, provides a component of safety and efficacy for bulk heating devices (such as a band treatment, a linear focal treatment zone, a cylindrical focal line, a plane and/or a volume, etc.) for body shaping, submental fat, abdomen and/or flanks, arms, inner thigh, outer thigh, buttocks, laxity, abdominal laxity, etc., provides qualitative and/or quantitative assessment of coupling, provides for blending of high resolution image(s) with coupling image(s), is employed for assessing out-of-plane impediments post-focally (e.g. bone, intestine, implants), and/or can be used to reduce the need for sonographer equivalent skills.

In various embodiments, an ultrasound treatment and imaging system includes an ultrasonic probe comprising an ultrasound therapy transducer adapted to apply ultrasonic therapy to tissue, an ultrasound imaging transducer adapted for imaging the tissue, and an acoustic window, wherein the ultrasound imaging transducer comprises an annular imaging array; wherein the ultrasound imaging transducer comprises a plurality of transmit channels; wherein the ultrasound imaging transducer comprises a plurality of receive channels; wherein the ultrasound imaging transducer is configured for focusing at a location proximate the ultrasound imaging transducer with respect to a distance between the ultrasound imaging transducer and the acoustic window; and a control module coupled to the ultrasonic probe for controlling the ultrasound imaging transducer, wherein the ultrasound imaging transducer is configured to interrogate more than 40% of the acoustic window.

In various embodiments, an ultrasound treatment and imaging system includes an ultrasonic probe comprising an ultrasound therapy transducer adapted to apply ultrasonic therapy to tissue, an ultrasound imaging transducer adapted for imaging the tissue, and an acoustic window, wherein the ultrasound imaging transducer comprises an annular imaging array; wherein the ultrasound imaging transducer comprises a plurality of transmit channels; wherein the ultrasound imaging transducer comprises a plurality of receive channels; wherein the wherein the ultrasound imaging transducer operates at an imaging frequency of between 8 MHz to 50 MHz, wherein the ultrasound imaging transducer is configured to image tissue at a depth of up to 25 mm (e.g., 5 mm, 8 mm, 10 mm, 12 mm, 15 mm, 20 mm) below a skin surface; wherein the ultrasound imaging transducer is configured for focusing at a location behind the ultrasound imaging transducer with respect to the acoustic window; and a control module coupled to the ultrasonic probe for controlling the ultrasound imaging transducer, wherein the ultrasound imaging transducer is configured to interrogate more than 10% of the acoustic window.

In various embodiments, an ultrasound treatment and imaging system includes an ultrasonic probe comprising an ultrasound therapy transducer adapted to apply ultrasonic therapy to tissue, an ultrasound imaging transducer adapted for imaging the tissue, and an acoustic window, wherein the ultrasound imaging transducer comprises an annular or a linear imaging array; wherein the ultrasound imaging transducer comprises a plurality of transmit channels; wherein the ultrasound imaging transducer comprises a plurality of receive channels; wherein the wherein the ultrasound imaging transducer operates at an imaging frequency of between 8 MHz to 50 MHz, wherein the ultrasound imaging transducer is configured to image tissue at a depth of up to 25 mm below a skin surface; wherein the ultrasound imaging transducer is configured for focusing at a location proximate the ultrasound imaging transducer with respect to a distance between the ultrasound imaging transducer and the acoustic window; and a control module coupled to the ultrasonic probe for controlling the ultrasound imaging transducer, wherein the ultrasound imaging transducer is configured to interrogate more than 15% of the acoustic window.

In one embodiment, an imaging beam width from the ultrasound imaging transducer is at least 20% the cross-sectional size of a therapy beam width from the ultrasound therapy transducer. In one embodiment, an imaging beam width from the ultrasound imaging transducer is at least 30% the cross-sectional size of a therapy beam width from the ultrasound therapy transducer. In one embodiment, an imaging beam width from the ultrasound imaging transducer is at least 40% the cross-sectional size of a therapy beam width from the ultrasound therapy transducer. In one embodiment, an imaging beam width from the ultrasound imaging transducer is at least 50% the cross-sectional size of a therapy beam width from the ultrasound therapy transducer. In one embodiment, an imaging beam width from the ultrasound imaging transducer is at least 80% the cross-sectional size of a therapy beam width from the ultrasound therapy transducer.

In one embodiment, a coupling of the imaging of the ultrasound imaging transducer provides an indication of the coupling for the treatment by the ultrasound therapy transducer. In one embodiment, the ultrasound imaging transducer is configured to interrogate more than 80% of the acoustic window. In one embodiment, the ultrasound imaging transducer is configured to interrogate more than 90% of the acoustic window. In one embodiment, the annular imaging array is positioned in the ultrasound therapy transducer.

In one embodiment, the control module controls the ultrasound imaging transducer for vector imaging. In one embodiment, the control module controls the ultrasound imaging transducer for defocused vector imaging.

In one embodiment, the ultrasound therapy transducer is configured for treatment of tissue at a first set of locations that is positioned within a first cosmetic treatment zone and a second set of locations that is positioned within a second cosmetic treatment zone, the first zone being different from the second zone. In one embodiment, the ultrasound therapy transducer is adapted to apply ultrasonic therapy using amplitude modulation whereby a plurality of portions of the ultrasound transducer are adapted to emit ultrasonic therapy at a plurality of amplitudes of acoustic intensity, wherein a first amplitude is different than a second amplitude. In one embodiment, at least one portion of the ultrasonic transducer is adapted to emit ultrasonic therapy at two or more amplitudes of acoustic intensity, and wherein the amplitude of ultrasonic therapy emitted by the at least one portion of the piezoelectric varies over time. In one embodiment, the ultrasound transducer comprises piezoelectric material and the plurality of portions of the ultrasound transducer are adapted to create a plurality of corresponding piezoelectric material variations in response to an electric field applied to the ultrasound transducer. In one embodiment, plurality of piezoelectric material variations comprise at least one of expansion of the piezoelectric material and contraction of the piezoelectric material. In one embodiment, the ultrasound transducer is adapted to apply ultrasonic therapy via phase shifting whereby a plurality of portions of the ultrasound transducer are adapted to emit ultrasonic therapy at a plurality of phases of acoustic intensity, wherein a first phase is different than a second phase. In one embodiment, the plurality of phases comprises discrete phase values. In one embodiment, the ultrasound transducer is adapted to apply ultrasonic therapy using amplitude modulation whereby a plurality of portions of the ultrasound transducer are adapted to emit ultrasonic therapy at a plurality of amplitudes of acoustic intensity, wherein a first amplitude is different than a second amplitude; and apply ultrasonic therapy whereby a plurality of portions of the ultrasound transducer are adapted to emit ultrasonic therapy at a plurality of phases of acoustic intensity, wherein a first phase is different than a second phase.

In various embodiments, the ultrasonic treatment is at least one of a face lift, a brow lift, a chin lift, an eye treatment, a wrinkle reduction, a décolletage improvement, a buttock lift, a scar reduction, a burn treatment, a skin tightening (e.g., an abdominal laxity treatment), a blood vessel reduction, a treatment of a sweat gland, a sun spot removal, a fat treatment, and a cellulite treatment.

In various embodiments, a method of confirming coupling between an ultrasound probe and tissue for treatment includes providing an ultrasonic probe comprising an acoustic window, an ultrasound transducer comprising an ultrasound therapy transduction element adapted to apply ultrasonic therapy to a tissue, a plurality of imaging transduction elements in an array for imaging the tissue, and a control module coupled to the ultrasonic probe for controlling the ultrasound transducer, and interrogating at least 20% of the acoustic window with an imaging beam from the plurality of imaging transduction elements.

In one embodiment, the plurality of imaging transduction elements interrogates at least 30% of the acoustic window. In one embodiment, the plurality of imaging transduction elements interrogates at least 40% of the acoustic window. In one embodiment, the plurality of imaging transduction elements interrogates at least 50% of the acoustic window. In one embodiment, the plurality of imaging transduction elements interrogates at least 60% of the acoustic window. In one embodiment, the plurality of imaging transduction elements interrogates at least 70% of the acoustic window. In one embodiment, the method further includes vector imaging. In one embodiment, the method further includes defocused vector imaging. In one embodiment, the method further includes imaging a first focal zone in the tissue with the plurality of imaging transduction elements. In one embodiment, the method further includes imaging a second focal zone in the tissue with the plurality of imaging transduction elements. In various embodiments, the ultrasound treatment is at least one of a face lift, a brow lift, a chin lift, an eye treatment, a wrinkle reduction, a décolletage improvement, a buttock lift, a scar reduction, a burn treatment, a tattoo removal, a skin tightening, (e.g., a laxity treatment), a vein removal, a vein reduction, a treatment on a sweat gland, a treatment of hyperhidrosis, a sun spot removal, a fat treatment, a vaginal rejuvenation, and an acne treatment.

In several of the embodiments described herein, the procedure is entirely cosmetic and not a medical act. For example, in one embodiment, the methods described herein need not be performed by a doctor, but at a spa or other aesthetic institute. In some embodiments, a system can be used for the non-invasive cosmetic treatment of skin.

In several embodiments, provided are systems and methods that successfully improve the ultrasound imaging of tissue while moving, such as when an imaging transducer is on a motion mechanism. In various embodiments, higher resolution is achieved. In various embodiments, better imaging signal quality is obtained. In various embodiments, ultrasound imaging is used with a therapeutic tissue treatment.

In various embodiments, an ultrasound treatment and imaging system configured for reducing imaging misalignment, including an ultrasonic probe comprising an ultrasound therapy transducer adapted to apply ultrasonic therapy to tissue, an ultrasound imaging transducer adapted for imaging the tissue, and a motion mechanism for moving the ultrasound imaging transducer in a first direction and a second direction. In an embodiment, the ultrasound imaging transducer is mechanically attached to the motion mechanism. In an embodiment, the first direction is linear. In an embodiment, the second direction is linear. In an embodiment, the first direction is parallel to the second direction. In an embodiment, the first direction is opposite the second direction. In an embodiment, the ultrasound imaging transducer images with a first focal zone sequence order (f1, f2) when travelling in the first direction, the ultrasound imaging transducer images with a second focal zone sequence order (f2, f1) when travelling in the second direction, and a spatial registration between the first direction imaging and the second direction imaging is improved by staggering a triggering location. In an embodiment, a control module is coupled to the ultrasonic probe for controlling the ultrasound imaging transducer.

In various embodiments, an ultrasound treatment and imaging system configured for reducing imaging misalignment, includes an ultrasonic probe comprising an ultrasound therapy transducer adapted to apply ultrasonic therapy to tissue, an ultrasound imaging transducer adapted for imaging the tissue, and a motion mechanism for moving the ultrasound imaging transducer in a first direction and a second direction. In an embodiment, the ultrasound imaging transducer is mechanically attached to the motion mechanism, wherein the first direction is linear, wherein the second direction is linear, wherein the first direction is parallel to the second direction, wherein the first direction is opposite the second direction, wherein the ultrasound imaging transducer images with a first focal zone sequence order (f1, f2, f3, f4) when travelling in the first direction, wherein the ultrasound imaging transducer images with a second focal zone sequence order (f4, f3, f2, f1) when travelling in the second direction, wherein a spatial registration between the first direction imaging and the second direction imaging is improved by staggering a triggering location, wherein the imaging system employs a sequence of two consecutive A-lines following progression of (line 1: f1, f2, f3, f4; line2: f4, f3, f2, f1) continuously; and a control module coupled to the ultrasonic probe for controlling the ultrasound imaging transducer.

In various embodiments, an ultrasound treatment and imaging system configured for reducing imaging misalignment, includes an ultrasonic probe comprising an ultrasound therapy transducer adapted to apply ultrasonic therapy to tissue, an ultrasound imaging transducer adapted for imaging the tissue, and a motion mechanism for moving the ultrasound imaging transducer in a first direction and a second direction. In an embodiment, the ultrasound imaging transducer is mechanically attached to the motion mechanism. In an embodiment, the first direction is opposite the second direction. In an embodiment, the ultrasound imaging transducer images with a focal zone sequence order (f1, . . . , fN), where N>1 when travelling in the first direction. In an embodiment, the ultrasound imaging transducer images with a second focal zone sequence order (fN, . . . , f1) when travelling in the second direction. In an embodiment, a spatial registration between the first direction imaging and the second direction imaging is improved by staggering a triggering location. In an embodiment, the imaging system employs a directionally dependent focal zone sequencing with alternating between (f1- . . . -fN) and (fN- . . . -f1) on consecutive A-lines; and a control module coupled to the ultrasonic probe for controlling the ultrasound imaging transducer.

In an embodiment, the first direction of motion of the transducer is any one or more of the group consisting of: linear, rotational, and curved. In an embodiment, the second direction is the reversed path of the first direction. In an embodiment, the first direction of motion occurs in multiple dimensions and the second direction is the reversed path of the first direction. In an embodiment, the ultrasound imaging transducer images with a first focal zone sequence order is specified as (f1, . . . , fN), where N>1. In an embodiment, the ultrasound therapy transducer is configured for treatment of tissue at a first set of locations that is positioned within a first cosmetic treatment zone and a second set of locations that is positioned within a second cosmetic treatment zone, the first zone being different from the second zone. In an embodiment, the ultrasound therapy transducer is adapted to apply ultrasonic therapy using amplitude modulation whereby a plurality of portions of the ultrasound transducer are adapted to emit ultrasonic therapy at a plurality of amplitudes of acoustic intensity, wherein a first amplitude is different than a second amplitude. In an embodiment, at least one portion of the ultrasonic transducer is adapted to emit ultrasonic therapy at two or more amplitudes of acoustic intensity, and wherein the amplitude of ultrasonic therapy emitted by the at least one portion of the piezoelectric varies over time. In an embodiment, the ultrasound transducer comprises piezoelectric material and the plurality of portions of the ultrasound transducer are adapted to create a plurality of corresponding piezoelectric material variations in response to an electric field applied to the ultrasound transducer. In an embodiment, the plurality of piezoelectric material variations comprise at least one of expansion of the piezoelectric material and contraction of the piezoelectric material. In an embodiment, the ultrasound transducer is adapted to apply ultrasonic therapy via phase shifting whereby a plurality of portions of the ultrasound transducer are adapted to emit ultrasonic therapy at a plurality of phases of acoustic intensity, wherein a first phase is different than a second phase. In an embodiment, the plurality of phases comprises discrete phase values. In an embodiment, the ultrasound transducer is adapted to apply ultrasonic therapy using amplitude modulation whereby a plurality of portions of the ultrasound transducer are adapted to emit ultrasonic therapy at a plurality of amplitudes of acoustic intensity, wherein a first amplitude is different than a second amplitude; and apply ultrasonic therapy whereby a plurality of portions of the ultrasound transducer are adapted to emit ultrasonic therapy at a plurality of phases of acoustic intensity, wherein a first phase is different than a second phase. In various embodiments, the ultrasonic treatment is at least one of: a face lift, a brow lift, a chin lift, an eye treatment, a wrinkle reduction, a décolletage improvement, a buttock lift, a scar reduction, a burn treatment, a skin tightening (e.g., a laxity treatment), a blood vessel reduction, a treatment of a sweat gland, a sun spot removal, a fat treatment, a cellulite treatment, a vaginal rejuvenation, and an acne treatment.

In various embodiments, a method of reducing imaging misalignment in a moving ultrasound probe, including staggering a triggering location of a spatial registration between a first direction imaging and a second direction imaging with an ultrasonic probe, the ultrasound probe comprising an ultrasound therapy transducer adapted to apply ultrasonic therapy to tissue, an ultrasound imaging transducer adapted for imaging the tissue, and a motion mechanism for moving the ultrasound imaging transducer in a first direction and a second direction, wherein the ultrasound imaging transducer is mechanically attached to the motion mechanism, wherein the first direction is opposite the second direction, wherein the ultrasound imaging transducer images with a focal zone sequence order (f1, . . . , fN), with N>1, wherein the ultrasound imaging transducer images with a first focal zone sequence order (f1, . . . , fN) when travelling in the first direction, wherein the ultrasound imaging transducer images with a second focal zone sequence order (fN, . . . , f1) when travelling in the second direction.

In an embodiment, N=any one of the group consisting of: 2, 3, 4, 5, 6, 7, 8, 9, and 10. In an embodiment, N=4. In various embodiments, the ultrasound treatment is at least one of a face lift, a brow lift, a chin lift, an eye treatment, a wrinkle reduction, a décolletage improvement, a buttock lift, a scar reduction, a burn treatment, a tattoo removal, a skin tightening (e.g., an abdominal laxity treatment), a vein removal, a vein reduction, a treatment on a sweat gland, a treatment of hyperhidrosis, a sun spot removal, a fat treatment, a vaginal rejuvenation, and an acne treatment.

The methods summarized above and set forth in further detail below describe certain actions taken by a practitioner; however, it should be understood that they can also include the instruction of those actions by another party. Thus, actions such as "dithering an energy beam" include "instructing the dithering of an energy beam."

In some embodiments, the system comprises various features that are present as single features (as opposed to multiple features). For example, in one embodiment, the system includes a single transduction element that produces two simultaneous treatment focus points that are dithered. Multiple features or components are provided in alternate embodiments. In various embodiments, the system comprises, consists essentially of, or consists of one, two, three, or more embodiments of any features or components disclosed herein. In some embodiments, a feature or component is not included and can be negatively disclaimed from a specific claim, such that the system is without such feature or component.

Further, areas of applicability will become apparent from the description provided herein. It should be understood that the description and specific examples are intended for purposes of illustration only and are not intended to limit the scope of the embodiments disclosed herein.

BRIEF DESCRIPTION OF THE DRAWINGS

The drawings described herein are for illustration purposes only and are not intended to limit the scope of the present disclosure in any way. Embodiments of the present invention will become more fully understood from the detailed description and the accompanying drawings wherein:

FIG. 5 is table illustrating foci separation for apertures with different spatial frequencies according to various embodiments of the present invention.

FIG. 8 is a schematic representation of aperture poling with a spatial frequency that can be modified by excitation of channels according to various embodiments of the present invention.

FIG. 9 is a schematic representation of a poled ceramic with a spatial frequency that can be modified by excitation of channels covering two poled areas of the ceramic according to various embodiments of the present invention.

DETAILED DESCRIPTION

Figure 1A:
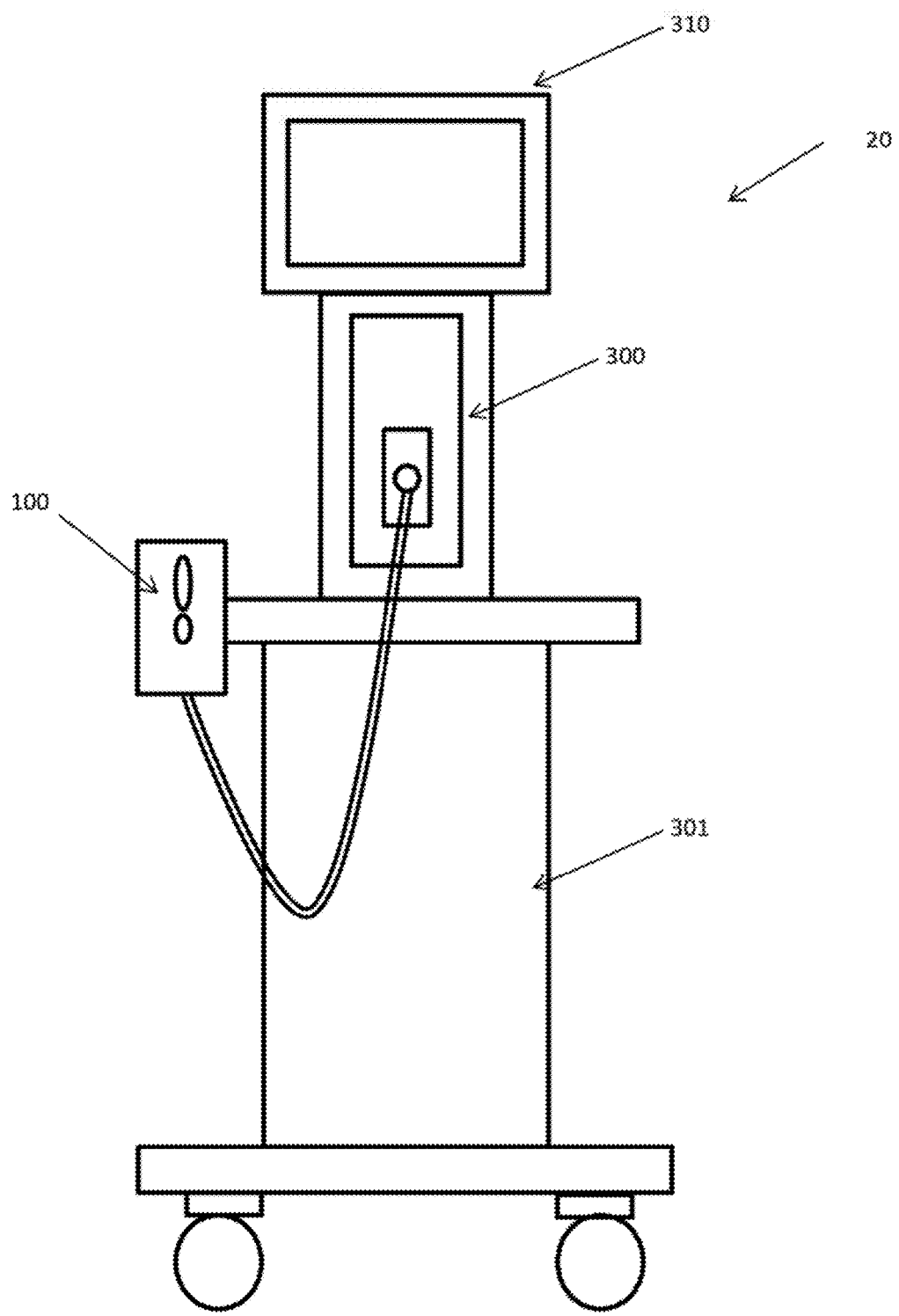
FIG. 1A is a schematic illustration of an ultrasound system according to various embodiments of the present invention.

The following description sets forth examples of embodiments, and is not intended to limit the present invention or its teachings, applications, or uses thereof. It should be understood that throughout the drawings, corresponding reference numerals indicate like or corresponding parts and features. The description of specific examples indicated in various embodiments of the present invention are intended for purposes of illustration only and are not intended to limit the scope of the invention disclosed herein. Moreover, recitation of multiple embodiments having stated features is not intended to exclude other embodiments having additional features or other embodiments incorporating different combinations of the stated features. Further, features in one embodiment (such as in one figure) may be combined with descriptions (and figures) of other embodiments.

In various embodiments, systems and methods for ultrasound treatment of tissue are adapted for and/or configured to provide cosmetic treatment. In some embodiments, devices and methods of directing ultrasound therapy to a single focus point or multiple, simultaneous focus points, employing ultrasound imaging to confirm sufficient acoustic coupling to a treatment area for improving performance or providing improved correlation between movement in a first and second direction when forming images in cosmetic and/or medical procedures are provided in several embodiments. In some embodiments, devices and methods of employing ultrasound imaging to confirm sufficient acoustic coupling to a treatment area for improving performance and safety when directing ultrasound therapy to a single focus point or multiple, simultaneous focus points in cosmetic and/or medical procedures are provided in several embodiments. In some embodiments, devices and methods of improved ultrasound imaging provide better correlation between movement in a first and second direction when forming images. Embodiments of the invention provide better imaging correlation between a first moving direction and a second moving direction, (e.g., better correlation between left-traveling & right-traveling formed images). Devices and methods of improved ultrasound imaging improve effect B-mode imaging faster (e.g., 1.5×, 2×, 3×, 5× times the scanning rate). In various embodiments, tissue below or even at a skin surface such as epidermis, dermis, fascia, muscle, fat, and superficial muscular aponeurotic system ("SMAS"), are treated non-invasively with ultrasound energy. The ultrasound energy can be focused at one or more treatment points and/or zones, can be unfocused and/or defocused, and can be applied to a region of interest containing at least one of epidermis, dermis, hypodermis, fascia, muscle, fat, cellulite, and SMAS to achieve a cosmetic and/or therapeutic effect. In various embodiments, systems and/or methods provide non-invasive dermatological treatment to tissue through thermal treatment, coagulation, ablation, and/or tightening. In several embodiments disclosed herein, non-invasive ultrasound is used to achieve one or more of the following effects: a face lift, a brow lift, a chin lift, an eye treatment (e.g., malar bags, treat infraorbital laxity), a wrinkle reduction, fat reduction (e.g., treatment of adipose and/or cellulite), cellulite treatment (e.g., dimple or non-dimple type female gynoid lipodystrophy), décolletage improvement (e.g., upper chest), a buttock lift (e.g., buttock tightening), a skin laxity treatment (e.g., treatment of tissue for tightening or an abdominal laxity treatment), a scar reduction, a burn treatment, a tattoo removal, a vein removal, a vein reduction, a treatment on a sweat gland, a treatment of hyperhidrosis, sun spot removal, an acne treatment, and a pimple removal. In one embodiment, fat reduction is achieved. In various embodiments, cellulite (e.g., dimple or non-dimple type gynoid lipodystrophy) reduction or amelioration of one or more characteristics (such as dimples, nodularity, "orange peel" appearance, etc., is achieved by about 10-20%, 20-40%, 40-60%, 60-80% or higher (as well as overlapping ranging therein) as compared to, for example, untreated tissue. In one embodiment, décolletage is treated. In some embodiments, two, three or more beneficial effects are achieved during the same treatment session, and may be achieved simultaneously.

Various embodiments of the present invention relate to devices or methods of controlling the delivery of energy to tissue. In various embodiments, various forms of energy can include acoustic, ultrasound, light, laser, radio-frequency (RF), microwave, electromagnetic, radiation, thermal, cryogenic, electron beam, photon-based, magnetic, magnetic resonance, and/or other energy forms. Various embodiments of the present invention relate to devices or methods of splitting an ultrasonic energy beam into multiple beams. In various embodiments, devices or methods can be used to alter the delivery of ultrasound acoustic energy in any procedures such as, but not limited to, therapeutic ultrasound, diagnostic ultrasound, ultrasonic welding, any application that involves coupling mechanical waves to an object, and other procedures. Generally, with therapeutic ultrasound, a tissue effect is achieved by concentrating the acoustic energy using focusing techniques from the aperture. In some instances, high intensity focused ultrasound (HIFU) is used for therapeutic purposes in this manner. In one embodiment, a tissue effect created by application of therapeutic ultrasound at a particular depth to can be referred to as creation of a thermal coagulation point (TCP). In some embodiments, a zone can include a point. In some embodiments, a zone is a line, plane, spherical, elliptical, cubical, or other one-, two-, or three-dimensional shape. It is through creation of TCPs at particular positions that thermal and/or mechanical ablation of tissue can occur non-invasively or remotely. In some embodiments, an ultrasound treatment does not include cavitation and/or shock waves. In some embodiments, an ultrasound treatment includes cavitation and/or shock waves.

In one embodiment, TCPs can be created in a linear or substantially linear, curved or substantially curved, zone or sequence, with each individual TCP separated from neighboring TCPs by a treatment spacing. In one embodiment, multiple sequences of TCPs can be created in a treatment region. For example, TCPs can be formed along a first sequence and a second sequence separated by a treatment distance from the first sequence. Although treatment with therapeutic ultrasound can be administered through creation of individual TCPs in a sequence and sequences of individual TCPs, it may be desirable to reduce treatment time and corresponding risk of pain and/or discomfort experienced by a patient. Therapy time can be reduced by forming multiple TCPs simultaneously, nearly simultaneously, or sequentially. In some embodiments, a treatment time can be reduced 10%, 20%, 25%, 30%, 35%, 40%, 45%, 50%, 55%, 60%, 65%, 70%, 75%, 80% or more by creating multiple TCPs.

Various embodiments of the present invention address potential challenges posed by administration of ultrasound therapy. In various embodiments, time for effecting the formation of TCPs for a desired cosmetic and/or therapeutic treatment for a desired clinical approach at a target tissue is reduced. In various embodiments, target tissue is, but is not limited to, any of skin, eyelids, eye lash, eye brow, caruncula lacrimalis, crow's feet, wrinkles, eye, nose, mouth (e.g., nasolabial fold, perioral wrinkles), tongue, teeth, gums, ears, brain, heart, lungs, ribs, abdomen (e.g., for abdominal laxity), stomach, liver, kidneys, uterus, breast, vagina, prostrate, testicles, glands, thyroid glands, internal organs, hair, muscle, bone, ligaments, cartilage, fat, fat labuli, adipose tissue, subcutaneous tissue, implanted tissue, an implanted organ, lymphoid, a tumor, a cyst, an abscess, or a portion of a nerve, or any combination thereof.

Various embodiments of ultrasound treatment and/or imaging devices are described in U.S. application Ser. No. 12/996,616, which published as U.S. Publication No. 2011-0112405 A1 on May 12, 2011, which is a U.S. National Phase under 35 U.S.C. § 371 of International Application No. PCT/US2009/046475, filed on Jun. 5, 2009 and published in English on Dec. 10, 2009, which claims the benefit of priority from U.S. Provisional No. 61/059,477 filed Jun. 6, 2008, each of which is incorporated in its entirety by reference, herein. Various embodiments of ultrasound treatment and/or imaging devices are described in U.S. application Ser. No. 14/193,234, which published as U.S. Publication No. 2014/0257145 on Sep. 11, 2014, which is incorporated in its entirety by reference, herein. Various embodiments of ultrasound treatment and/or imaging devices are described in International App. PCT/US15/25581, which published as WO 2015/160708 on Oct. 22, 2015 with a national phase U.S. application Ser. No. 15/302,436, which published as U.S. Publication No. 2017/0028227 on Feb. 2, 2017, each of which is incorporated in its entirety by reference, herein.

System Overview

Figure 1B:
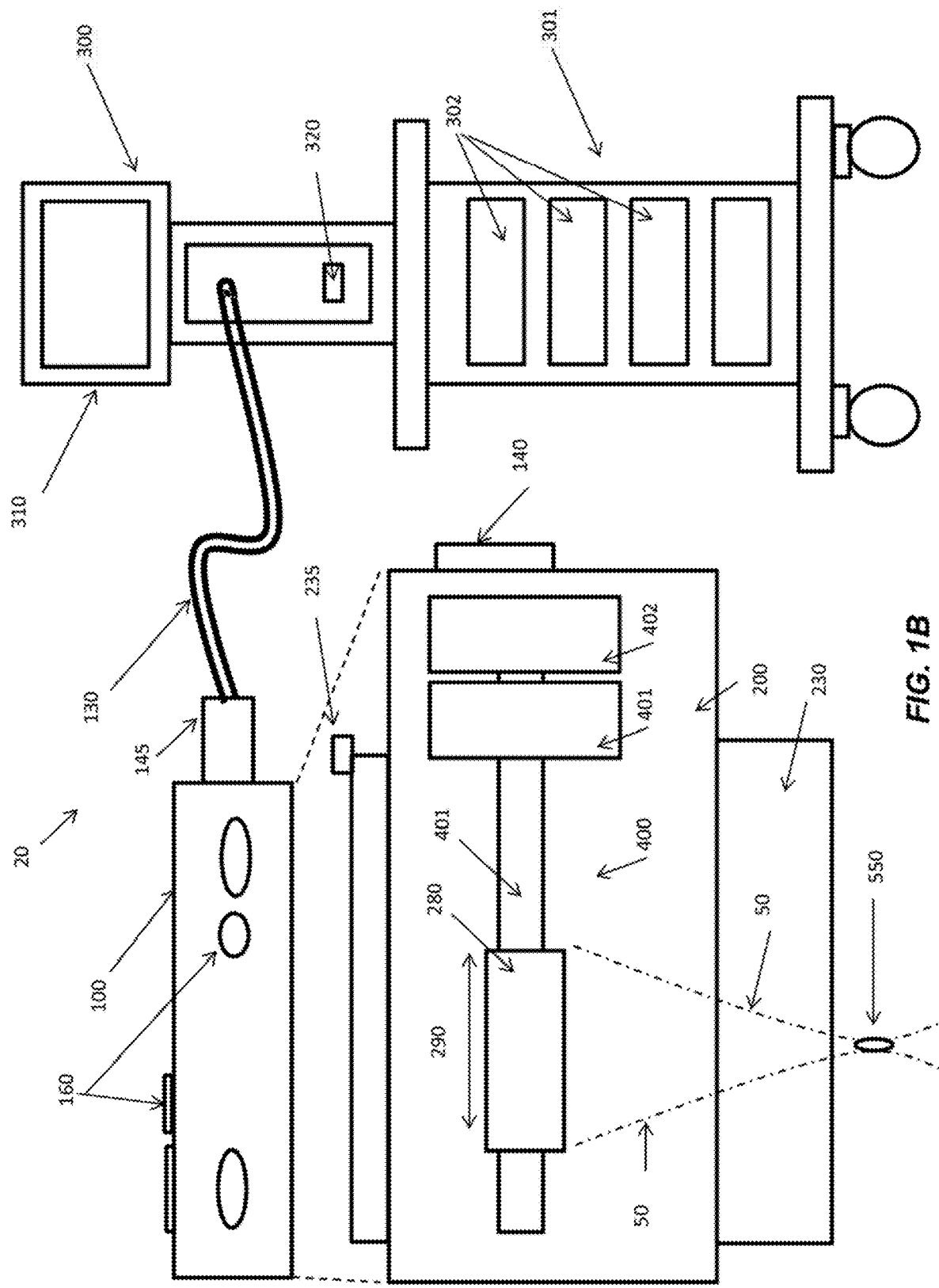
FIG. 1B is a schematic illustration of an ultrasound system according to various embodiments of the present invention.
Figure 1C:
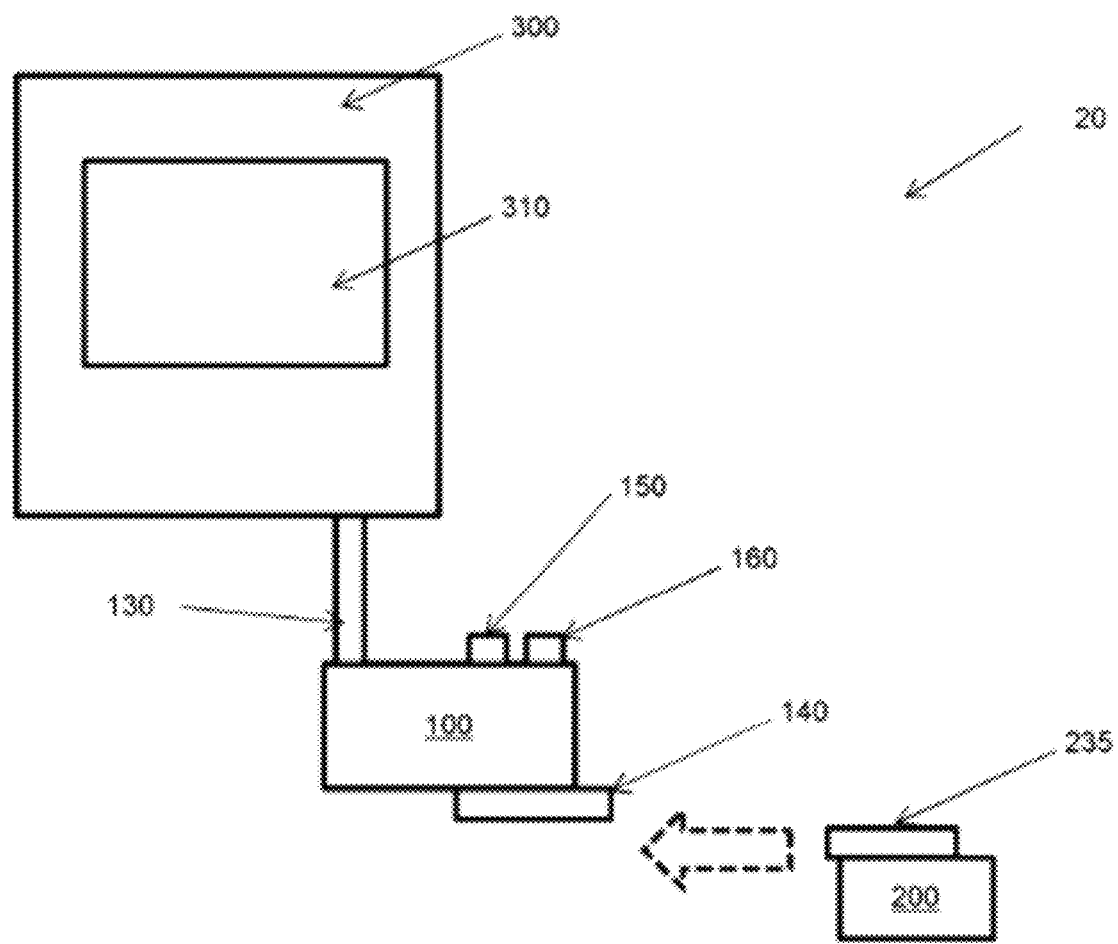
FIG. 1C is a schematic illustration of an ultrasound system according to various embodiments of the present invention.

With reference to the illustration in FIGS. 1A, 1B, and 1C, various embodiments of an ultrasound system 20 includes a hand wand (e.g., handpiece) 100, module (e.g., transducer module, cartridge, probe) 200, and a controller (e.g., console) 300. In some embodiments, a console 300 comprises a communication system (e.g., wifi, Bluetooth, modem, etc. to communicate with another party, a manufacturer, a supplier, a service provider, the Internet, and/or a cloud. In some embodiments, a cart 301 provides mobility and/or position of the system 20, and can include wheels, surfaces to write on or place components, and/or compartments 302 (e.g., drawers, containers, shelves, etc.) to, for example, store or organize components. In some embodiments, the cart has a power supply, such as a power connection to a battery and/or one or more cords to connect power, communications (e.g., Ethernet) to the system 20. In some embodiments, the system 20 comprises a cart 301. In some embodiments, the system 20 does not comprise a cart 301. The hand wand 100 can be coupled to the controller 300 by an interface 130, which may be a wired or wireless interface. The interface 130 can be coupled to the hand wand 100 by a connector 145. The distal end of the interface 130 can be connected to a controller connector on a circuit 345 (not shown). In one embodiment, the interface 130 can transmit controllable power from the controller 300 to the hand wand 100. In an embodiment, the system 20 has multiple imaging channels (e.g., 8 channels) for ultra-clear HD (high definition) visualization of subcutaneous structures to improve imaging. In an embodiment, the system 20 multiple therapy channels (e.g., 8 channels) and a precision linear-drive motor that doubles treatment accuracy while increasing speed (e.g., by 25%, 40%, 50%, 60%, 75%, 100% or more). Together, these features establish one of the most versatile system platforms in the industry and provide a foundation for unprecedented future possibilities.

In various embodiments, the controller 300 can be adapted to and/or configured for operation with the hand wand 100 and the module 200, as well as the overall ultrasound system 20 functionality. In various embodiments, multiple controllers 300, 300', 300'', etc. can be adapted to and/or configured for operation with multiple hand wands 100, 100', 100'', etc. and or multiple modules 200, 200', 200'', etc. The controller 300 can include connectivity to one or more interactive graphical display 310, which can include a touchscreen monitor and Graphic User Interface (GUI) that allows the user to interact with the ultrasound system 20. In one embodiment, a second smaller, more mobile display that allows the user to more easily position and view the treatment screen. In one embodiment, a second display that allows the system user to view a treatment screen (e.g., on a wall, on a mobile device, large screen, remote screen). In one embodiment the graphical display 310 includes a touchscreen interface 315 (not shown). In various embodiments, the display 310 sets and displays the operating conditions, including equipment activation status, treatment parameters, system messages and prompts, and ultrasound images. In various embodiments, the controller 300 can be adapted to and/or configured to include, for example, a microprocessor with software and input/output devices, systems and devices for controlling electronic and/or mechanical scanning and/or multiplexing of transducers and/or multiplexing of transducer modules, a system for power delivery, systems for monitoring, systems for sensing the spatial position of the probe and/or transducers and/or multiplexing of transducer modules, and/or systems for handling user input and recording treatment results, among others. In various embodiments, the controller 300 can include a system processor and various analog and/or digital control logic, such as one or more of microcontrollers, microprocessors, field-programmable gate arrays, computer boards, and associated components, including firmware and control software, which may be capable of interfacing with user controls and interfacing circuits as well as input/output circuits and systems for communications, displays, interfacing, storage, documentation, and other useful functions. System software running on the system process may be adapted to and/or configured to control all initialization, timing, level setting, monitoring, safety monitoring, and all other ultrasound system functions for accomplishing user-defined treatment objectives. Further, the controller 300 can include various input/output modules, such as switches, buttons, etc., that may also be suitably adapted to and/or configured to control operation of the ultrasound system 20.

In one embodiment, the hand wand 100 includes one or more finger activated controllers or switches, such as 150 and 160. In various embodiments, one or more thermal treatment controllers 160 (e.g., switch, button) activates and/or stops treatment. In various embodiments, one or more imaging controllers 150 (e.g., switch, button) activates and/or stops imaging. In one embodiment, the hand wand 100 can include a removable module 200. In other embodiments, the module 200 may be non-removable. In various embodiments, the module 200 can be mechanically coupled to the hand wand 100 using a latch or coupler 140. In various embodiments, an interface guide 235 or multiple interface guides 235 can be used for assisting the coupling of the module 200 to the hand wand 100. The module 200 can include one or more ultrasound transducers 280. In some embodiments, an ultrasound transducer 280 includes one or more ultrasound elements. The module 200 can include one or more ultrasound elements. The hand wand 100 can include imaging-only modules, treatment-only modules, imaging-and-treatment modules, and the like. In various embodiments, the ultrasound transducer 280 is movable in one or more directions 290 within the module 200. The transducer 280 is connected to a motion mechanism 400. In various embodiments, the motion mechanism comprises zero, one, or more bearings, shafts, rods, screws, lead screws 401, encoders 402 (e.g., optical encoder to measure position of the transducer 280), motors 403 (e.g., a step motor) to help ensure accurate and repeatable movement of the transducer 280 within the module 200. In various embodiments, module 200 can include a transducer 280 which can emit energy through an acoustically transparent member 230. In one embodiment, the control module 300 can be coupled to the hand wand 100 via the interface 130, and the graphic user interface 310 can be adapted to and/or configured for controlling the module 200. In one embodiment, the control module 300 can provide power to the hand wand 100. In one embodiment, the hand wand 100 can include a power source. In one embodiment, the switch 150 can be adapted to and/or configured for controlling a tissue imaging function and the switch 160 can be adapted to and/or configured for controlling a tissue treatment function. In various embodiments, delivery of emitted energy 50 at a suitable focal depth, distribution, timing, and energy level is provided by the module 200 through controlled operation by the control system 300 of the transducer 280 to achieve the desired therapeutic effect with a thermal coagulation zone 550.

In one embodiment, the module 200 can be coupled to the hand wand 100. The module 200 can emit and receive energy, such as ultrasonic energy. The module 200 can be electronically coupled to the hand wand 100 and such coupling may include an interface which is in communication with the controller 300. In one embodiment, the interface guide 235 can be adapted to and/or configured to provide electronic communication between the module 200 and the hand wand 100. The module 200 can comprise various probe and/or transducer configurations. For example, the module 200 can be adapted to and/or configured for a combined dual-mode imaging/therapy transducer, coupled or co-housed imaging/therapy transducers, separate therapy and imaging probes, and the like. In one embodiment, when the module 200 is inserted into or connected to the hand wand 100, the controller 300 automatically detects it and updates the interactive graphical display 310.

In some embodiments, an access key 320 (e.g., a secure USB drive, key) is removably connected to a system 20 to permit the system 20 to function. In various embodiments, the access key is programmed to be customer specific, and serves multiple functions, including system security, country/region specific access to treatment guidelines and functionality, software upgrades, support log transfers and/or credit transfer and/or storage. In various embodiments, the system 20 has internet and/or data connectivity. In an embodiment, connectivity provides a method by which data is transferred between the system 20 provider and the customer. In various embodiments, data includes credits, software updates and support logs. Connectivity is divided into different model embodiments, based on how a user's console is connected to the internet. In one embodiment, Disconnected Model connectivity comprises a console that is disconnected from the internet and customer doesn't have internet access. Credit transfers and software upgrades are conducted by shipping access key(s), (e.g., USB drives) to the customer. In one embodiment, Semi-Connected Model connectivity comprises a console that is disconnected from the internet but customer has internet access. Credit transfers, software upgrades and support log transfers are conducted using the customer's personal computer, smart phone, or other computing device in conjunction with the system access key to transfer data. In one embodiment, Fully-Connected Model connectivity comprises a console that is wirelessly connected to the internet using wifi, cellular modem, Bluetooth, or other protocol. Credit transfers, software upgrades and support log transfers are made directly between the console and the cloud. In various embodiments, the system 20 connects to an online portal, for streamlined inventory management, on-demand treatment purchases and business analytics insights to drive customer aesthetic treatment business to the next level.

Figure 2:
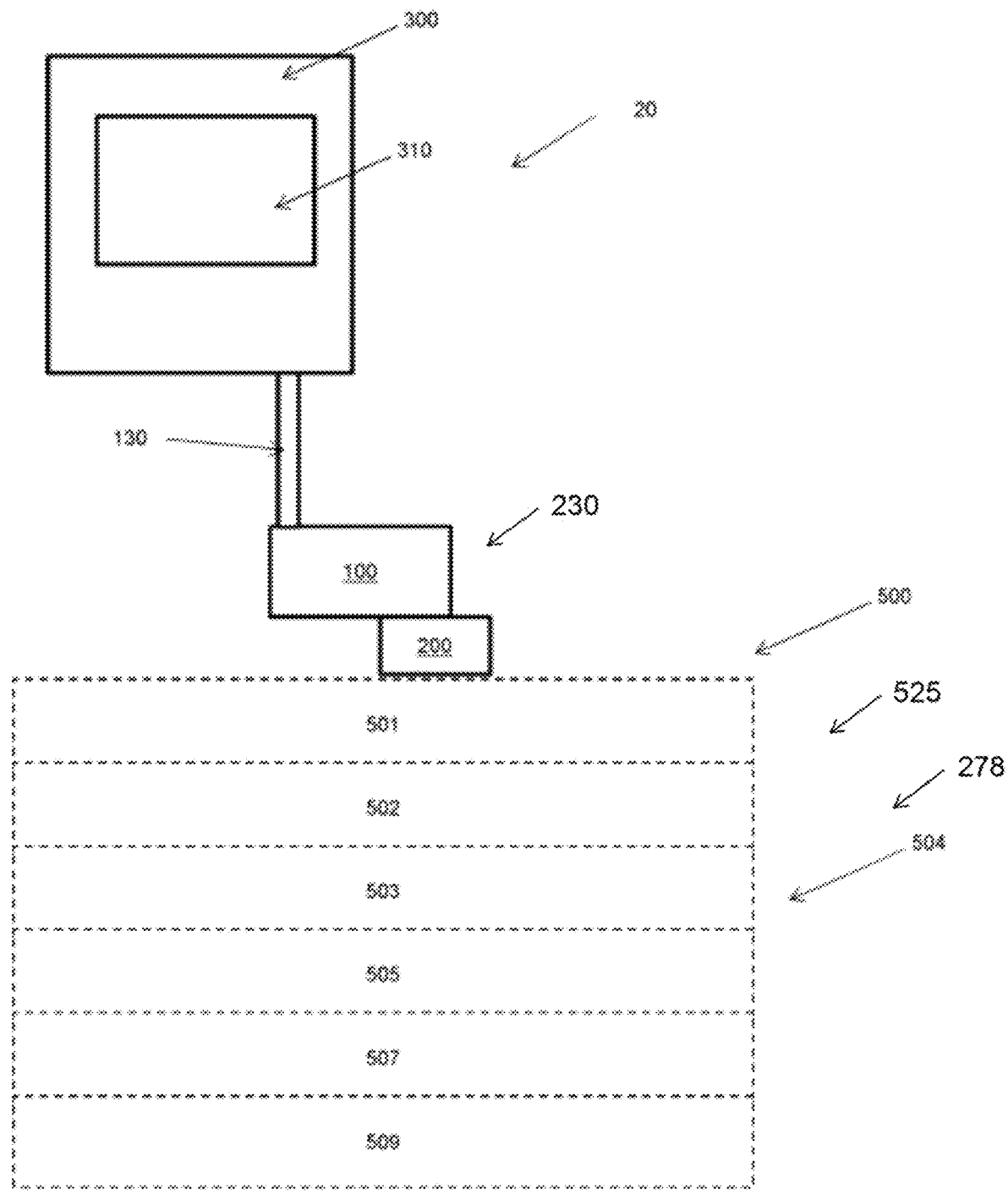
FIG. 2 is a schematic illustration of an ultrasound system coupled to a region of interest according to various embodiments of the present invention.

In various embodiments, tissue below or even at a skin surface such as epidermis, dermis, hypodermis, fascia, and superficial muscular aponeurotic system ("SMAS"), and/or muscle are treated non-invasively with ultrasound energy. Tissue may also include blood vessels and/or nerves. The ultrasound energy can be focused, unfocused or defocused and applied to a region of interest containing at least one of epidermis, dermis, hypodermis, fascia, and SMAS to achieve a therapeutic effect. FIG. 2 is a schematic illustration of the ultrasound system 20 coupled to a region of interest 10. In various embodiments, tissue layers of the region of interest 10 can be at any part of the body of a subject. In one embodiment, the tissue layers are in the head and face region of the subject. The cross-sectional portion of the tissue of the region of interest 10 includes a skin surface 501, an epidermal layer 502, a dermal layer 503, a fat layer 505, a superficial muscular aponeurotic system 507 (hereinafter "SMAS 507"), and a muscle layer 509. The tissue can also include the hypodermis 504, which can include any tissue below the dermal layer 503. The combination of these layers in total may be known as subcutaneous tissue 510. Also illustrated in FIG. 2 is a treatment zone 525 which is below the surface 501. In one embodiment, the surface 501 can be a surface of the skin of a subject 500. Although an embodiment directed to therapy at a tissue layer may be used herein as an example, the system can be applied to any tissue in the body. In various embodiments, the system and/or methods may be used on tissue (including but not limited to one or a combination of muscles, fascia, SMAS, dermis, epidermis, fat, adipose cells, cellulite, which may be called gynoid lipodystrophy, (e.g., non-dimple type female gynoid lipodystrophy), collagen, skin, blood vessels, of the face, neck, head, arms, legs, or any other location on or in the body (including bodily cavities). In various embodiments, cellulite (e.g., non-dimple type female gynoid lipodystrophy) reduction is achieved in an amount of 2%, 5%, 10%, 15%, 20%, 25%, 30%, 40%, 50%, 75%, 80%, 90%, 95%, and any ranges therein.

Figure 3:
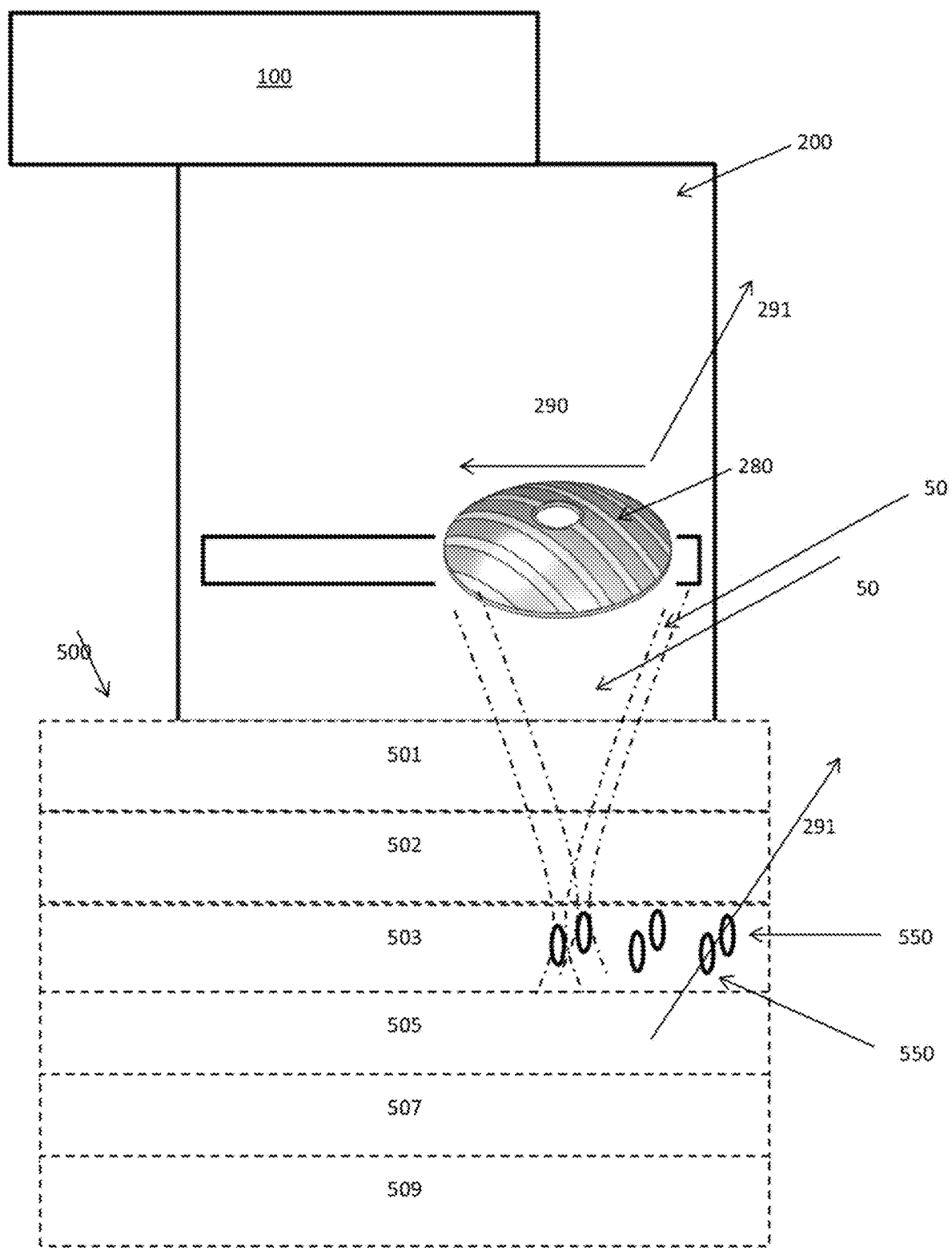
FIG. 3 is a schematic illustration of a portion of a transducer according to various embodiments of the present invention.

With reference to the illustration in FIG. 2, an embodiment of the ultrasound system 20 includes the hand wand 100, the module 200, and the controller 300. In one embodiment, the module 200 includes a transducer 280. FIG. 3 illustrates an embodiment of an ultrasound system 20 with a transducer 280 adapted to and/or configured to treat tissue at a focal depth 278. In one embodiment, the focal depth 278 is a distance between the transducer 280 and the target tissue for treatment. In one embodiment, a focal depth 278 is fixed for a given transducer 280. In one embodiment, a focal depth 278 is variable for a given transducer 280. In one embodiment, a transducer 280 is configured to treat simultaneously at multiple depths below a skin surface (e.g., 1.5 mm, 3.0 mm, 4.5 mm, or other depths).

Figure 4:
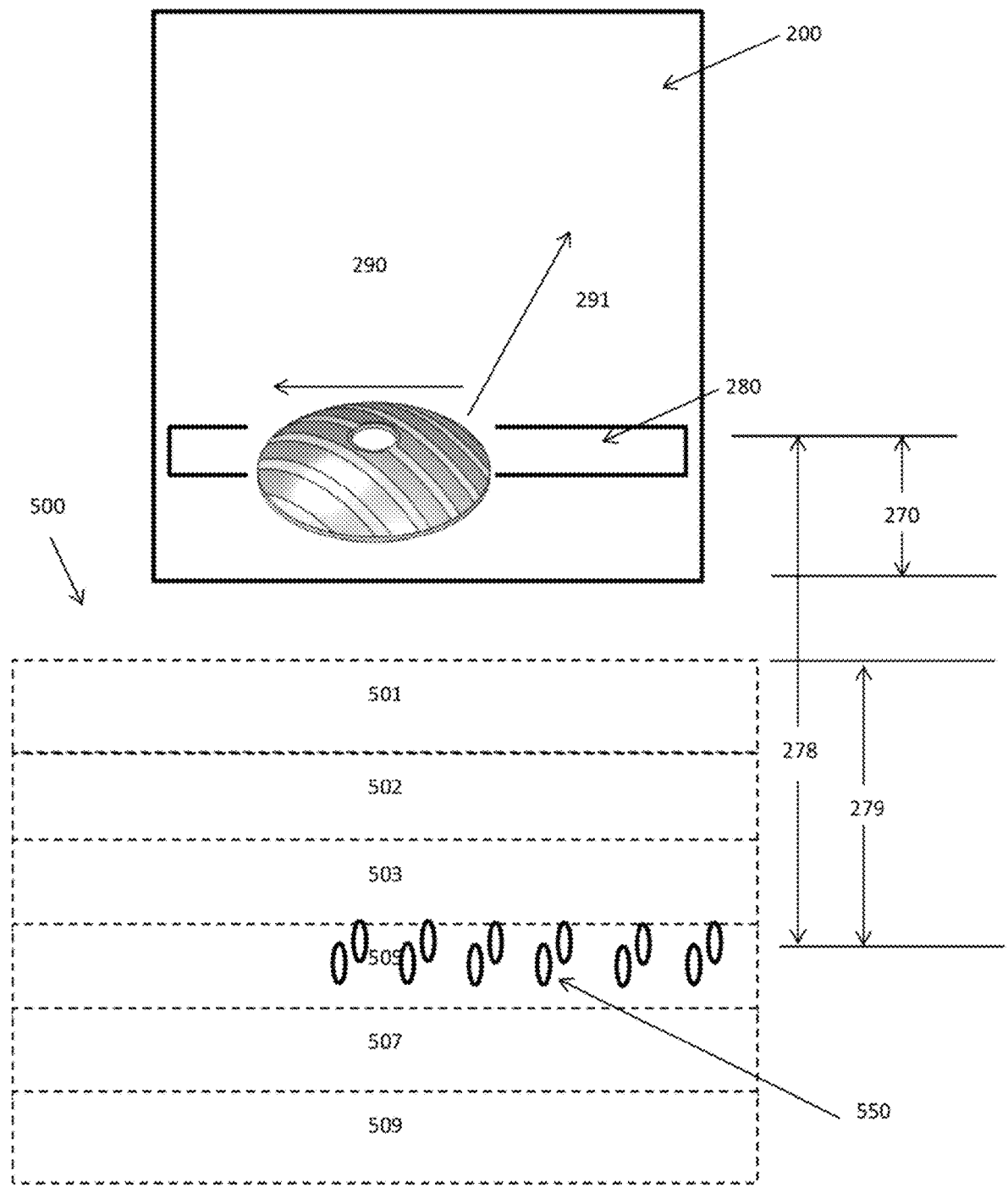
FIG. 4 is a partial cut away side view of an ultrasound system according to various embodiments of the present invention.

With reference to the illustration in FIG. 4, the module 200 can include a transducer 280 which can emit energy through an acoustically transparent member 230. In various embodiments, a depth may refer to the focal depth 278. In one embodiment, the transducer 280 can have an offset distance 270, which is the distance between the transducer 280 and a surface of the acoustically transparent member 230. In one embodiment, the focal depth 278 of a transducer 280 is a fixed distance from the transducer. In one embodiment, a transducer 280 may have a fixed offset distance 270 from the transducer to the acoustically transparent member 230. In one embodiment, an acoustically transparent member 230 is adapted to and/or configured at a position on the module 200 or the ultrasound system 20 for contacting the skin surface 501. In various embodiments, the focal depth 278 exceeds the offset distance 270 by an amount to correspond to treatment at a target area located at a tissue depth 279 below a skin surface 501. In various embodiments, when the ultrasound system 20 placed in physical contact with the skin surface 501, the tissue depth 279 is a distance between the acoustically transparent member 230 and the target area, measured as the distance from the portion of the hand wand 100 or module 200 surface that contacts skin (with or without an acoustic coupling gel, medium, etc.) and the depth in tissue from that skin surface contact point to the target area. In one embodiment, the focal depth 278 can correspond to the sum of an offset distance 270 (as measured to the surface of the acoustically transparent member 230 in contact with a coupling medium and/or skin 501) in addition to a tissue depth 279 under the skin surface 501 to the target region. In various embodiments, the acoustically transparent member 230 is not used.

Coupling components can comprise various substances, materials, and/or devices to facilitate coupling of the transducer 280 or module 200 to a region of interest. For example, coupling components can comprise an acoustic coupling system adapted to and/or configured for acoustic coupling of ultrasound energy and signals. Acoustic coupling system with possible connections such as manifolds may be utilized to couple sound into the region of interest, provide liquid- or fluid-filled lens focusing. The coupling system may facilitate such coupling through use of one or more coupling media, including air, gases, water, liquids, fluids, gels, solids, non-gels, and/or any combination thereof, or any other medium that allows for signals to be transmitted between the transducer 280 and a region of interest. In one embodiment one or more coupling media is provided inside a transducer. In one embodiment a fluid-filled module 200 contains one or more coupling media inside a housing. In one embodiment a fluid-filled module 200 contains one or more coupling media inside a sealed housing, which is separable from a dry portion of an ultrasonic device. In various embodiments, a coupling medium is used to transmit ultrasound energy between one or more devices and tissue with a transmission efficiency of 100%, 99% or more, 98% or more, 95% or more, 90% or more, 80% or more, 75% or more, 60% or more, 50% or more, 40% or more, 30% or more, 25% or more, 20% or more, 10% or more, and/or 5% or more.

In various embodiments, the transducer 280 can image and treat a region of interest at any suitable tissue depths 279. In one embodiment, the transducer module 280 can provide an acoustic power in a range of about 1 W or less, between about 1 W to about 100 W, and more than about 100 W, e.g., 200 W, 300 W, 400 W, 500 W. In one embodiment, the transducer module 280 can provide an acoustic power at a frequency of about 1 MHz or less, between about 1 MHz to about 10 MHz (e.g., 3 MHz, 4 MHz, 4.5 MHz, 7 MHz, 10 MHz), and more than about 10 MHz. In one embodiment, the module 200 has a focal depth 278 for a treatment at a tissue depth 279 of about 4.5 mm below the skin surface 501. In one embodiment, the module 200 has a focal depth 278 for a treatment at a tissue depth 279 of about 3 mm below the skin surface 501. In one embodiment, the module 200 has a focal depth 278 for a treatment at a tissue depth 279 of about 1.5 mm below the skin surface 501. Some non-limiting embodiments of transducers 280 or modules 200 can be adapted to and/or configured for delivering ultrasonic energy at a tissue depth of 1.5 mm, 3 mm, 4.5 mm, 6 mm, 7 mm, less than 3 mm, between 3 mm and 4.5 mm, between 4.5 mm and 6 mm, more than more than 4.5 mm, more than 6 mm, etc., and anywhere in the ranges of 0-3 mm, 0-4.5 mm, 0-6 mm, 0-25 mm, 0-100 mm, etc. and any depths therein. In one embodiment, the ultrasound system 20 is provided with two or more transducer modules 280. For example, a first transducer module can apply treatment at a first tissue depth (e.g., about 4.5 mm) and a second transducer module can apply treatment at a second tissue depth (e.g., of about 3 mm), and a third transducer module can apply treatment at a third tissue depth (e.g., of about 1.5-2 mm). In one embodiment, at least some or all transducer modules can be adapted to and/or configured to apply treatment at substantially same depths.

In various embodiments, changing the number of focus point locations (e.g., such as with a tissue depth 279) for an ultrasonic procedure can be advantageous because it permits treatment of a patient at varied tissue depths even if the focal depth 278 of a transducer 270 is fixed. This can provide synergistic results and maximizing the clinical results of a single treatment session. For example, treatment at multiple depths under a single surface region permits a larger overall volume of tissue treatment, which results in enhanced collagen formation and tightening. Additionally, treatment at different depths affects different types of tissue, thereby producing different clinical effects that together provide an enhanced overall cosmetic result. For example, superficial treatment may reduce the visibility of wrinkles and deeper treatment may induce formation of more collagen growth. Likewise, treatment at various locations at the same or different depths can improve a treatment.

Although treatment of a subject at different locations in one session may be advantageous in some embodiments, sequential treatment over time may be beneficial in other embodiments. For example, a subject may be treated under the same surface region at one depth in time one, a second depth in time two, etc. In various embodiments, the time can be on the order of nanoseconds, microseconds, milliseconds, seconds, minutes, hours, days, weeks, months, or other time periods. The new collagen produced by the first treatment may be more sensitive to subsequent treatments, which may be desired for some indications. Alternatively, multiple depth treatment under the same surface region in a single session may be advantageous because treatment at one depth may synergistically enhance or supplement treatment at another depth (due to, for example, enhanced blood flow, stimulation of growth factors, hormonal stimulation, etc.). In several embodiments, different transducer modules provide treatment at different depths. In one embodiment, a single transducer module can be adjusted or controlled for varied depths. Safety features to minimize the risk that an incorrect depth will be selected can be used in conjunction with the single module system.

In several embodiments, a method of treating the lower face and neck area (e.g., the submental area) is provided. In several embodiments, a method of treating (e.g., softening) mentolabial folds is provided. In other embodiments, a method of treating the eye region (e.g., malar bags, treat infraorbital laxity) is provided. Upper lid laxity improvement and periorbital lines and texture improvement will be achieved by several embodiments by treating at variable depths. By treating at varied locations in a single treatment session, optimal clinical effects (e.g., softening, tightening) can be achieved. In several embodiments, the treatment methods described herein are non-invasive cosmetic procedures. In some embodiments, the methods can be used in conjunction with invasive procedures, such as surgical facelifts or liposuction, where skin tightening is desired. In various embodiments, the methods can be applied to any part of the body.

In one embodiment, a transducer module 200 permits a treatment sequence at a fixed depth at or below the skin surface. In one embodiment, a transducer module permits a treatment sequence at one, two, or more variable or fixed depths below the dermal layer. In several embodiments, the transducer module comprises a movement mechanism adapted to and/or configured to direct ultrasonic treatment in a sequence of individual thermal lesions (hereinafter "thermal coagulation points" or "TCPs") at a fixed focal depth. In one embodiment, the sequence of individual TCPs has a treatment spacing in a range from about 0.01 mm to about 25 mm (e.g., 1 mm, 1.5 mm, 2 mm, 2.5 mm, 3 mm, 5 mm, 10 mm, 20 mm and any value ranges therein), with a dithering alteration of the spacing by 1-50% (e.g., 1%, 5%, 10%, 15%, 20%, 25%, 30%, 35%, 40%, 45%, 50% and any range therein). For example, the spacing can be 1.1 mm or less, 1.5 mm or more, between about 1.1 mm and about 1.5 mm, etc. In one embodiment, the individual TCPs are discrete. In one embodiment, the individual TCPs are overlapping. In one embodiment, the movement mechanism is adapted to and/or configured to be programmed to provide variable spacing between the individual TCPs. In one embodiment, the dithering can be adapted to and/or configured to provide variable spacing between the individual TCPs. In several embodiments, a transducer module comprises a movement mechanism adapted to and/or configured to direct ultrasonic treatment in a sequence so that TCPs are formed in linear or substantially linear sequences separated by a treatment distance. For example, a transducer module can be adapted to and/or configured to form TCPs along a first linear sequence and a second linear sequence separated by a treatment distance from the first linear sequence. In one embodiment, treatment distance between adjacent linear sequences of individual TCPs is in a range from about 0.01 mm to about 25 mm. In one embodiment, treatment distance between adjacent linear sequences of individual TCPs is in a range from about 0.01 mm to about 50 mm. For example, the treatment distance can be 2 mm or less, 3 mm or more, between about 2 mm and about 3 mm, etc. In several embodiments, a transducer module can comprise one or more movement mechanisms 400 adapted to and/or configured to direct ultrasonic treatment in a sequence so that TCPs are formed in linear or substantially linear sequences of individual thermal lesions separated by a treatment distance from other linear sequences. In one embodiment a treatment is applied in a first direction 290 (e.g., push). In one embodiment, a treatment is applied opposite the first direction 290 (e.g., pull). In one embodiment, treatment is applied in both a first direction 290 and opposite the first direction (e.g., push and pull). In one embodiment, the treatment distance separating linear or substantially linear TCPs sequences is the same or substantially the same. In one embodiment, the treatment distance separating linear or substantially linear TCPs sequences is different or substantially different for various adjacent pairs of linear TCPs sequences.

In one embodiment, first and second removable transducer modules are provided. In one embodiment, each of the first and second transducer modules are adapted to and/or configured for both ultrasonic imaging and ultrasonic treatment. In one embodiment, a transducer module is adapted to and/or configured for treatment only. In one embodiment, an imaging transducer may be attached to a handle of a probe or a hand wand. The first and second transducer modules are adapted to and/or configured for interchangeable coupling to a hand wand. The first transducer module is adapted to and/or configured to apply ultrasonic therapy to a first layer of tissue, while the second transducer module is adapted to and/or configured to apply ultrasonic therapy to a second layer of tissue. The second layer of tissue is at a different depth than the first layer of tissue.

As illustrated in FIG. 3, in various embodiments, delivery of emitted energy 50 at a suitable focal depth 278, distribution, timing, and energy level is provided by the module 200 through controlled operation by the control system 300 to achieve the desired therapeutic effect of controlled thermal injury to treat at least one of the epidermis layer 502, dermis layer 503, fat layer 505, the SMAS layer 507, the muscle layer 509, and/or the hypodermis 504. FIG. 3 illustrates one embodiment of a depth that corresponds to a depth for treating muscle. In various embodiments, the depth can correspond to any tissue, tissue layer, skin, epidermis, dermis, hypodermis, fat, SMAS, muscle, blood vessel, nerve, or other tissue. During operation, the module 200 and/or the transducer 280 can also be mechanically and/or electronically scanned along the surface 501 to treat an extended area. Before, during, and after the delivery of ultrasound energy 50 to at least one of the epidermis layer 502, dermis layer 503, hypodermis 504, fat layer 505, the SMAS layer 507 and/or the muscle layer 509, monitoring of the treatment area and surrounding structures can be provided to plan and assess the results and/or provide feedback to the controller 300 and the user via a graphical interface 310.

In one embodiment, an ultrasound system 20 generates ultrasound energy which is directed to and focused below the surface 501. This controlled and focused ultrasound energy 50 creates the thermal coagulation point or zone (TCP) 550. In one embodiment, the ultrasound energy 50 creates a void in subcutaneous tissue 510. In various embodiments, the emitted energy 50 targets the tissue below the surface 501 which cuts, ablates, coagulates, micro-ablates, manipulates, and/or causes a TCP 550 in the tissue portion 10 below the surface 501 at a specified focal depth 278. In one embodiment, during the treatment sequence, the transducer 280 moves in a direction denoted by the arrow marked 290 at specified intervals 295 to create a series of treatment zones 254 each of which receives an emitted energy 50 to create one or more TCPs 550. In one embodiment, an arrow marked 291 illustrates an axis or direction that is orthogonal to arrow 290, and a spacing of TCP's 550 show TCP's can be spaced orthogonally to the motion direction of the transducer 280. In some embodiments, an orientation of the spaced TCP's can be set at any angle 0-180 degrees from arrow 290. In some embodiments, an orientation of the spaced TCP's can be set at any angle 0-180 degrees based on the orientation of poled areas on the transducer 280.

In various embodiments, transducer modules can comprise one or more transduction elements. The transduction elements can comprise a piezoelectrically active material, such as lead zirconante titanate (PZT), or any other piezoelectrically active material, such as a piezoelectric ceramic, crystal, plastic, and/or composite materials, as well as lithium niobate, lead titanate, barium titanate, and/or lead metaniobate. In various embodiments, in addition to, or instead of, a piezoelectrically active material, transducer modules can comprise any other materials adapted to and/or configured for generating radiation and/or acoustical energy. In various embodiments, transducer modules can be adapted to and/or configured to operate at different frequencies and treatment depths. Transducer properties can be defined by an outer diameter ("OD") and focal length ($F_L$). In one embodiment, a transducer can be adapted to and/or configured to have OD=19 mm and $F_L$=15 mm. In other embodiments, other suitable values of OD and $F_L$ can be used, such as OD of less than about 19 mm, greater than about 19 mm, etc. and $F_L$ of less than about 15 mm, greater than about 15 mm, etc. Transducer modules can be adapted to and/or configured to apply ultrasonic energy at different target tissue depths. As described above, in several embodiments, transducer modules comprise movement mechanisms adapted to and/or configured to direct ultrasonic treatment in a linear or substantial liner sequence of individual TCPs with a treatment spacing between individual TCPs. For example, treatment spacing can be about 1.1 mm, 1.5 mm, etc. In several embodiments, transducer modules can further comprise movement mechanisms adapted to and/or configured to direct ultrasonic treatment in a sequence so that TCPs are formed in linear or substantially linear sequences separated by a treatment spacing. For example, a transducer module can be adapted to and/or configured to form TCPs along a first linear sequence and a second linear sequence separated by treatment spacing between about 2 mm and 3 mm from the first linear sequence. In one embodiment, a user can manually move the transducer modules across the surface of a treatment area so that adjacent linear sequences of TCPs are created. In one embodiment, a movement mechanism can automatically move the transducer modules across the surface of a treatment area so that adjacent linear sequences of TCPs are created.

Aperture Spatial Frequency Analysis and Fourier Transform

In various embodiments, spatial frequency analysis techniques based on Fourier analysis and Fourier optics can be used to increase efficiency of therapeutic treatment. When a system that has an impulse response h(t) is excited by a stimulus x(t), the relationship between the input x(t) and output y(t) is related by the convolution function as follows:

$$y(t)=x(t)*h(t)=\int_{-\infty}^{\infty}x(\tau)h(t-\tau)d\tau \quad (1)$$

In various embodiments, Fourier transform can be applied to compute the convolution of equation (1). Continuous one-dimensional Fourier transform can be defined at:

$$y(f)=F(y(t))=\int_{-\infty}^{\infty}y(t)e^{-j2\pi ft}dt \quad (2)$$

Here f is frequency, t is time. It can be shown that convolution in the time domain is equivalent to multiplication in the frequency domain:

$$F(x(t)*h(t))=X(f)H(f)=Y(f) \quad (3)$$

In various embodiments, the Fraunhofer approximation can be used for deriving a relationship between a transducer opening or aperture and a resulting ultrasonic beam response. Derivation of the Fraunhofer approximation is described in Joseph Goodman, Introduction to Fourier Optics (3d ed. 2004), which is incorporated in its entirety by reference, herein. According to the Fraunhofer approximation, a far-field complex amplitude pattern produced by a complex aperture is equal to a two-dimensional Fourier transform of the aperture amplitude and phase. In several embodiments, this relationship in optics can be extended to ultrasound since linear wave equations can be used to represent both light propagation and sound propagation. In the case of optics and/or ultrasound, the two-dimensional Fourier transform can determine a sound wave pressure amplitude distribution at the focus of a transducer.

For a focused system, the variable z which represents depth can be replaced with $z_f$ which represents a focal distance.

$$f_x = \frac{x_0}{\lambda z_f} \quad (4a)$$

$$f_y = \frac{y_0}{\lambda z_f} \quad (4b)$$

In various embodiments, Fourier optics and Fourier transform identities (some of which are listed in Table 1, below) can be used for ultrasound transducers in order to determine the intensity distribution corresponding to a transducer design. For example, Fourier transform of a rectangle rect (ax) is a sinc function. As another example, Fourier transform of a two dimensional circle of uniform amplitude is a first order Bessel function which can be represented as $J_1$.

TABLE 1

| | Aperture Function | Fourier Transform |
|---|---|---|
| 1 | rect(ax) | $\frac{1}{|a|}\text{sinc}\left(\frac{\xi}{a}\right)$ |
| 2 | $\delta(x)$ | 1 |
| 3 | cos(ax) | $\frac{\delta\left(\xi - \frac{a}{2\pi}\right)+\delta\left(\xi + \frac{a}{2\pi}\right)}{2}$ |
| 4 | sin(ax) | $\frac{\delta\left(\xi - \frac{a}{2\pi}\right)-\delta\left(\xi + \frac{a}{2\pi}\right)}{2j}$ |
| 5 (two-dimensional transform pair) | circ($\sqrt{x^2+y^2}$) | $\frac{j_1\left(2\pi\sqrt{\xi_x^2+\xi_y^2}\right)}{\sqrt{\xi_x^2+\xi_y^2}}$ |
| 6 | f(x) * g(x) | $F(\xi)G(\xi)$ |
| 7 | f(x)g(x) | $F(\xi) * G(\xi)$ |

In several embodiments, an ultrasound transducer can have a rectangular aperture of suitable dimensions and focal length. In several embodiments, an ultrasound transducer can have a circular aperture with suitable dimensions and focal length. In one embodiment, a transducer can have a circular aperture with an outer radius of approximately 9.5 mm, an inner diameter of approximately 2 mm, and focal length of approximately 15 mm. The aperture of a circular transducer may be described as:

$$f(x, y) = circ\left(\frac{r}{a}\right) - circ\left(\frac{r}{b}\right) \tag{5a}$$

$$r = \sqrt{x^2 + y^2} \tag{5b}$$

For example, in one embodiment, the variable 'a' can be approximately 9.5 mm and the variable 'b' in equation (5a) can be approximately 2 mm. Applying Fourier transform to equation (5a) can provide an estimate of the sound wave pressure distribution at the focus.

$$F_{x,y}(f(x, y)) = F(\xi_x, \xi_y) = \frac{aJ_1\left(2\pi a\sqrt{\xi_x^2 + \xi_y^2}\right)}{\sqrt{\xi_x^2 + \xi_y^2}} - \frac{bJ_1\left(2\pi b\sqrt{\xi_x^2 + \xi_y^2}\right)}{\sqrt{\xi_x^2 + \xi_y^2}} \tag{6}$$

where $\xi_x$ and $\xi_y$ are same as $f_x$ and $f_y$ of equations (4a) and (4b). Equation (6) demonstrates that the sound wave pressure distribution of a transducer with a circular aperture is a first order Bessel function. In one embodiment, a substantial majority of the energy is concentrated at the focus (e.g., 15 mm away from the aperture). The width of a main ultrasonic beam and the distribution of energy away from the main beam can be expressed as a function of the operating frequency as is expressed in equations (4a) and (4b).

In various embodiments, two identical or nearly identical beams could be created at the focus if the aperture was modulated (e.g., multiplied) by a correct function. In one embodiment, a cosine function can be applied to a circular aperture as follows:

$$g(x, y) = \cos(cx)\left(circ\left(\frac{r}{a}\right) - circ\left(\frac{r}{b}\right)\right) \tag{7}$$

An energy distribution or beam response at the focus of the modulated aperture of equation (7) is the convolution of the Fourier transform of the two functions of the aperture:

$$G(\xi_x, \xi_y) = \left(\frac{\delta\left(\xi_x - \frac{c}{2\pi}\right) + \delta\left(\xi_x + \frac{c}{2\pi}\right)}{2}\right) * F(\xi_x, \xi_y) \tag{8}$$

Equation (8) can be simplified into the summation of two separate functions applying the Fourier Transform identity for a Dirac delta function (e.g., identity 2 in Table 2):

$$G(\xi_x, \xi_y) = \frac{1}{2}\left(F\left(\xi_x - \frac{c}{2\pi}, \xi_y\right) + F\left(\xi_x + \frac{c}{2\pi}, \xi_y\right)\right) \tag{9}$$

Equation (9) shows that two beams appearing at the focus are spatially shifted by $$\pm\frac{c}{2\pi}$$

compared to the original, non-modulated beam. In several embodiments, one or more other modulation functions, such as sine function, can be used to achieve a desired beam response. In several embodiments, aperture can be modulated such that more than two foci are created. For example, three, four, five, etc. foci can be created. In several embodiments, aperture can be modulated such that foci are created sequentially or substantially sequentially rather than simultaneously.

In several embodiments, therapy transducer modules comprise movement mechanisms configured to direct ultrasonic treatment in a linear or substantial liner sequence of individual TCPs with a treatment spacing between individual TCPs. For example, treatment spacing can be about 1.1 mm, 1.5 mm, etc. In several embodiments, transducer modules can further comprise movement mechanisms configured to direct ultrasonic treatment in a sequence so that TCPs are formed in linear or substantially linear sequences separated by a treatment spacing. For example, a transducer module can be configured to form TCPs along a first linear sequence and a second linear sequence separated by treatment spacing between about 2 mm and 3 mm from the first linear sequence. According to equation (9), a simultaneous or substantially simultaneous split in the ultrasonic beam may be achieved at the focus (or before the focus) if the aperture is modulated by a cosine and/or sine function of a desired spatial frequency. In one embodiment, two simultaneous or nearly simultaneous focused beams separated by about 1.1 mm treatment spacing can be created in a linear or substantially linear sequence. At 7 MHz frequency of ultrasound, the wavelength λ of ultrasound wave in water is approximately 0.220 mm. Accordingly, spatial frequencies $\xi_x$ and $\xi_y$ at the focus are represented as:

$$\xi_x = \frac{x_o}{15*0.220} = \frac{x_0}{3.3} \tag{10a}$$

$$\xi_y = \frac{y_0}{15*0.220} = \frac{y_0}{3.3} \tag{10b}$$

In order to place two foci separated by about 1.1 mm, then the spatial frequency for modulating the aperture is calculated as follows. Using identities 3 and 4 in Table 2, the Fourier transformation of a sine or cosine function is a Dirac delta function with the argument:

$$\arg = \frac{x_0}{3.3} - \frac{k_x}{2\pi} \tag{11a}$$

In one embodiment, equation (11a) can solved for $k_x$ when argument is 0:

$$k_x = \frac{2\pi x_0}{3.3} \tag{11b}$$

Further, $x_o$ can be replaced by half of the separation distance (e.g., 1.1 mm):

$$k_x = \frac{2\pi\frac{s}{2}}{z_f\lambda} = \frac{2\pi\frac{1.1}{2}}{3.5} = 1.04 \text{ mm}^{-1} \tag{11c}$$

In several embodiments, a transducer with circular aperture emitting ultrasonic energy at various operating frequencies can be modulated by a sine and/or cosine functions at spatial frequencies listed in Table 2. Modulated aperture of the transducer can produce a simultaneously or substantially simultaneously split beam with two foci having different separation distances, as is indicated in Table 2. In one embodiment, the transducer can have OD of about 19 mm and a focal length of about 15 mm.

TABLE 2

| Ultrasound Frequency | Separation Distance Between Foci | | | |
|---|---|---|---|---|
| | 1.1 mm | 1.5 mm | 2 mm | 3 mm |
| 4 MHz | 0.60 | 0.82 | 1.09 | 1.63 |
| 7 MHz | 1.04 | 1.43 | 1.90 | 2.86 |
| 10 MHz | 1.50 | 2.04 | 2.72 | 3.08 |

As is shown in Table 2, in several embodiments, a spatial frequency of an aperture modulation function increases as the ultrasonic operating frequency increases for a given foci separation distance. In addition, the spatial frequency increases as the desired foci separation distance increases.

In one embodiment, higher spatial frequency can result in amplitude transitions in the aperture occurring more rapidly. Due to transducer processing limitations, rapid amplitude variations in the aperture can make the aperture less efficient as there may be a variance in an amount of sound pressure produced by different parts of the aperture. In one embodiment, using spatial frequencies to simultaneously or nearly simultaneously split the beam can reduce the overall focal gain of each beam. As is shown in equation (9), a field pressure at the focus of each beam is reduced by a factor of two in comparison with an unmodulated beam. In one embodiment, the sound pressure or ultrasound intensity from the aperture can be increased to obtain similar or substantially similar intensities at the focal plane. However, in one embodiment, increasing the pressure at the aperture may not be limited by system and/or transducer processing limitations. In one embodiment, an increase in the pressure at the aperture can increase the overall intensity in the near field, which may increase the possibility of excessively heating treatment area tissue(s) that is located before focus. In one embodiment, the possibility of additional heating of the pre-focal tissue(s) may be limited or eliminated by using a lower ultrasound treatment frequency.

In one embodiment, applying aperture modulation function as is shown in equation (7) results in two simultaneous or substantially simultaneous ultrasound beams at the focus. In various embodiments, ultrasound beam can be split multiple times, such as three, four, five, etc. times, such that multiple simultaneous or nearly simultaneous beams are created. In one embodiment, four equally spaced beams along one dimension can be generated by modulating or multiplying the aperture by two separate spatial frequencies:

$$g(x, y) = (\cos(cx) + \cos(dx))\left(circ\left(\frac{r}{a}\right) - circ\left(\frac{r}{b}\right)\right) \quad (12a)$$

$$G(\xi_x, \xi_y) = \frac{1}{2}\left(F\left(\xi_x - \frac{c}{2\pi}, \xi_y\right) + F\left(\xi_x + \frac{c}{2\pi}, \xi_y\right) + F\left(\xi_x - \frac{d}{2\pi}, \xi_y\right) + F\left(\xi_x - \frac{d}{2\pi}, \xi_y\right)\right) \quad (12b)$$

As is shown in equation (12b), unmodulated beam at the focus can be created at four different locations along the x-axis. In one embodiment, a constant or DC term, C1, may be added to the amplitude modulation function to maintain placement of energy at the original focal location:

$$g(x, y) = (\cos(cx)|\cos(dx)|C_1)\left(circ\left(\frac{r}{a}\right) \quad circ\left(\frac{r}{b}\right)\right) \quad (13a)$$

$$G(\xi_x, \xi_y) = \frac{1}{2}\left(F\left(\xi_x - \frac{c}{2\pi}, \xi_y\right) + F\left(\xi_x + \frac{c}{2\pi}, \xi_y\right) + F\left(\xi_x - \frac{d}{2\pi}, \xi_y\right) + F\left(\xi_x - \frac{d}{2\pi}, \xi_y\right)\right) + C_1 F(\xi_x, \xi_y) \quad (13b)$$

In one embodiment, aperture modulation of equations (12) and (13), whereby the beam can be placed at multiple locations simultaneously or nearly simultaneously, may be have limited applicability due to system, material, and/or tissue limitations. In one embodiment, due to the possibility of heating treatment area tissue(s) located before focus, the frequency of ultrasound therapy may be adjusted, such as lowered, in order to limit and/or eliminate such possibility. In one embodiment, nonlinear techniques can be applied at the focus in order to limit and/or eliminate the possibility of heating of the pre-focal tissue(s). In one embodiment, the sound pressure or ultrasound intensity from the aperture can be increased to obtain similar or substantially similar intensities at the focal plane.

In various embodiments, if the amplitude and phase functions at the aperture are separable, the two-dimensional Fourier transform of a sound pressure function $U(x_1, y_1)$ can be expressed as a product of a one-dimensional Fourier transform of two functions in x and y. In various embodiments, it may be advantageous to create multiple TCPs in a linear or substantially linear sequence as well as to create multiple linear sequences simultaneously or nearly simultaneously.

Electronic Dithering of Multiple Beam Splitting Apertures Using Frequency Modulation In various embodiments, Table 2 illustrates aperture spatial frequency for achieving a specific distance between two simultaneous foci for a given operational frequency (e.g. in various embodiments, 4 MHz, 7 MHz, 10 MHz). Equation (11c) shows that the separation distance between the foci is also a function operational frequency. For example, in one embodiment the spatial frequency of the aperture ($k_x$) is fixed to 1.0 mm$^{-1}$ and the operational frequency is allowed to vary. Equation 11c can be rewritten to show how the foci separation distance can be modulated through operation frequency.

$$s = (k_x z_f v_c)/(\pi f_{op}) \quad (14)$$

where $k_x$ is the spatial frequency in mm$^{-1}$, $z_f$ is the focal depth of the aperture in mm, $v_c$ is the velocity of ultrasound in the propagating medium (e.g. water) in mm/μsec and $f_{op}$ is the operational frequency of the aperture in MHz. In one embodiment, the following substitution is made in equation 11c:

$$\lambda = v_c/f_{op} \quad (15)$$

As Equation (14) shows, the separation distance of the foci is a function of the operational frequency. Further, the rate in change of the separation distance to the operational frequency is:

$$ds/df_{op} = -(k_x z_f v_c)/(\pi f_{op}^2) \quad (16)$$

Equation (16) shows that the separation distance decreases as the operational frequency increases. Table 3 (below) shows the rate in change of separation distance as a function of operational frequency for the different spatial frequencies (e.g., in various embodiments, 4 MHz, 7 MHz, 10 MHz).

TABLE 3

| Ultrasound | Derivative of Equation (16) [mm/MHz] | | | |
|---|---|---|---|---|
| Frequency | 1.1 mm | 1.5 mm | 2 mm | 3 mm |
| 4 MHz | −0.269 | −0.367 | −0.488 | −0.730 |
| 7 MHz | −0.152 | −0.209 | −0.278 | −0.418 |
| 10 MHz | −0.107 | −0.146 | −0.195 | −0.221 |

As shown in Table 3, as the operational frequency increases, the foci get closer together and as the operational frequency decreases the foci get farther apart without the need to change the phase or mechanically move the transducer. This is a unique method of electronically moving the beam to spread the energy without relying on thermal conduction in tissue. The benefits include a reduction or a minimization of the maximum temperature and an increase in the thermal coagulation volume of the lesion without the need for additional system channels.

The amount of movement from a main operational frequency can be determined by using equation (14). In one embodiment, the main operational frequency of an aperture is 5 MHz and the focal length is 15 mm. In some embodiments, the operational frequency is called the aperture center frequency. In one embodiment, the operational frequency is 5 MHz. In one embodiment, Table 4 at FIG. 5 shows the amount of foci separation for apertures with different spatial frequencies ($k_x$=0.5, 1.0, 1.5, 2.0 in $mm^{-1}$) as designed for a center frequency of 5 MHz. It also calculates the amount of spread from the foci of the center frequency at 5 MHz. According to one embodiment, the spacing decreases for higher frequencies relative to 5 MHz and increases for lower frequencies relative to 5 MHz.

Figure 6:
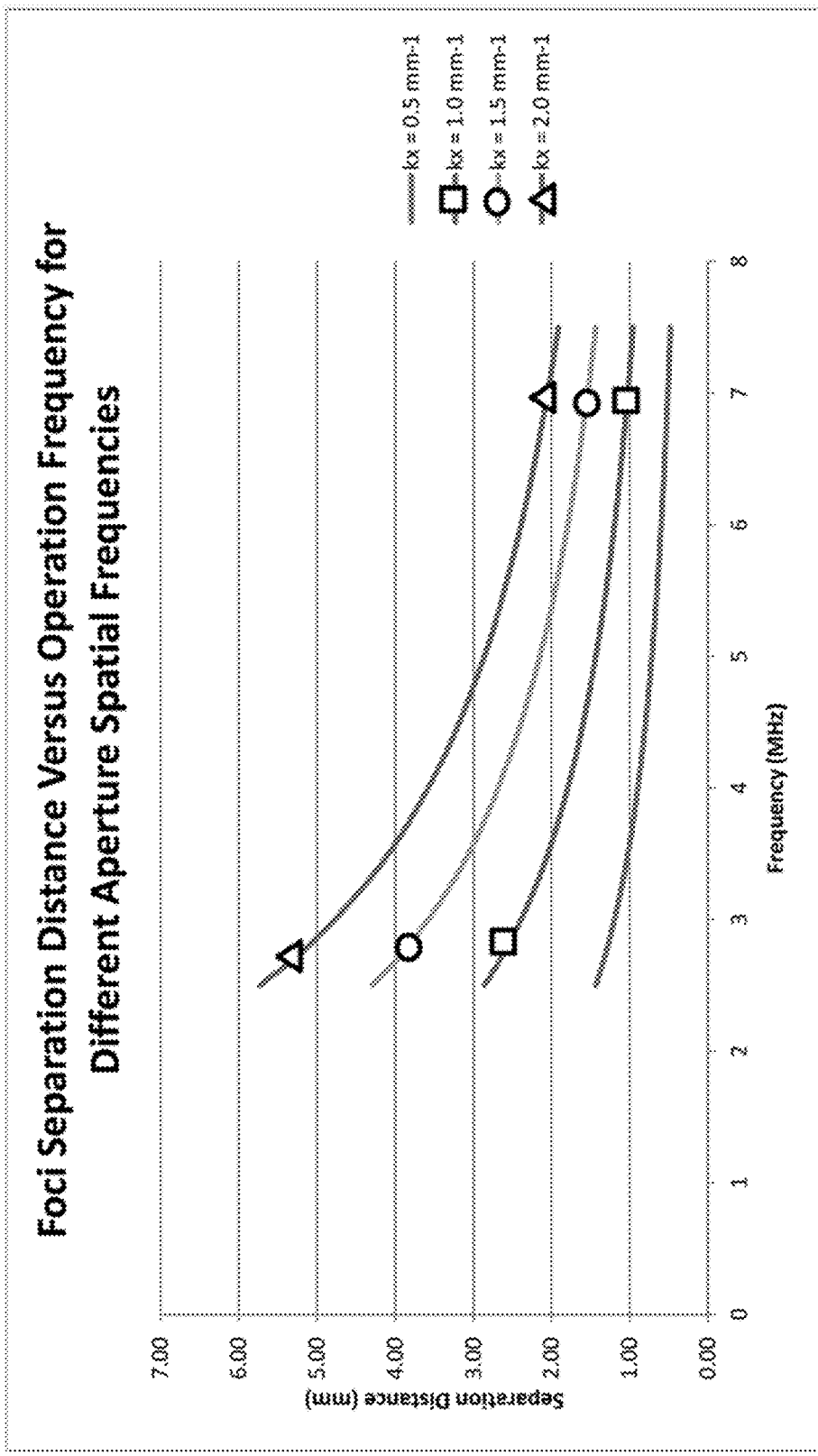
FIG. 6 is plot illustrating foci separation for apertures with different aperture spatial frequencies according to various embodiments of the present invention.

FIG. 6 shows the spacing difference for all operational frequencies of the aperture for different aperture spatial frequencies. As FIG. 6 shows, the separation distance increases as the frequency decreases.

Figure 7:
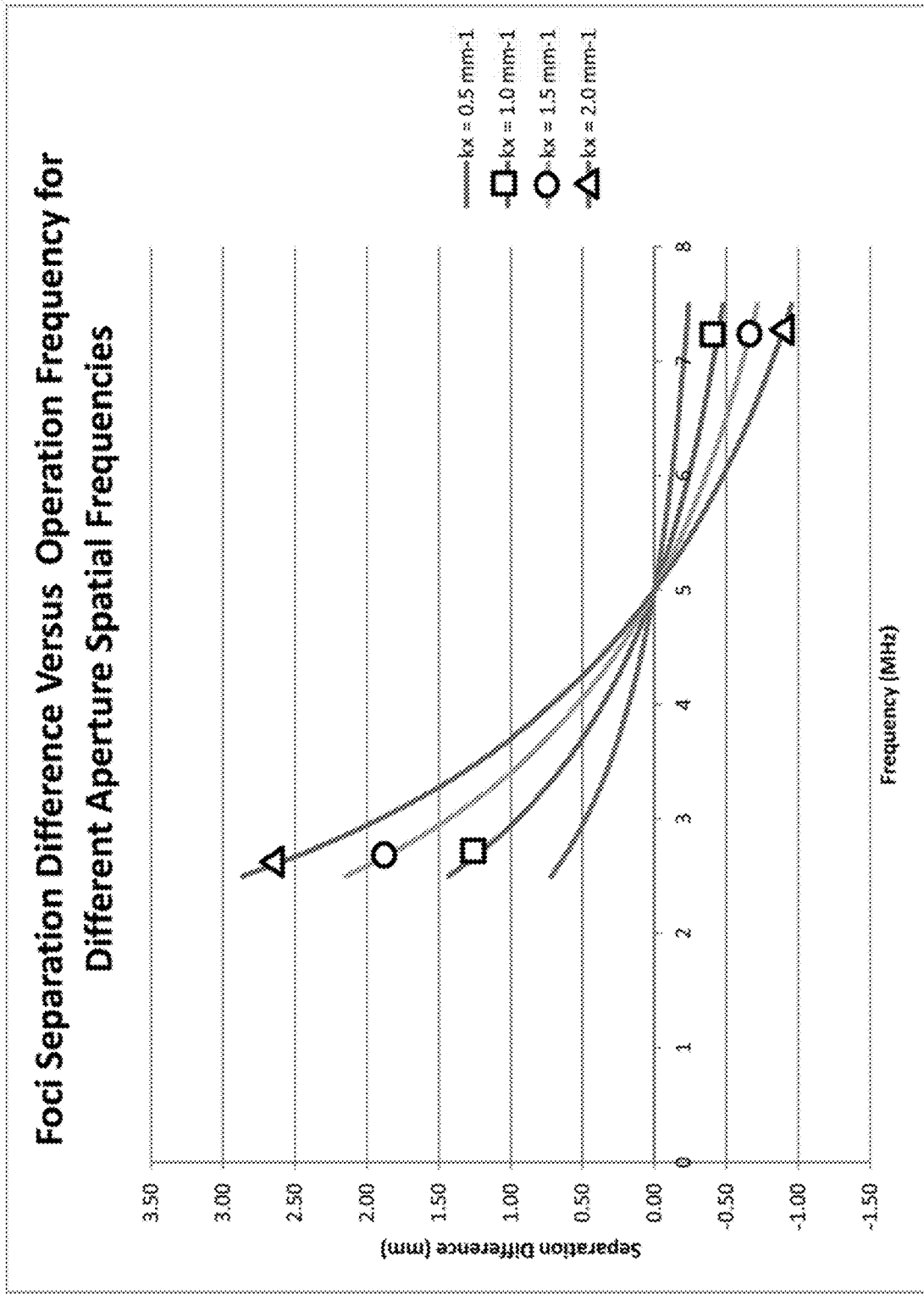
FIG. 7 is plot illustrating foci separation for apertures with different aperture spatial frequencies according to various embodiments of the present invention.

In one embodiment, the separation distance is relative to a frequency 5 MHz. In one embodiment, one way to estimate the electronic dithering from frequency modulation can be determined by referencing all movement to the initial separation at 5 MHz. As FIG. 7 shows, the spread of the separation distance between the foci can easily vary by over 1 mm.

In various embodiments, the range of possible operational frequencies from one aperture can be described in terms of the transducer bandwidth. In one embodiment, a larger transducer bandwidth results in an aperture that has a wider range of operational frequencies. Transducer bandwidth can be described as a percent fraction of the aperture center frequency by locating the frequency where the transmit intensity decreases to −3 dB of the peak transmit intensity. In one embodiment the −3 dB high frequency is designated as $f_{-3\ dB,H}$ and the −3 dB low frequency is designated as $f_{-3\ dB,L}$ for the transmit response of a transducer aperture. The −3 dB center frequency in [MHz] is described as:

$$f_{-3\ dB,center}=(f_{-3\ dB,H}+f_{-3\ dB,L})/2 \quad (17)$$

The −3 dB percent bandwidth is described as:

$$BW_{-3\ dB}=100\%*(f_{-3\ dB,H}-f_{-3\ dB,L})/((f_{-3\ dB,H}+f_{-3\ dB,L})/2) \quad (18)$$

In some embodiments, increasing the range of operational frequencies possible within one aperture may be achieved (but not limited to) by the use of backing layers, matching layers, multiple piezoelectric layers, electrical matching, piezoelectric composites, and/or a single crystal piezoceramic. In one embodiment, as the transducer bandwidth increases, the range of possible separation distance increases. Table 5 (below) shows how based on percent bandwidth the foci spread can vary if the aperture center frequency is 5 MHz. The foci separation distance for 5 MHz is 0.72 mm, 1.43 mm, 2.15 mm and 2.86 mm respectively for spatial frequencies of 0.5 $mm^{-1}$, 1.00 $mm^{-1}$, 1.50 $mm^{-1}$, 2.00 $mm^{-1}$. If the spatial frequency at the aperture is 1.50 $mm^{-1}$ and the transducer bandwidth is 60%, then the separation distance between the foci varies by 1.42 mm which is a distance greater than the lateral resolution of the beam at 5 MHz.

TABLE 5

| | Additional Spread from 5 MHz Center Frequency in [mm] | | | |
|---|---|---|---|---|
| Bandwidth | $k_x$ = 0.5 $mm^{-1}$ | $k_x$ = 1.0 $mm^{-1}$ | $k_x$ = 1.5 $mm^{-1}$ | $k_x$ = 2.0 $mm^{-1}$ |
| 20% | 0.14 | 0.29 | 0.43 | 0.58 |
| 40% | 0.30 | 0.60 | 0.90 | 1.19 |
| 60% | 0.47 | 0.94 | 1.42 | 1.89 |
| 80% | 0.68 | 1.36 | 2.05 | 2.73 |
| 100% | 0.95 | 1.91 | 2.86 | 3.82 |

In one embodiment, as the frequency is changed, the depth-of-field will also change as well as lateral resolution and focal gain. In one embodiment, as the frequency is changed, the depth-of-field, lateral resolution and focal gain will also change. Therefore, in one embodiment, the intensity at the aperture may change depending in the heating rate goals. Also, in some embodiments, it may be advantageous to send multiple operational frequencies at the same time to spread the energy immediately or near-immediately. For example, transmit excitation of the aperture may include excitation at 4 MHz, 5 MHz and 6 MHz all at the same time.

Multiple Foci by Changing the Aperture Spatial Frequency

As Equation 11c shows, the higher the aperture spatial frequency, the greater the separation distance between the foci. In one embodiment, an aperture is poled with a spatial frequency of $k_x$. The spatial frequency can be easily doubled or decreased to zero by connecting individual electrical excitation channels that have the ability to modify the phase to 0 degrees or 180 degrees, as shown in the embodiments in FIG. 8. For example, if the phase on channels 1 through 16 is 0 degrees, then the aperture spatial frequency is $k_x$. In an embodiment, as the phase on each channel is varied from 0 degrees to 180 degrees such that odd channels are at 0 degrees and even channels are at 180 degrees, then the spatial frequency at the aperture is ½ $k_x$. In an embodiment, if the phase repeats every two channels such that channel 1 and channel 2 is 0 degrees and channel 3 and channel 4 is 180 degrees and so on, then the spatial frequency at the aperture is 0. If channel 1 is 0 degrees, channel 2 is 180 degrees, channel 3 is 180 degrees, channel 4 is 0 degrees and so on, then the spatial frequency at the aperture is $2k_x$. In this case, seven unique foci can be created. As noted in Table 4 (at FIG. 5), if the aperture center frequency is 5 MHz, and the aperture frequency is any of 0 $mm^{-1}$, 0.5 $mm^{-1}$, 1.0 mm$^{-1}$, or 2.0 mm$^{-1}$, the corresponding separation distances are 0 mm, 0.72 mm, 1.43 mm and 2.86 mm, which yield seven unique focal positions separated by 0.36 mm. In various embodiments, intermediate phases between 0 degrees and 180 degrees would further allow the two foci to be tilted such that a line of foci could be created at the focal plane. Ultimately, the tilting, modulation of focal position, and frequency modulation enables the heating and possible coagulation of an entire line with a length of approximately 2.86 mm.

Figure 9:
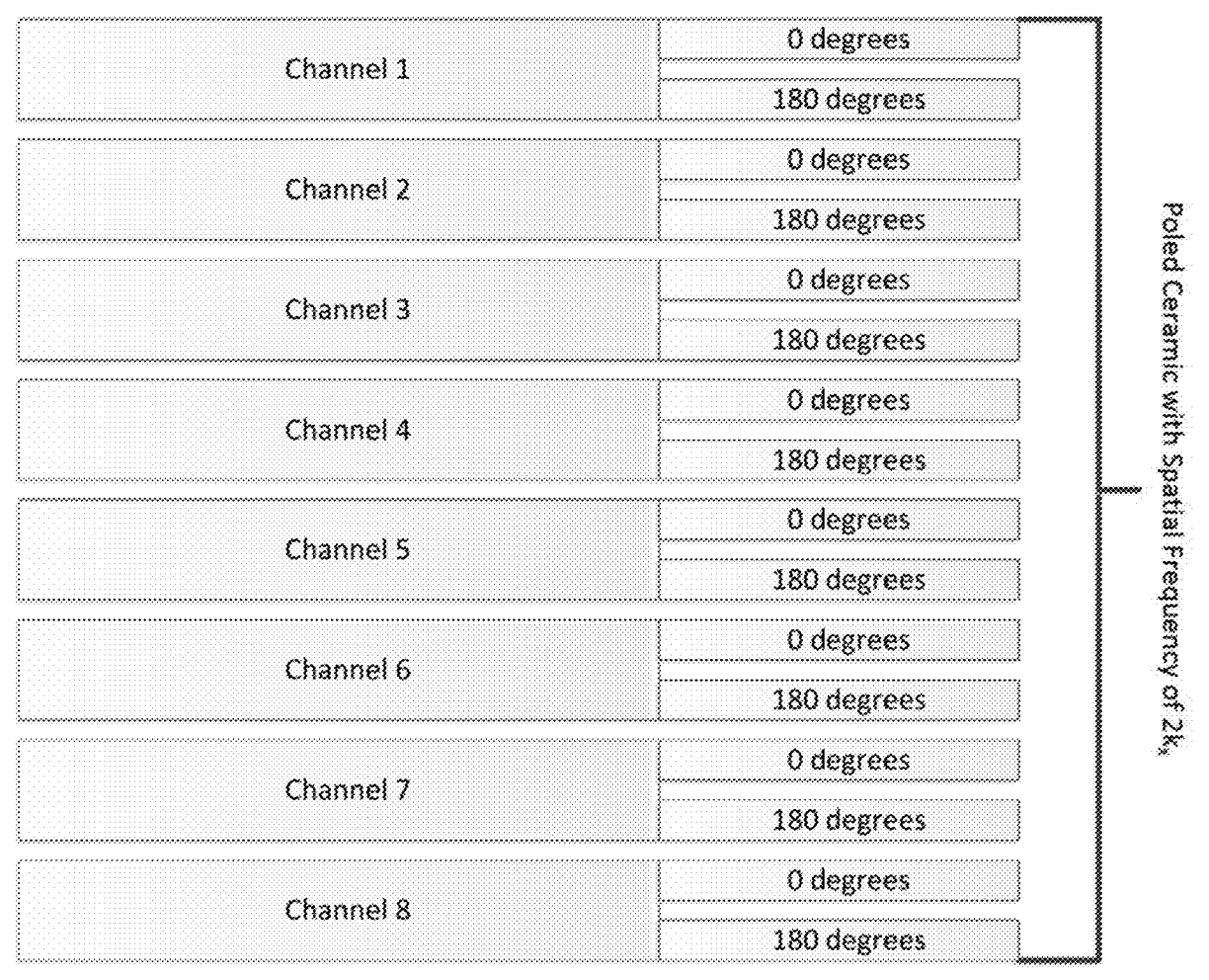

In one embodiment, a poled ceramic has a spatial frequency of 2$k_x$, as shown in FIG. 9. In this case, each electrical channel covers two poled areas in the ceramic (e.g., a piezoceramic). If channel 1 through channel 8 have the same electrical phase, then the spatial frequency of the aperture is 2$k_x$. If the phase alternates such that odd channels have a phase of 0 degrees and even channels have a phase of 180 degrees, then the spatial frequency of the aperture is $k_x$. In one embodiment, this configuration of only two phases are possible on the channels enables four unique foci. In various embodiments, if additional phases are allowable then it is possible to tilt the two foci to many different focal positions. This configuration limits the number of required electronic channels to get multiple foci positions.

Multiple Foci Using Multi-Channel Signal Mixing

In several embodiments, a treatment system utilizes multiple therapy channels to enable electronic focusing and/or steering. For example, a treatment system that utilizes multiple therapy channels to enable electronic focusing and/or steering allows for faster electronic dithering to either create more thermal coagulation using the same amount of energy as other treatment devices or equal thermal coagulation using electronic dithering with less energy than other treatment devices. This technique broadens the efficacy and comfort continuum that the device offers. In addition to electronic dithering, the multiple therapy channels also offer the possibility to move the beam to different depth locations such that two conventional transducers such as the DS7-4.5 (7 MHz at 4.5 mm depth) and DS7-3.0 (7 MHz at 3.0 mm depth) could be replaced by one single device that moves between the two different depths.

In one embodiment, a transducer 280 with multiple therapy channels 281 connected to move the beam axially (e.g. annular array) would typically create a TCP 550 at a deep depth first and then move to the shallower depth. In another embodiment, a TCP 550 is created at a shallow depth and then at a deeper depth below the skin surface. This creates the TCP 550 sequentially and would cause the treatment time to be extended. For example, in one embodiment, if the time for the deep TCP 550 is $t_{deep}$ and the time for the shallow TCP 550 is $t_{shallow}$, then the total treatment time for the two TCPs 550 is the sum of the two treatment times, $t_{deep}$ plus $t_{shallow}$. In one embodiment, total treatment time is reduced by forming multiple (two, or more) TCP's 550 simultaneously using signal mixing techniques which uses both signal apodization (shading) and phase control at each channel. In one embodiment, the total treatment time is the maximum of $t_{deep}$ and $t_{shallow}$:

Treatment time, conventional approach: $t_{treatment} = t_{deep} + t_{shallow}$

Treatment time, signal mixing: $t_{treatment} = \max(t_{deep}, t_{shallow})$

Figure 10:
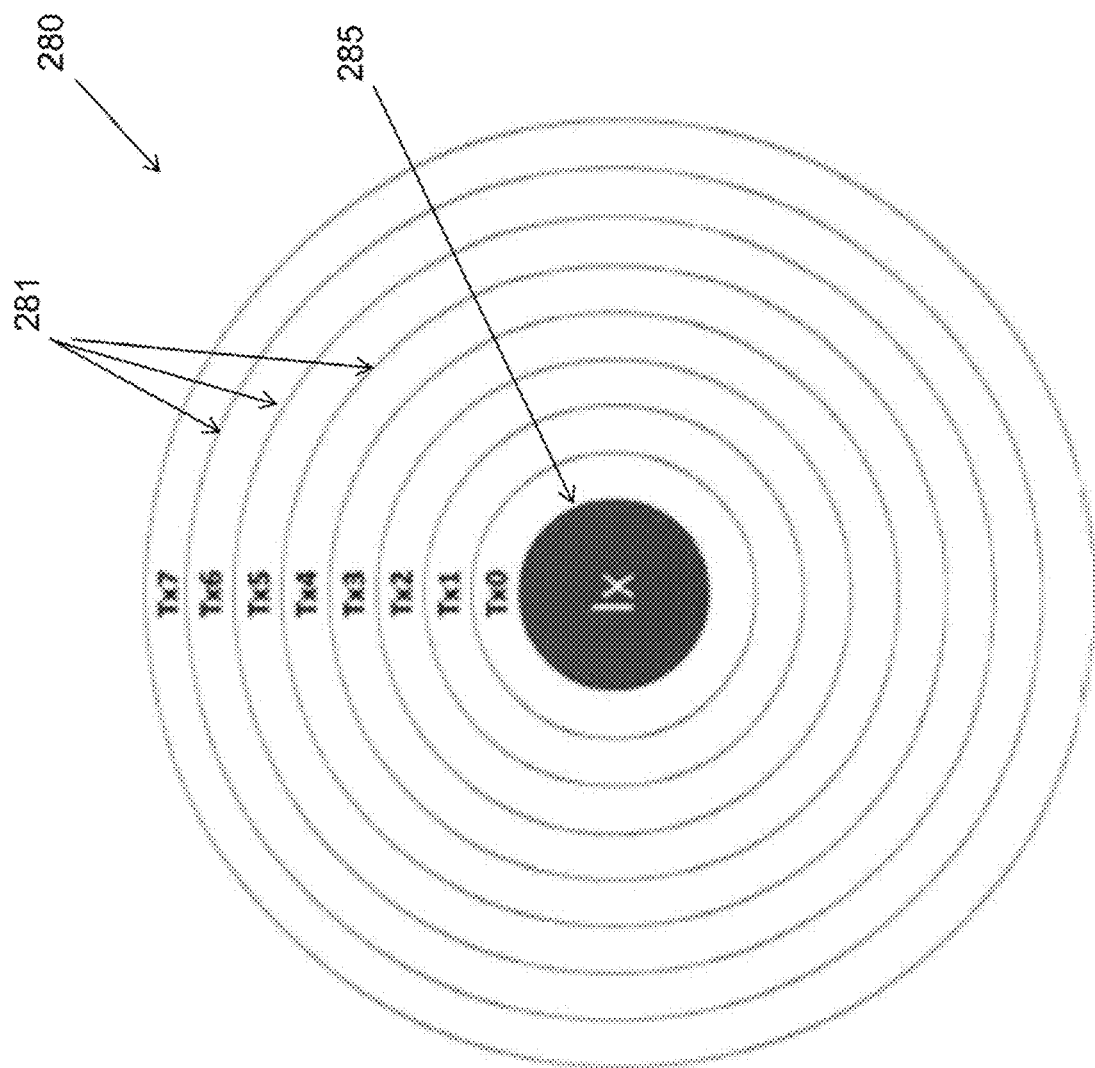
FIG. 10 is a schematic representation of an embodiment of array transducer with an imaging transducer.
Figure 11:
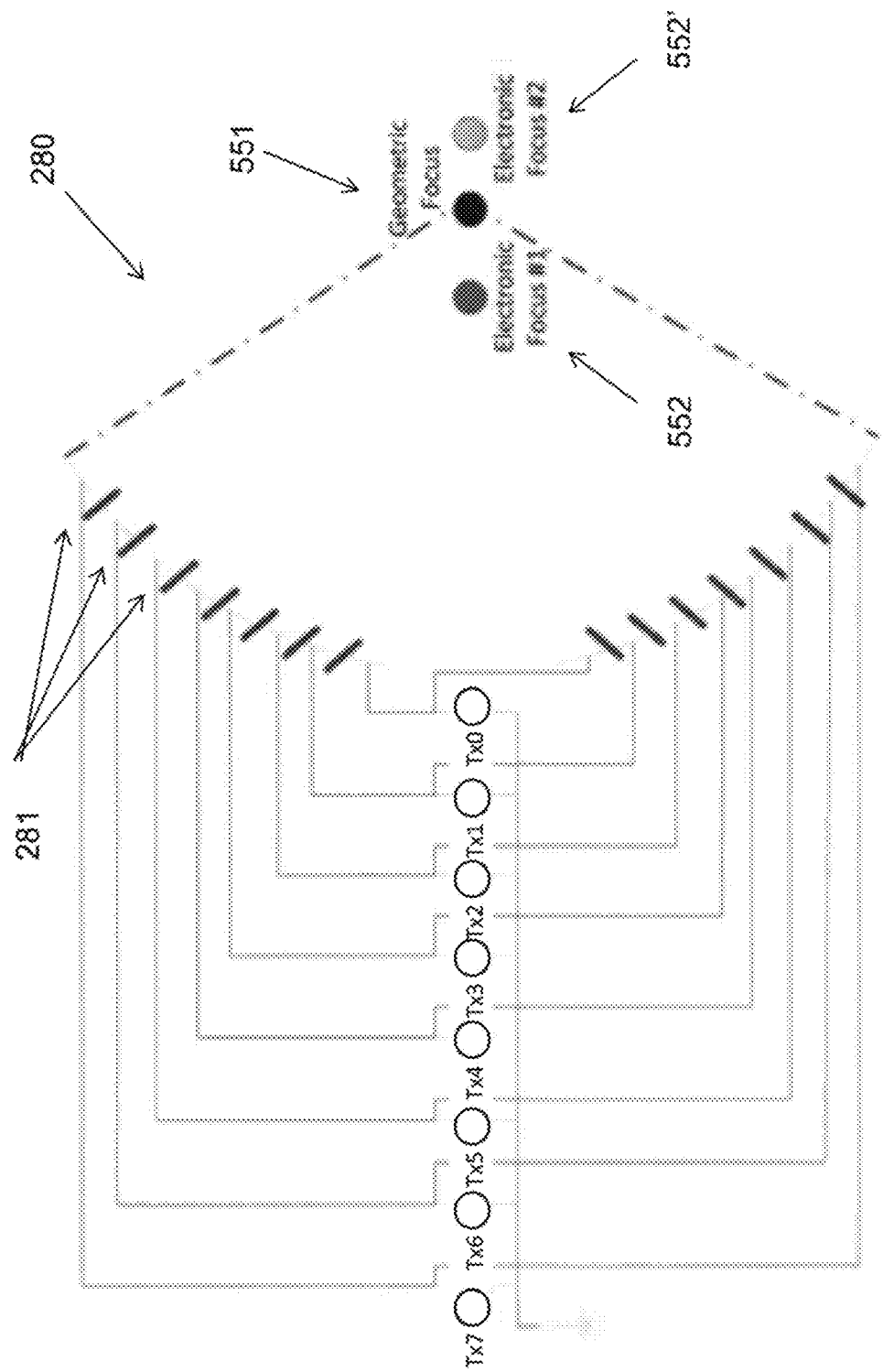
FIG. 11 is a schematic representation of an embodiment of the array transducer of FIG. 10 with a mechanical focus, a first electronic focus, and a second electric focus.

In an embodiment, an annular array design 280 enables the electronic movement of the therapy beam in depth (e.g., by changing depth of the TCP 550 below the skin surface). In one embodiment, a transducer 280 includes an eight therapy channel annular transducers elements 281 with a fixed mechanical focus. FIG. 10 shows a top view of one embodiment of this ceramic annular array design 280 with an imaging transducer 285 at the center of the bowl. In this embodiment, the therapy annular transducer 280 has eight rings identified as Tx0 though Tx7, corresponding to the elements 281. FIG. 11 shows a side view of the same eight channel annular transducer 280 with hash marks signifying the boundaries between rings. In this embodiment, eight separate excitation sources have been connected to the individual annular rings 281. In addition to the electrical excitations, the geometric focus 551 and two electronic foci 552, 552' have been identified.

In one embodiment, there is a unique amplitude 'A' and phase '8' applied to each therapy channel and corresponding annular ring 281 for each focus at a given therapy frequency 'w'. The excitation function for a channel can be generalized to the following form:

$$f_{n,m}(t) = A_{n,m} \sin(\omega t + \theta_{n,m}) \tag{19}$$

where n is the ring or channel number and m is the focus number.

In the case of creating a TCP at the geometric focus, the phase is zero and equation (19) can be rewritten as:

$$f_{n,1}(t) = A_{n,1} \sin(\omega t) \tag{20}$$

where the '1' in the subscript signifies the geometric focus.

In the case of creating a TCP 550 at electronic focus #2, the phase of the rings must be adjusted to focus the ultrasound at the spatial point using bowl geometry and time delay estimates. The excitation function can be written as:

$$f_{n,2}(t) = A_{n,2} \sin(\omega t + \theta_{n,2}) \tag{21}$$

where the '2' in the subscript signifies the electronic focus #2 and the angle is the required phasing for the ring.

Now, in the conventional case, the two TCP's would be created sequentially with typically the deeper TCP generated first and then the shallow TCP. However, signal mixing allows the two excitation signals to be represented as one signal such that both TCPs could be generated simultaneously.

$$f_{n,total}(t) = f_{n,1}(t) + f_{n,2}(t) = A_{n,1} \sin(\omega t) + A_{n,2} \sin(\omega t + \theta_{n,2})$$

$$f_{n,total}(t) = c \sin(\omega t + \phi) \tag{22a}$$

where $c = \mathrm{sqrt}(A_{n,1}^2 + A_{n,2}^2 + 2A_{n,1}A_{n,2} \cos(\theta_{n,2}))$ and $$\phi = a\tan 2(A_{n,2} \sin(\theta_{n,2}), A_{n,1} + A_{n,2} \cos(\theta_{n,2})) \tag{22b}$$

The amplitude and phase at each ring is modified to support the focusing at two locations simultaneously.

In some embodiments, the time to deliver the dose for one focus will be slightly different than the second focus. In one embodiment, the excitation may start or end on the focus with the longer dosing time with excitation modified to support the dosing at two foci simultaneously using Equation (22b) during the other times. For example, in one embodiment, for $f_{n,1}$ a total dosing time of 30 msec is required whereas for $f_{n,2}$ a total dosing time of 60 msec is required. In order to satisfy this, many different excitations scenarios could be used:

$$f_{n,2}(t) \text{ for 30 msec and then } f_{n,total}(t) \text{ for 30 msec} \tag{23a}$$

$$f_{n,total}(t) \text{ for 30 msec and then } f_{n,2}(t) \text{ for 30 msec} \tag{23b}$$

$$f_{n,2}(t) \text{ for 15 msec and then } f_{n,total}(t) \text{ for 30 msec and } f_{n,2}(t) \text{ for 15 msec} \tag{23c}$$

In one embodiment, this concept can be further generalized to more than two simultaneous foci. Suppose the excitation on one ring is the following:

$$f_{n,total}(t) = \sum_{i=1}^{m} A_{n,i}\sin(\omega t + \theta_{n,i}) = A_{n,total}\sin(\omega t + \varphi_n) \quad (224)$$

$$A_{n,total}^2 = \sum_{i=1}^{m}\sum_{j=1}^{m} A_{n,i}A_{n,j}\cos(\theta_{n,i} - \theta_{n,j})$$

$$\tan(\varphi_n) = \frac{\sum_{i=1}^{m} A_{n,i}\sin(\theta_{n,i})}{\sum_{i=1}^{m} A_{n,i}\cos(\theta_{n,i})}$$

where n is the ring number and m is the number of simultaneous foci. This generalization to more than two foci enables the geometric focus, shallow electronic focus and deep electronic focus to be delivered at the same time.

Figure 12:
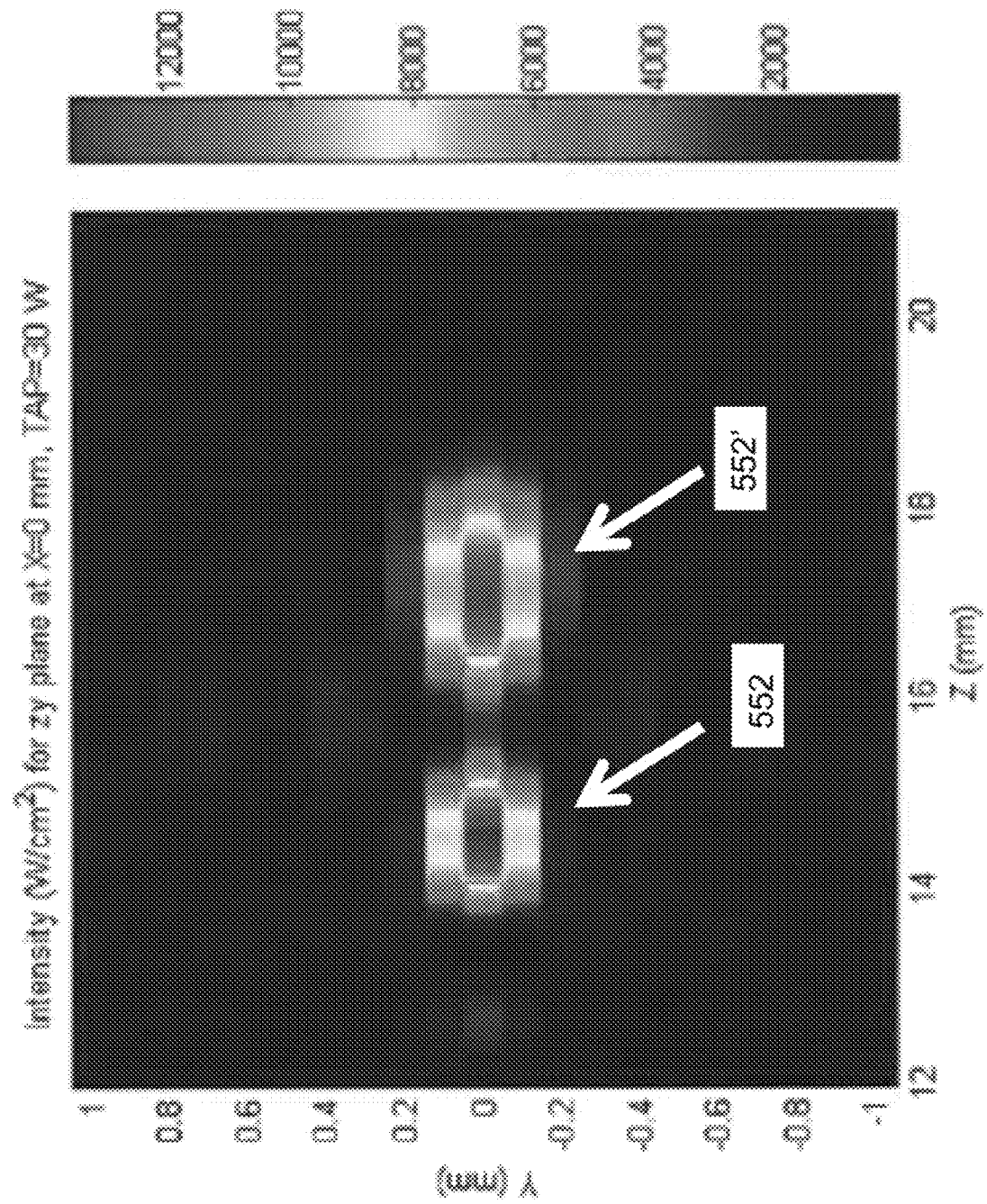
FIG. 12 is a schematic representation of an embodiment of an intensity map of a treatment with two foci at 15 mm and 17 mm.
Figure 13:
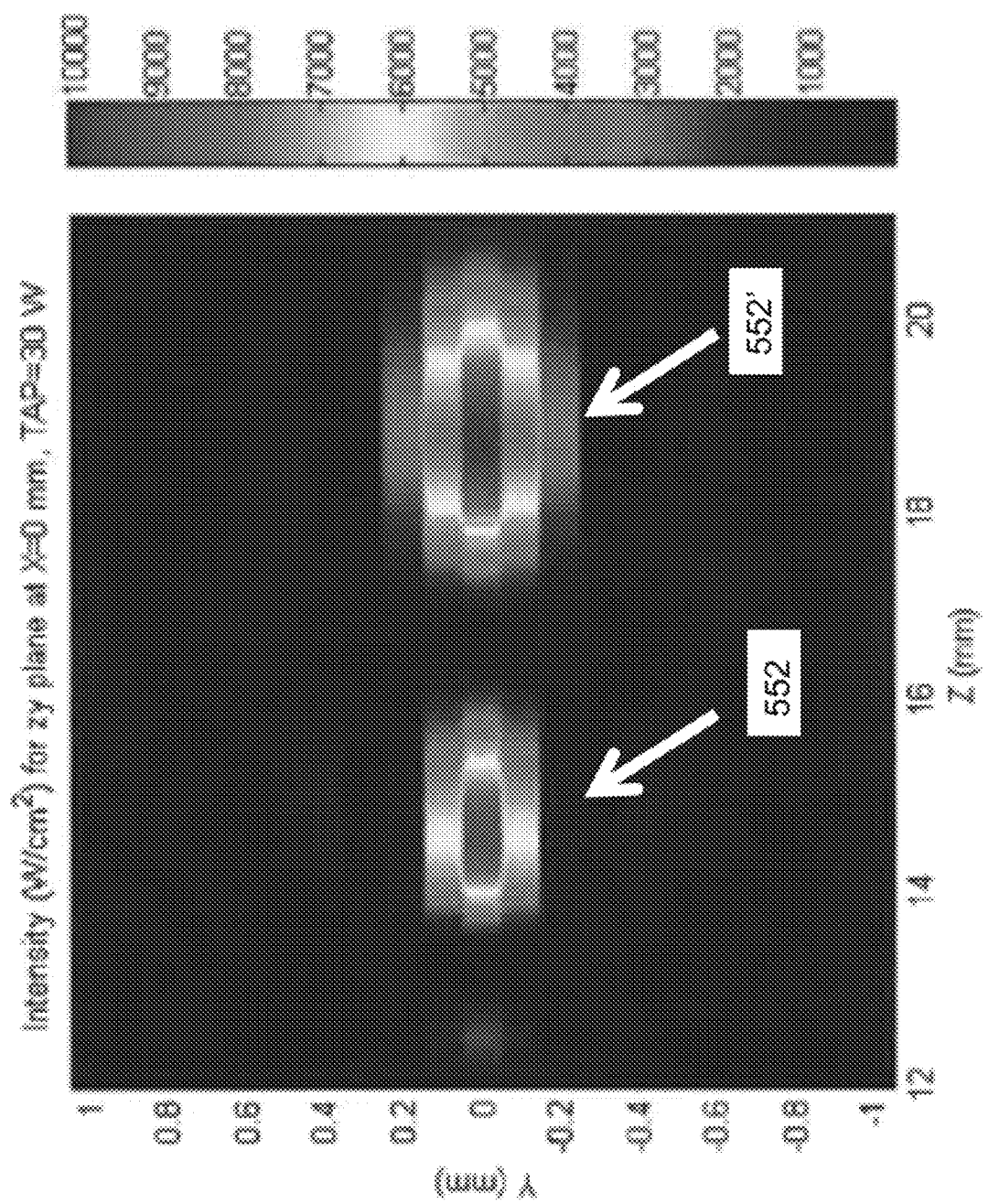
FIG. 13 is a schematic representation of an embodiment of an embodiment of an intensity map of a treatment with two foci at 15 mm and 19 mm.

In one embodiment, an experiment was conducted using simulations of two simultaneous foci were completed to show that when this theory is applied that two foci appear. The simulations attempted to place a therapy focus at 15 mm and 17 mm simultaneously. FIG. 12 shows the intensity map in azimuth and depth for this simultaneous excitation. The intensity map clearly shows two foci appearing at 15 mm and 17 mm. Another simulation was done with the foci at 15 mm and 19 mm respectively. FIG. 13 shows the results. In various embodiments, this technique can be applied to any array. The array can be annular, linear, or any electronically controlled array transducer.

Ultrasound Imaging for Improving Ultrasound Therapy Treatments

In an embodiment, the imaging resolution is improved via electronic focusing on the beam axis in transmit and receive signals. In various embodiments, imaging resolution is improved by 10%, 20%, 40%, or 50%, 10%-50%, or any values therein. In an embodiment, increasing imaging resolution may not interrogate as well the coupling between the therapy transducer and the skin since the cross-section of the therapy beam is much wider than the imaging beam at this tissue interface.

Figure 14:
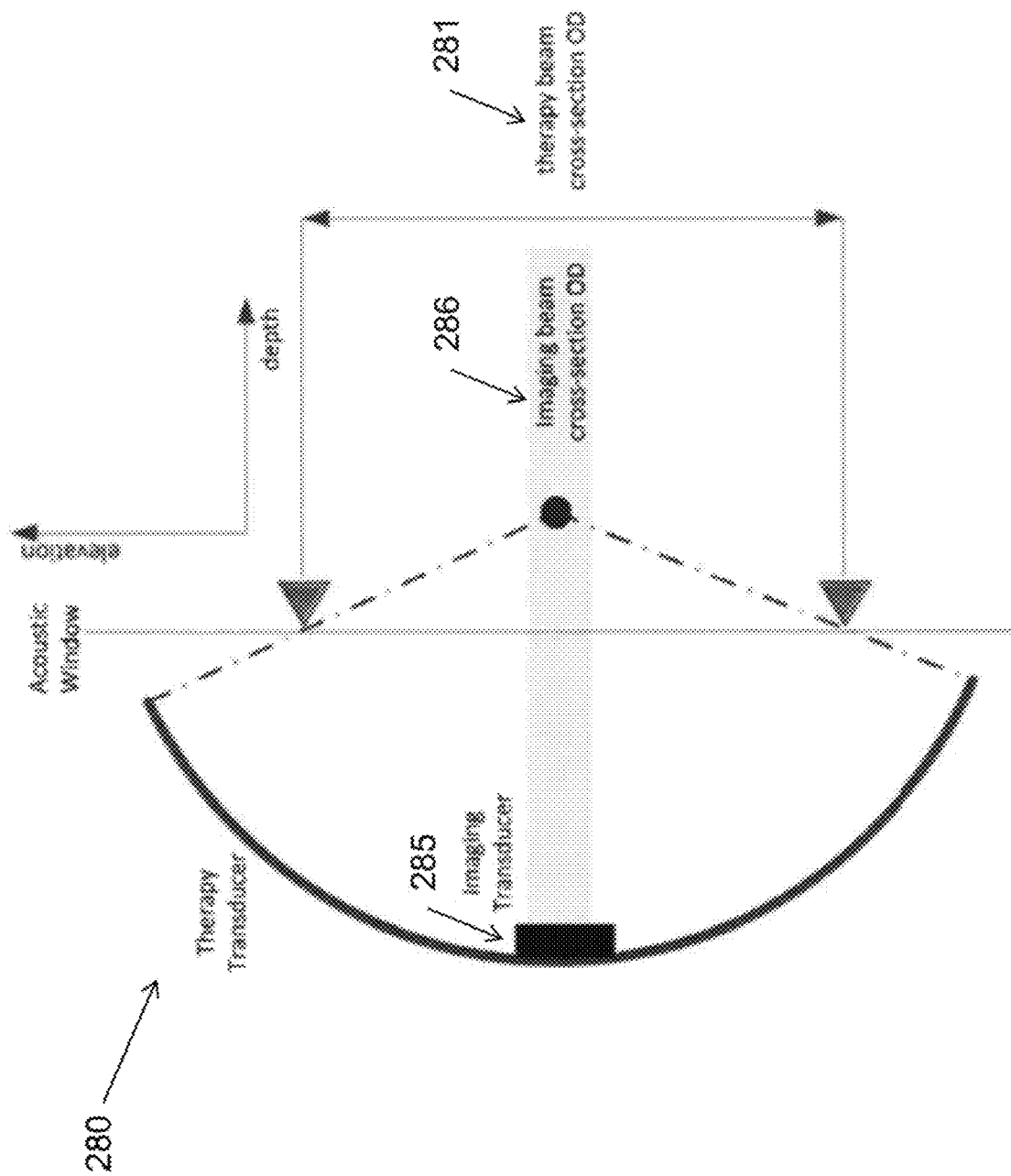
FIG. 14 is a schematic representation of the cross-section of the difference between the size of an ultrasound therapy beam compared to an ultrasound imaging beam according to various embodiments of the present invention.

FIG. 14 illustrates an embodiment of a cross-section of a therapy beam 281 from a therapy transducer 280 through an acoustic window interface compared to the cross-section of the imaging beam 286 from an imaging transducer 285. In this figure, the movement of the transducer 280 is in-and-out of the page. As FIG. 14 shows, the OD of the therapy cross-section is significantly greater than the imaging cross-section. Analysis using trigonometry and simple ray tracing shows that for a therapy transducer with a 4 MHz therapy beam directed to a depth of 4.5 mm below the skin surface (DS 4-4.5) has a therapy beam OD 281 of 8 mm whereas the imaging beam OD 286 is expected to be approximately 0.25 mm. In this case, if the small imaging beam is used to check for proper coupling, only approximately 0.1% of the therapy beam through the acoustic window is interrogated. In an embodiment, this estimate may be slightly underestimated due to diffraction effects of the therapy beam.

In an embodiment, an imaging beam 286 is extended to a larger (e.g., 10%, 15%. 25%, 50%, 75%, 90%, 100%) entire image frame to cover more, or all, of the therapy beam 281 cross section. In an embodiment, an image has a width of 25 mm. If the areas are calculated and compared (e.g. slice thickness and width), then the imaging plane only interrogates approximately 2.5% of the total therapy area cross-section at the acoustic window. Although this is improved over the initial calculation, it is still significantly below 100% coverage. In various embodiments, imaging provides for properly interrogate more (e.g., 10%, 15%. 25%, 50%, 75%, 90%, 100%) the coupling using an imaging system with an annular array. In some embodiments, image processing enables proper interpretation by the operator.

Linear Imaging Array

Figure 15:
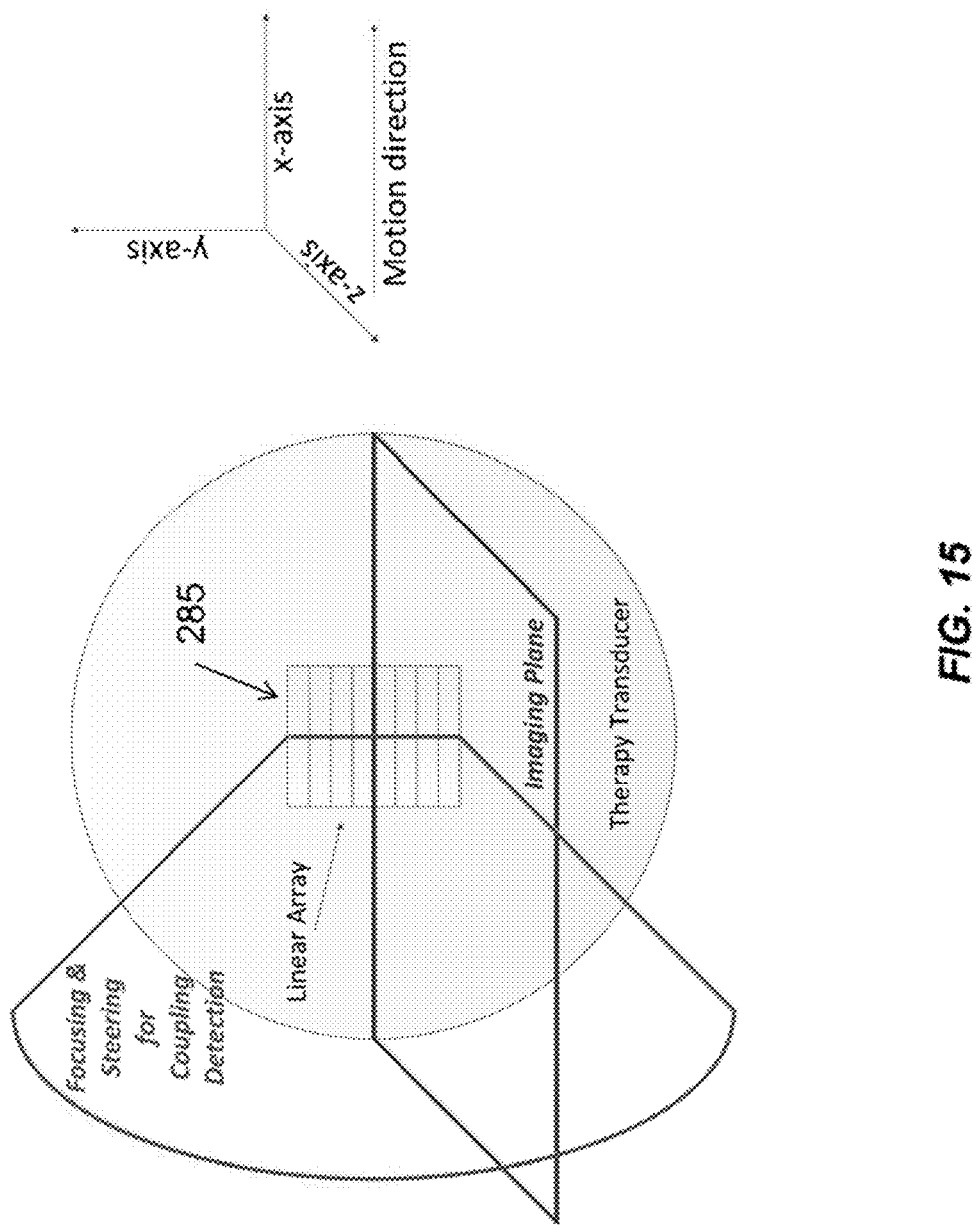
FIG. 15 is a schematic representation of a linear array according to various embodiments of the present invention.

In various embodiments, an ultrasound treatment system comprises an imaging module and an imaging array 285. In various embodiments, the imaging array 285 is a linear array, such as shown in the embodiment at FIG. 15. In one embodiment, a method for detecting the amount of acoustic coupling between tissue and the ultrasound treatment systems is to use a linear array which is oriented in the transducer module such that electronic steering and focusing of the beam is along the y and z dimensions. This is orthogonal to the direction of motion with a motion mechanism. In this embodiment, the linear array focuses the imaging beam in the imaging plane multiple times as the transducer is moved along the x-axis which generates a high resolution ultrasound image. As the linear array translates along the x-axis, an imaging beam can also be steered and focused away from the imaging plane to better assess the coupling of the therapy beam cross-section into tissue. In some cases, this may give an even better spatial determination of poor coupling regions than the annular array due to the spatial specificity of the imaging beam. This is especially true if the linear array is a 1.25D, 1.5D, 1.75D, or 2D array.

Annular Imaging Array

Figure 16:
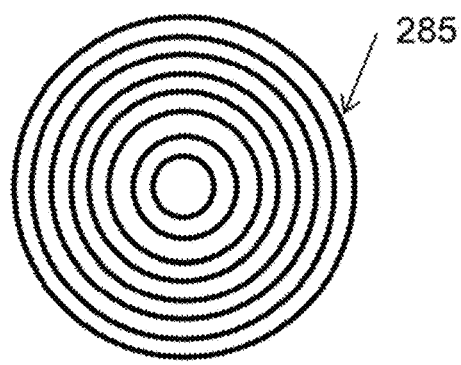
FIG. 16 is a schematic representation of an annular array according to various embodiments of the present invention.

In various embodiments, an ultrasound treatment system comprises an imaging module and an imaging array 285. In various embodiment, the imaging module has multiple (e.g., 2, 4, 8) transmit channels and multiple (e.g., 2, 4, 8) receive channels that operate from between 8 MHz to 50 MHz (e.g., 8, 9, 10, 12, 15, 20, 22, 25, 28, 30, 40 or 50 MHz and any ranges therein) for purposes of imaging the skin to approximately 25 mm in depth. In one embodiment, the imaging module has eight transmit channels and eight receive channels that operate from 8 MHz to 50 MHz for purposes of imaging the skin to approximately 25 mm in depth. The eight channels enable unique imaging aperture designs with elements that offer electronic steering and focusing in transmit and receive. One of these types of apertures is an annular array (FIG. 16).

In some embodiments, the annular array 285 contains rings of equal element areas that permit electronic focusing along the beam axis. In one embodiment, a mechanically scanned annular array 285 offers superior imaging performance over a more technically advanced, electronically controlled linear array 285'. This is because an annular array 285 focuses the beam along the beam axis in azimuth and elevation. The radial symmetry produces a high resolution beam with equivalent beamwidth. The linear array 285' uses electronic focusing in azimuth and mechanical focusing in elevation which is equivalent to a compound lens. The resolution of the beam in azimuth can match the performance of the annular array 285; however, the resolution of the beam in elevation underperforms the annular array 285 due to the mechanical lens having only one focal depth.

Figure 17:
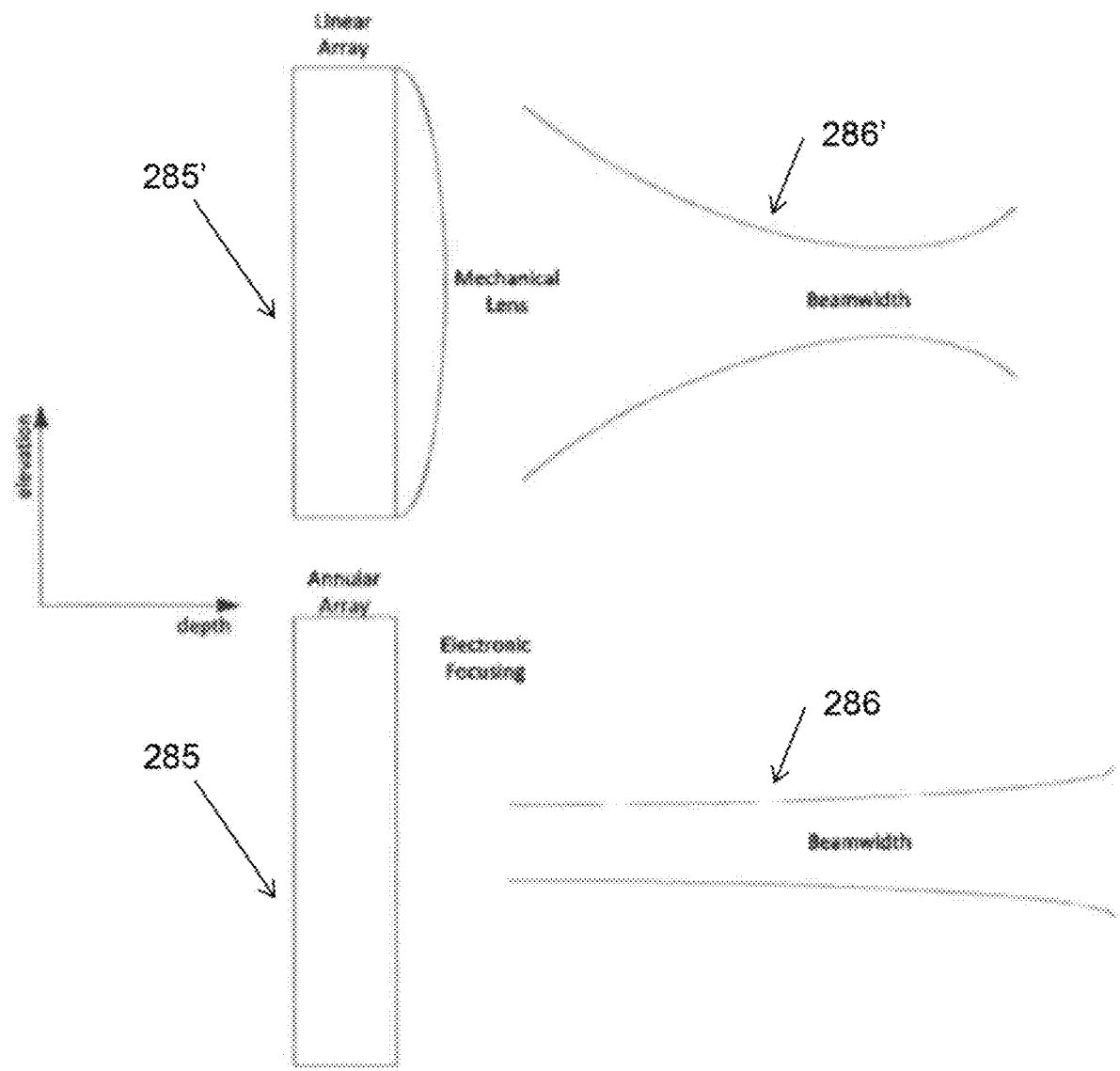
FIG. 17 is a schematic representation of an annular array compared to a linear array according to various embodiments of the present invention.

FIG. 17 shows an embodiment of the focusing capability of an annular array 285 when compared to a linear array 285' in elevation. The beamwidth 286 remains narrow throughout the depth for the annular array 285. However, this narrow beamwidth 286 limits an acceptable level of interrogation of the therapy beam both pre-focally (e.g. at tissue coupling) and post-focally (e.g., at bone).

Figure 18:
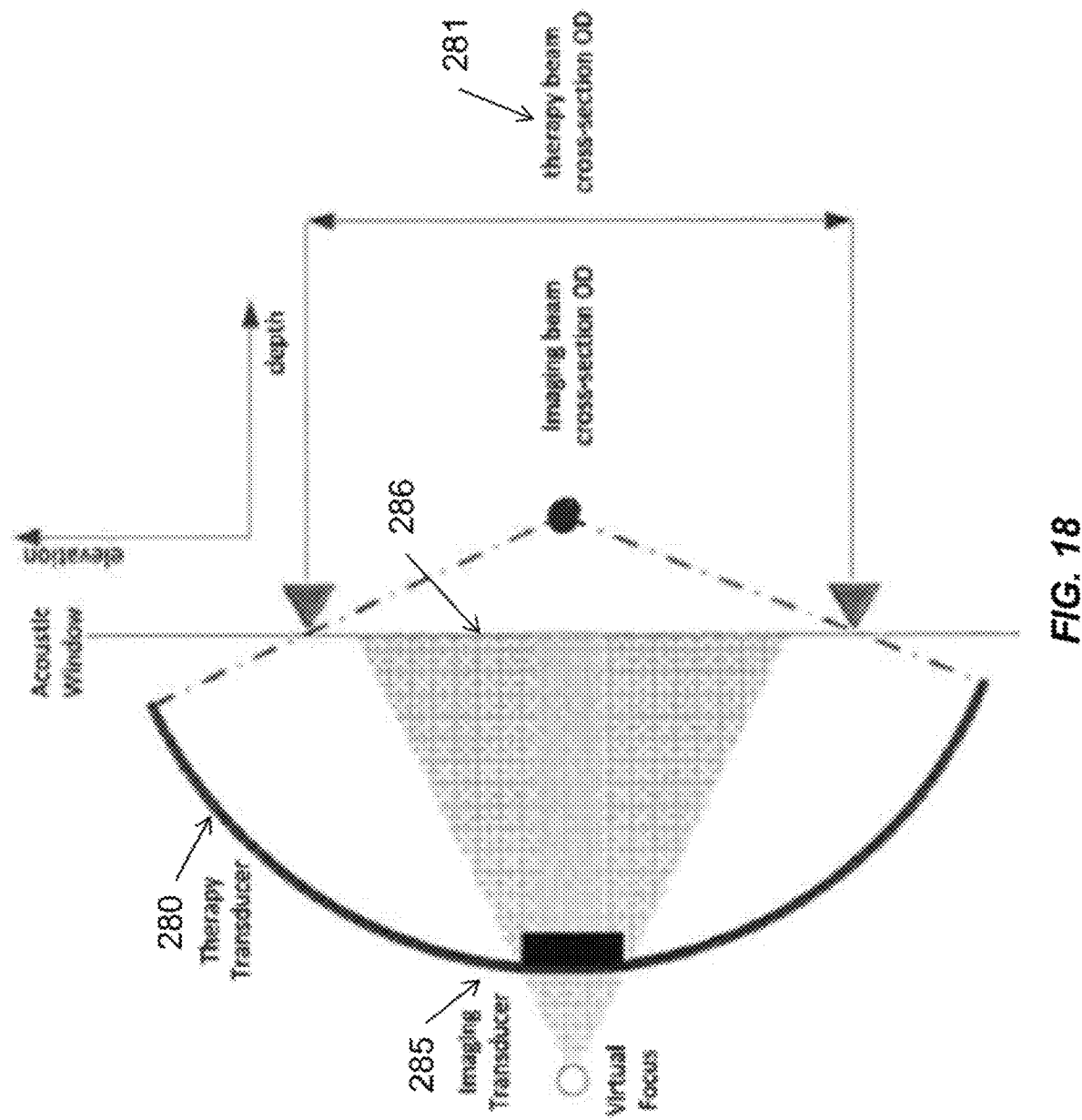
FIG. 18 is a schematic representation of an annular array with a virtual focus behind the array according to various embodiments of the present invention.
Figure 19:
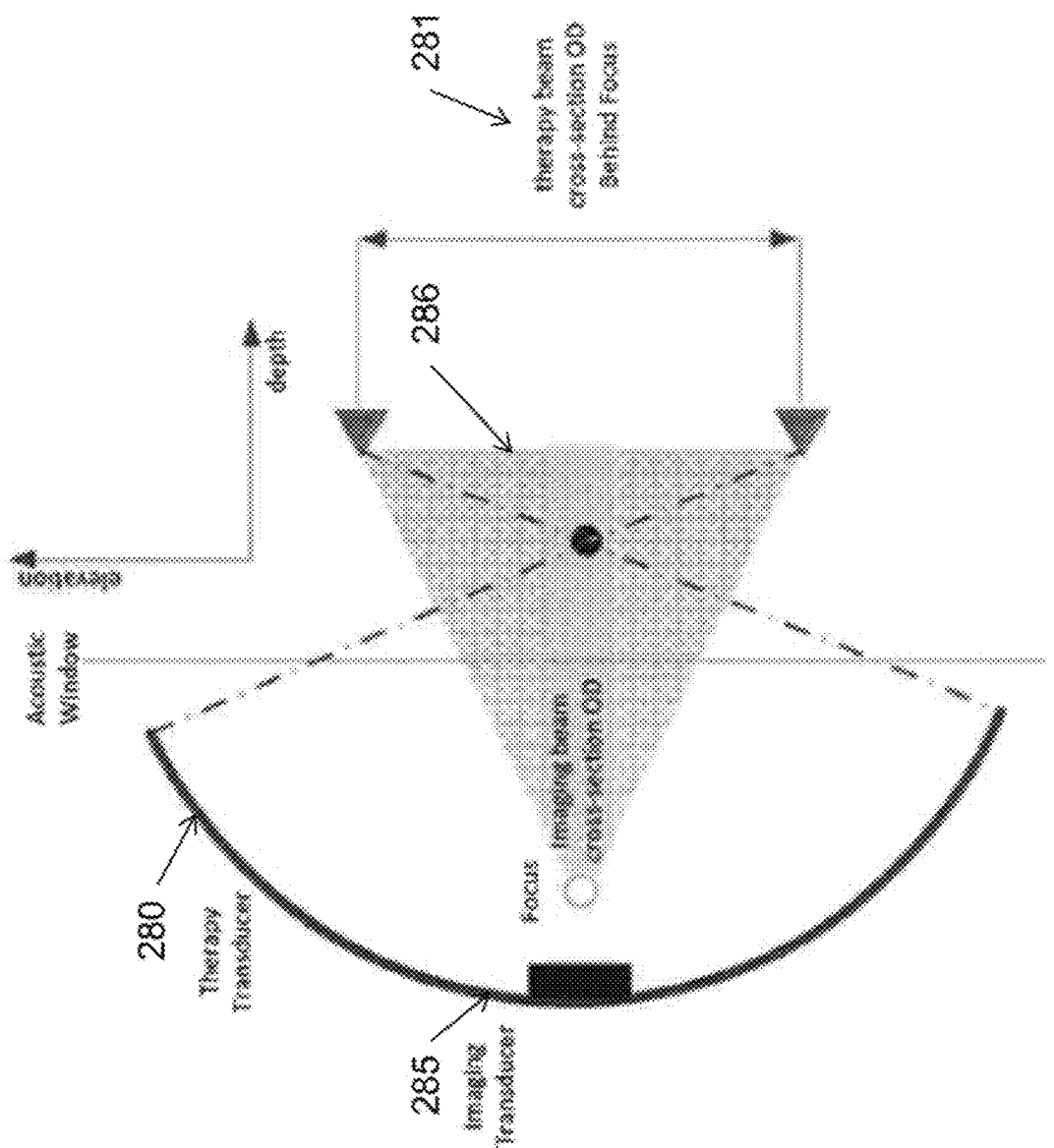
FIG. 19 is a schematic representation of an annular array with a virtual focus between the array and acoustic window according to various embodiments of the present invention.

In one embodiment, the annular array 285 is superior to standard imaging transducers because it can focus on the beam axis in transmit and receive. Just as the annular array 285 can focus in tissue, it can also effectively focus behind the transducer 285. This focus behind the imaging array 285 defocuses the acoustic energy propagating toward the tissue such that it is possible to better interrogate the coupling of the therapy behind at the acoustic window as well as the possibility of obstructions (e.g., bone) behind the therapy focus. FIG. 18 shows an embodiment of a virtual focus behind the annular imaging array 285 and the effective response toward the tissue. The defocused beam 286 spreads from the imaging array 285 toward the acoustic window such that a much larger percentage (e.g., 10%, 20%, 30%, 40%, 50%, 60%, 70%, 80%, 90%, 100%, and any ranges or values therein) of the coupling for the therapy beam is interrogated. Another transmit focus depending on the specific beamwidth and penetration characteristics may be used to defocus the beam behind the therapy focus. This may be accomplished by placing a virtual focus behind the annular array 285 or a focus immediately in front to meet the required point-spread-function beamwidth when compared to the therapy beam. FIG. 19 shows an embodiment of a therapy beam 286 that quickly spreads behind the focus and the width of the imaging beam 286 may need to be slightly larger to search for tissues or implants that do not readily couple ultrasound energy (e.g. bone, intestines). In some embodiments, the goal is to better probe the acoustic window prior to the therapy focus and tissue behind the therapy focus to insure safe and efficacious treatment.

Vector Imaging

In some embodiments, defocusing the beam at the acoustic window and behind the therapy focus is advantageous to test for coupling and potential tissue impediments (e.g., bone, intestines) or implants. The processing and display of this information can be used by the system operator to make appropriate decisions without interfering with normal imaging. In one embodiment, in order to provide the information in a timely manner, the transmit-receive events with the defocused beam are be interwoven with standard imaging. This form of imaging enables the frame rates for regular B-mode imaging and the coupling pulses.

Figure 20:
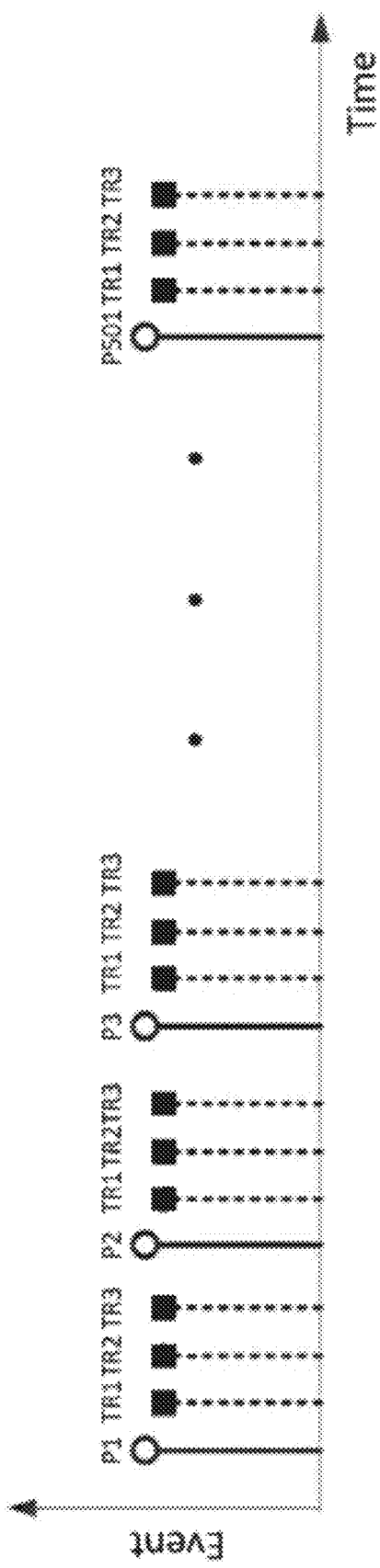
FIG. 20 is a schematic representation of time progression of the transmit-receive vectors for ordinary B-mode imaging according to various embodiments of the present invention.

FIG. 20 shows an embodiment the time progression of the transmit-receive vectors for ordinary B-mode imaging. In standard imaging, the transmit-receive events occur when the annular array 285 is at the appropriate azimuth location (e.g. P1). In one embodiment, an ultrasound imaging and treatment system will utilize 1 to 4 transmit foci per imaging vector to generate a high resolution frame. FIG. 20 represents the position vector with a 'P' and then a number. In one embodiment, P1 has three transmits: TR1, TR2, and TR3. DF1 is an interrogation pulse to check if the system properly coupled to the tissue to be treated. In one embodiment, for 25 mm, the scan will consist of 501 vectors separated by 0.050 mm for a total imaging width of 25 mm. The transmit-receive event is represented with a 'TR' and then a number. FIG. 20 shows that three transmit-receive events are associated with each position, or in other words, there are three transmit foci for each vector position. When applying the defocused beam, it is not necessary to transmit at every position. This is because the beam has a much larger beamwidth than the sample spacing of 0.050 mm. Further, in one embodiment, the imaging beam width at the acoustic window for the defocused transmit is approximately 5 mm, then possibly the window is sampled every 0.5 mm. This is because there is really no additional information acquired by finer sampling. This type of imaging involves an interleaved (e.g., overlapping, etc.) imaging approach as shown in FIG. 21.

Figure 21:
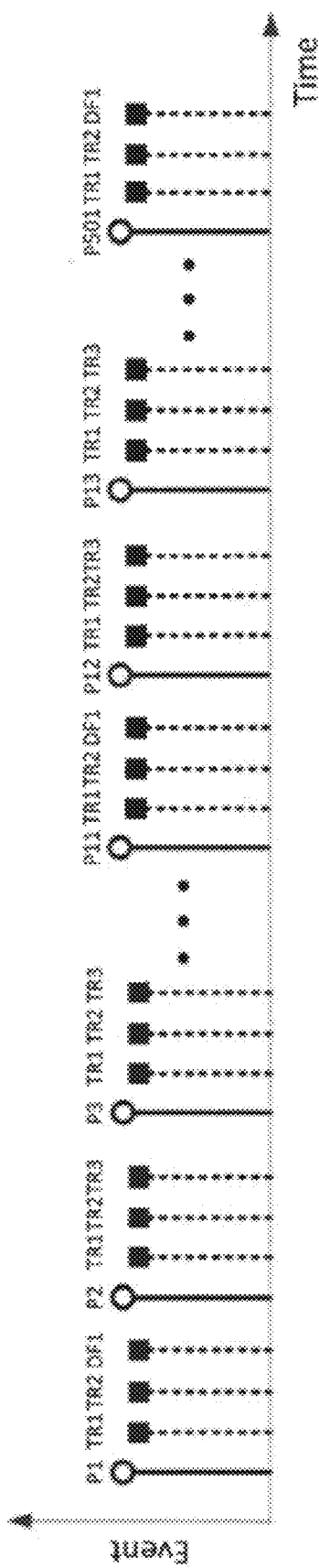
FIG. 21 is a schematic representation of an interleaved imaging approach according to various embodiments of the present invention.

The vector imaging is similar in FIG. 21 as in FIG. 20 except that at P1 and then every 10 positions after than a defocused vector is acquired. Therefore, there are still 501 vectors acquired for the high resolution image. However, in addition to these 501 vectors, 51 vectors are acquired using the defocused transmit to assess coupling at the acoustic window. The 501 vectors and corresponding transmit-receive events are processed differently than the 51 vectors used to assess coupling. Note that this is only one method of vector sequencing. Because the high resolution imaging is oversampled laterally by approximately four to five beamwidths, it is possible to drop one sequence at a position and just perform defocused imaging. Averaging may be applied where defocused imaging is applied to interpolate between vectors. This would permit a shallow (e.g. at the acoustic window) and deep assessment (e.g. behind the focus) of the coupling and tissue to assess the safety and efficacy of therapy energy delivery. The type of sequencing is analogous to duplex imaging which perform B-mode and Doppler imaging simultaneously.

Figure 22:
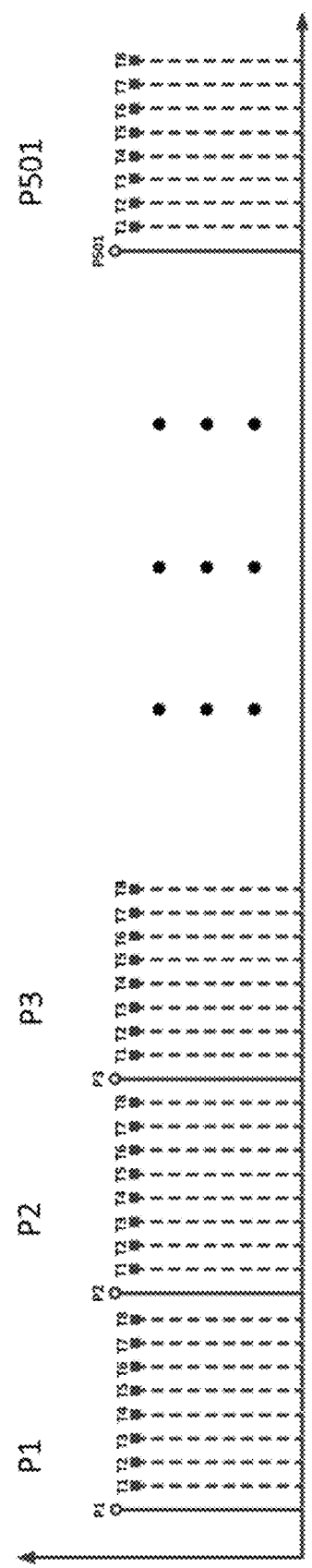
FIG. 22 is a schematic representation of an imaging approach with synthetic transmit and receive aperture methods according to various embodiments of the present invention.

In embodiments where there is sufficient transmit sensitivity and receive signal-to-noise ratio, synthetic transmit and receive aperture imaging may be utilized to achieve optimal resolution in the ultrasound image and permit ample means to determine if there is sufficient coupling for the therapy transducer. FIG. 21 shows an embodiment where defocused transmit-receive events are interwoven with three standard focused transmit-receive events. This method may cause a compromise with the ultrasound image resolution. In one embodiment, illustrated at FIG. 22, a method transmits on each imaging array element separately and receive on the individual receive elements. After the data is digitized and stored for each of the eight transmit receive sequences as shown in the timing diagram, synthetic transmit and receive aperture methods are used to generate the optimal resolution for the ultrasound image and develop ideal beam widths to assess the coupling of the therapy transducer. Synthetic transmit and receive aperture methods simultaneously apply transmit and receive delays on post processed data for every spatial point in the ultrasound image. This technique yields ideal resolution throughout the entire ultrasound image when there is sufficient receive SNR at the cost of a reduced frame rate. The same method can be applied when interrogating the therapy beam cross-section.

Image Processing

In one embodiment, an advantage of using the defocused beam are to help the operator assess coupling and the tissue behind the acoustic focus. In one embodiment, a method to display the information includes calculating a brightness variance across the top of the image. A significant brightness variance off of the dermis strongly suggests insufficient coupling whereas uniform brightness suggests uniform coupling across the majority of the therapy beam. A brightness variance calculation would be the second moment of the speckle brightness over a specific depth such as 1 mm to 2 mm from the acoustic window.

In one embodiment, a two-dimensional (2D) filtering function is used to reduce the brightness variation that naturally occurs from the speckle. In one embodiment, a quantitative or qualitative variable is presented to the user along with the high resolution image to suggest the quality of coupling at the acoustic window or tissue behind the focus.

In one embodiment, the coupling assessment image is combined with the high resolution image. For example, the two images could be multiplied together. This will provide one image to the operator without removing any of the information from the high resolution image. The 2D multiplication (pixel-by-pixel) will show the shadowing from poor coupling on top of the high resolution image. The operator can then decide whether treatment is appropriate based on the amount of brightness shadowing. In one embodiment, the two images are blended together like an overlay which permits greater emphasis on either the high resolution image or the coupling assessment image. In one embodiment, overlapping images can be configured in a manner like images presented to radiologists when combining registered images from different systems (e.g. MRI and ultrasound).

Multifocal Zone Sequencing

In various embodiments, ultrasound imaging is used with a therapeutic tissue treatment. According to various embodiments, an ultrasound treatment system creates one, two or more simultaneous therapeutic treatment points and/or focal zones under the skin surface for a cosmetic treatment. In one embodiment, a treatment comprises mechanical dithering in which the therapy transducer is moved locally around the intended center of the thermal coagulation point (TCP). The acoustic beam movement can be side-to-side, up-down, and/or angular. In one embodiment of mechanical dithering, the movement of the motion mechanism is sufficiently fast enough to create a flatter temperature profile around the intended TCP which either allows a reduction of total acoustic energy for the same effected tissue volume or the same total acoustic energy for a larger effected tissue volume or any combination thereof. In accordance with various embodiments, frequency modulation modifies the location of a focal zone and/or spacing between the focal zones, such that electronic dithering of beam via modulation of the frequency precisely alters and/or moves the position of the beam focus point(s). For example, in one embodiment, a spacing of 1.5 mm can be dithered with +/−0.1 mm using a small frequency swing. In various embodiments, any one or more spacings of 0.5, 0.75, 1.0, 1.2, 1.5, 2.0 mm can be dithered with +/−0.01, 0.05, 0.1, 0.12, 0.15, 0.20, 0.25, 0.30 mm using a frequency swing. In various embodiments, a frequency is modulated by 1-200% (e.g., 1%, 5%, 10%, 15%, 20%, 25%, 30%, 35%, 40%, 45%, 50%, 100%, 120%, 150%, 180%, 200% and any range therein).

Figure 23:
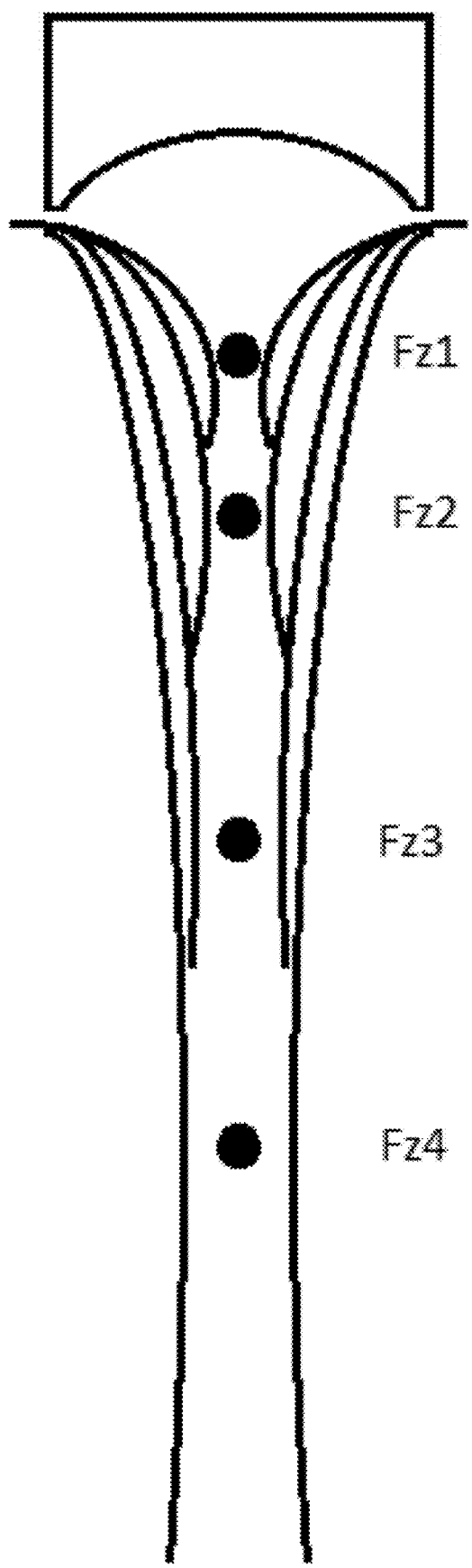
FIG. 23 is a schematic representation of an imaging diagnostic ultrasound system according to various embodiments of the present invention.

In various embodiments for improved ultrasound imaging, multiple focal zones are employed to obtain better signal quality and resolution through depth. For traditional, conventional diagnostic ultrasound scanners (linear, curvilinear, phased arrays, etc.), where the 2-D ultrasound images are formed without having to move the transducer, the sequence of acquiring these multiple focal zones are relatively inconsequential as precise placement of these focal zones can be controlled electronically. FIG. 23 illustrates a focal zone imaging that does not move while imaging, with electronically steered/translated aperture. For non-moving imaging transducers, focal zone positioning is precise, therefore focal zone sequencing is not employed. In traditional multiple focal zone imaging sequences, the order of the focal zone interrogation does vary. For example, a 4-focal zone sequence will follow the progression (f1, f2, f3, f4) independent of location and direction of motion.

However, for moving imaging transducers (e.g., mechanically translated or steered arrays), this becomes problematic, due to the positional differences of the transducer as it scans through the multiple focal zones. This positional mis-registration is particularly magnified when forming imaging bidirectionally (forming both left-to-right and right-to-left images), as the region of interrogation between the two images will be different. This principle is demonstrated in FIG. 24 in a linearly translating circumstance, but the disclosure applies to all types of motion, including but not limited to translational, rotational, and two-dimensional, or any combination thereof.

Figure 24:
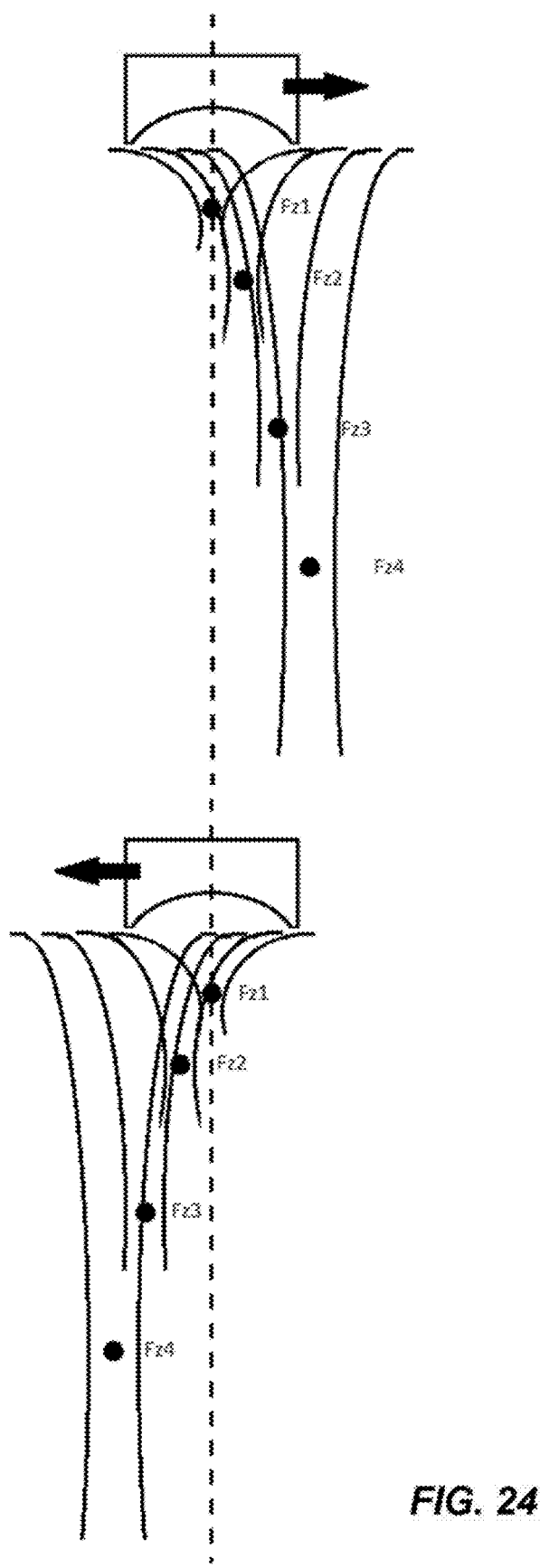
FIG. 24 is a schematic representation of bidirectional imaging at the same lateral location according to various embodiments of the present invention.

Embodiments of the imaging system disclosed herein address these misalignments. FIG. 24 illustrates bidirectional imaging at the same lateral location. In instances, spatial mis-registration occurs due to the fact that the transducer is moving while imaging. In particular, focal zone 4 (Fz4) can be seen to be farthest apart between the two images, although they should be interrogating the same region of interest. When forming a 2-D image with a mechanically translated/steered transducer, the transmit/receive position of the transducer will vary, due to the fact that during the propagation time associated with an ultrasound signal, the transducer has also moved.

Figure 25:
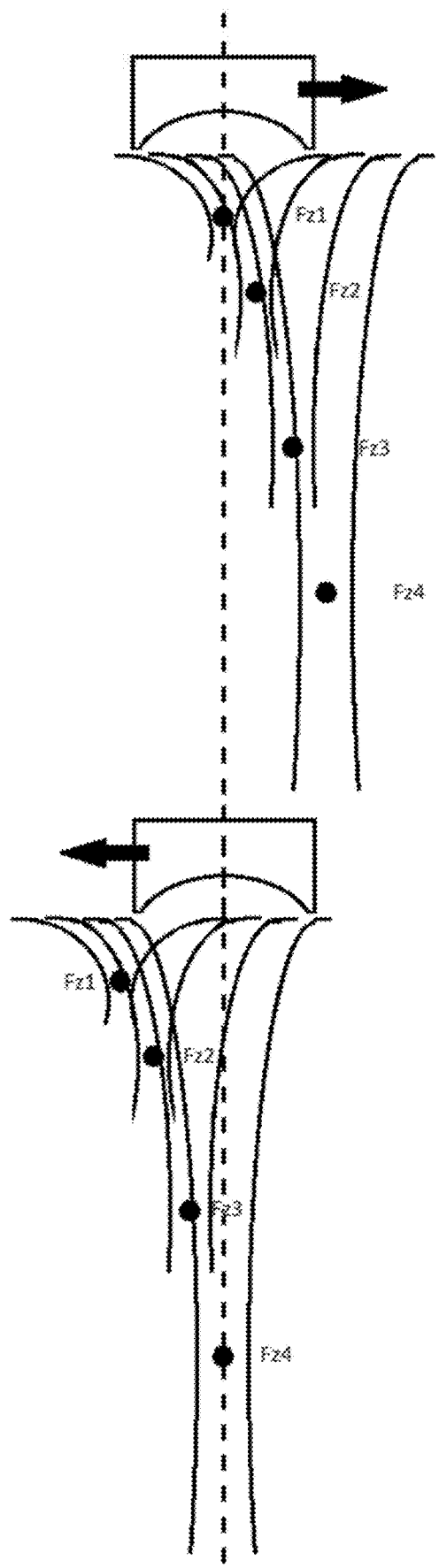
FIG. 25 is a schematic representation of directionally dependent focal zone sequencing according to various embodiments of the present invention.

In one embodiment, an alternative sequence is proposed such that the first direction-traveling (outbound) sequence shall proceed in order (f1, f2, f3, f4), but the second direction-traveling (returning) sequence is reversed (f4, f3, f2, f1), thereby allowing better registration of two images. In one embodiment, an alternative sequence is proposed such that the right-traveling (outbound) sequence shall proceed in order (f1, f2, f3, f4), but the left-traveling (returning) sequence is reversed (f4, f3, f2, f1), thereby allowing better registration of two images (FIG. 25). In various embodiments, a direction can be left, right, forward, backward, up, or down.

FIG. 25 illustrates an embodiment of directionally dependent focal zone sequencing. The left-traveling sequence is in reverse order relative to the right-traveling sequence. As a result, the focal zone alignment has been improved. Further, the positions of acquisitions can be staggered, such that the same regions of interest are better registered between these two images (FIG. 26).

Figure 26:
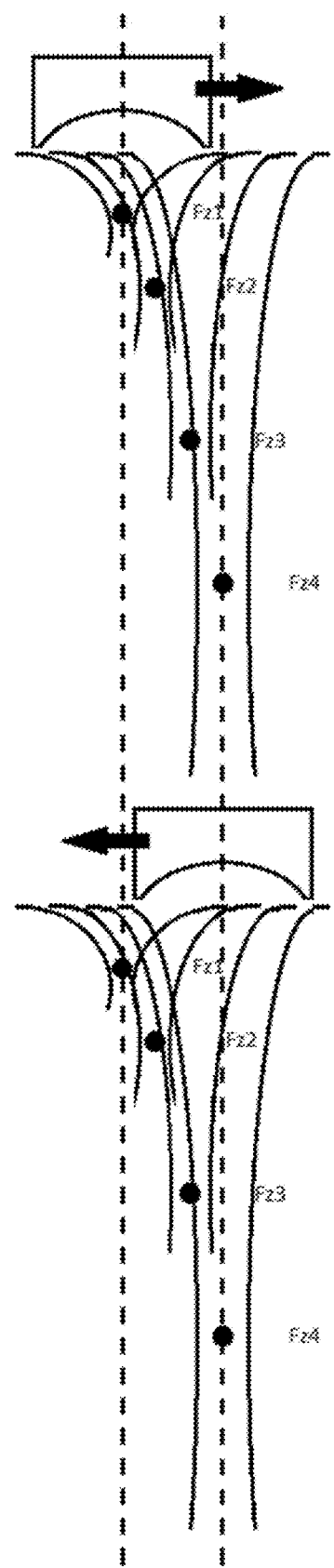
FIG. 26 is a schematic representation of directionally dependent focal zone sequencing with different triggering locations according to various embodiments of the present invention.

FIG. 26 illustrates an embodiment of a directionally dependent focal zone sequencing with different triggering locations. The spatial registration between right traveling and left traveling A-lines has been further improved by staggering the triggering locations.

In an embodiment, an imaging system employs a novel sequence of two consecutive A-lines following progression of (line 1: f1, f2, f3, f4; line2: f4, f3, f2, f1) continuously. This sequence can be repeated across the entire field of view, and assuming an even number of vectors within the field of view, the returning sequence can have the exact same alternating pattern focal zone sequence, and the two images would be registered (FIG. 27).

Figure 27:
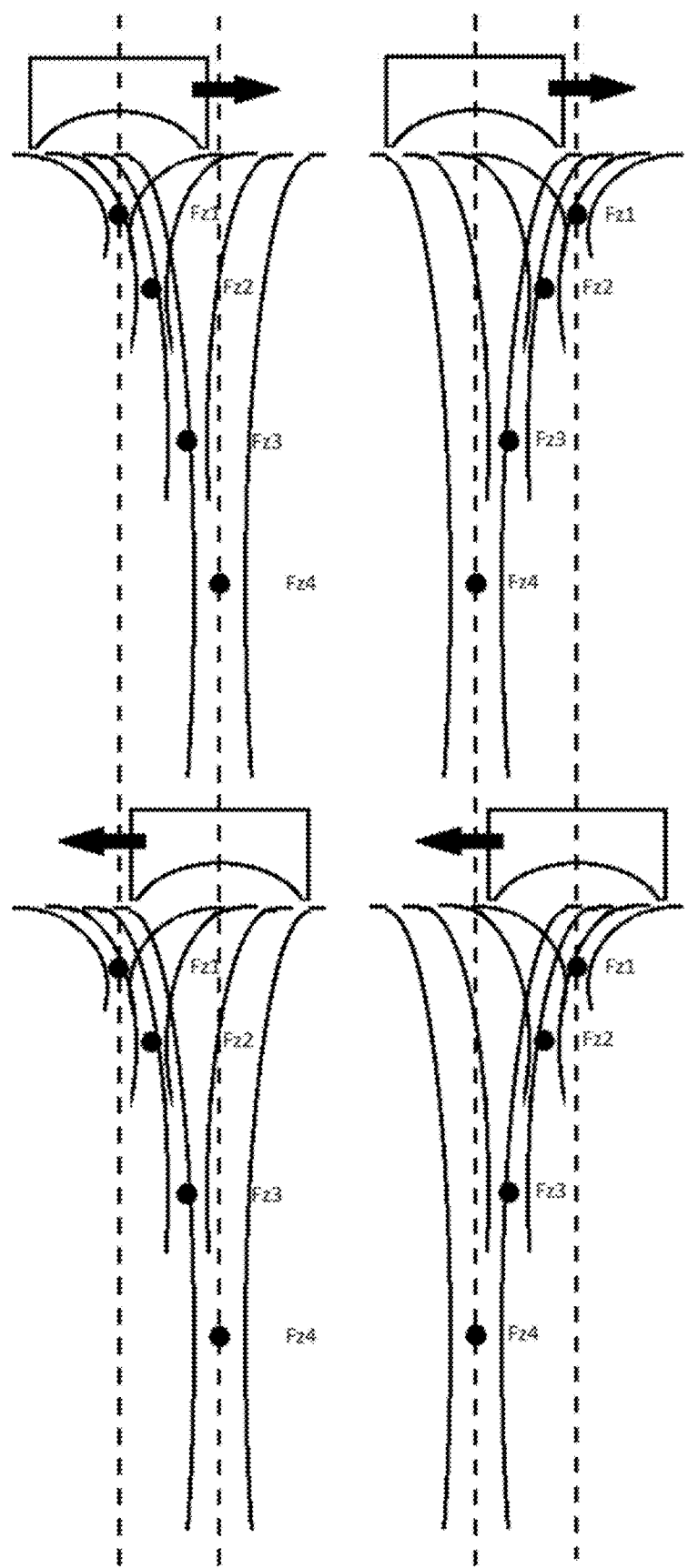
FIG. 27 is a schematic representation of directionally dependent focal zone sequencing with alternating between (f1-f2-f3-f4) & (f4-f3-f2-f1) on consecutive A-lines according to various embodiments of the present invention.

FIG. 27 illustrates an embodiment of a directionally dependent focal zone sequencing with alternating between (f1-f2-f3-f4) and (f4-f3-f2-f1) on consecutive A-lines. If the entire field of view is spanned by an even number of A-lines, then the left-traveling and right-traveling focal sequences are the same. Triggering locations still vary between the two images.

In various embodiments, the multifocal zone imaging provides advantages for better correlation between first direction-traveling and second direction-traveling formed images.

In various embodiments, the multifocal zone imaging provides advantages for improved effectiveness of B-mode imaging at faster (e.g., 2×, 3×, 4×) the scanning rate.

In various embodiments, multifocal zone imaging is applied to any number of focal zones greater than one. In various embodiments, the number of focal zones is two, three, four, five, six, seven, eight, nine, ten, or more.

Transducers

Figure 28:
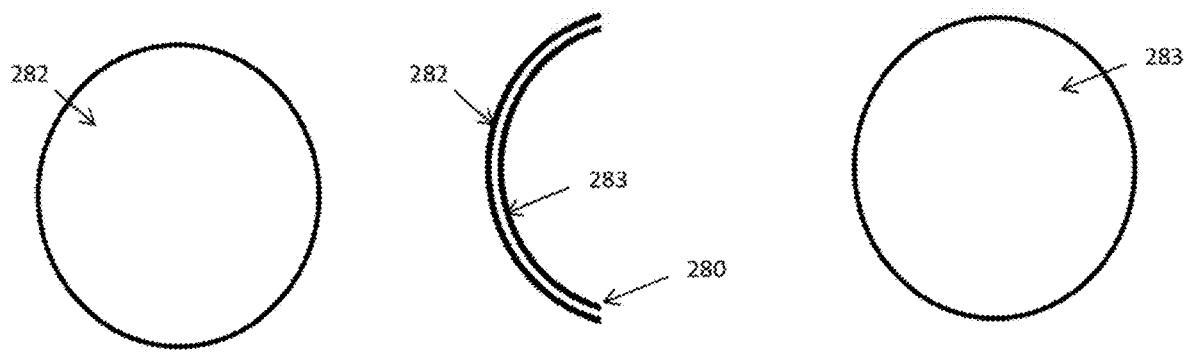
FIG. 28 is schematic views of a transducer as viewed from a convex side, side view cross section, and concave side various embodiments of the present invention.
Figure 29:
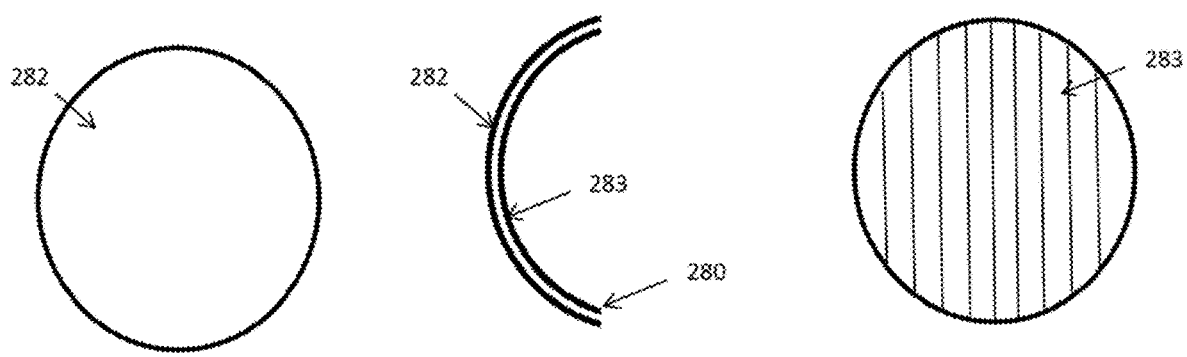
FIG. 29 is schematic views of a transducer as viewed from a convex side, side view cross section, and concave side various embodiments of the present invention.

In various embodiments, transducer 280 comprises a convex side 282 and a concave side 283. In various embodiments, a transducer 280 comprises a convex side 282 and a concave side 283 with features that provide for any one or more of variable depth, variable spacing, variable focus positioning, with one, two, three, four, or more simultaneous focus zones. FIG. 28 illustrates an embodiment of a transducer 280 comprising a single element with a convex side 282 and a concave side 283. FIG. 29 illustrates an embodiment of a transducer 280 comprising a solid, coated a convex side 282 and a striped a concave side 283, where the stripes comprise first poled and second poled regions, wherein a poled region is a positive, negative, or unpoled. FIG. 29 illustrates an embodiment of a transducer 280 comprising a solid, coated a convex side 282 and a striped a concave side 283, where the stripes comprise first regions and second regions, wherein a region can comprising a coating or no coating.

Figure 30:
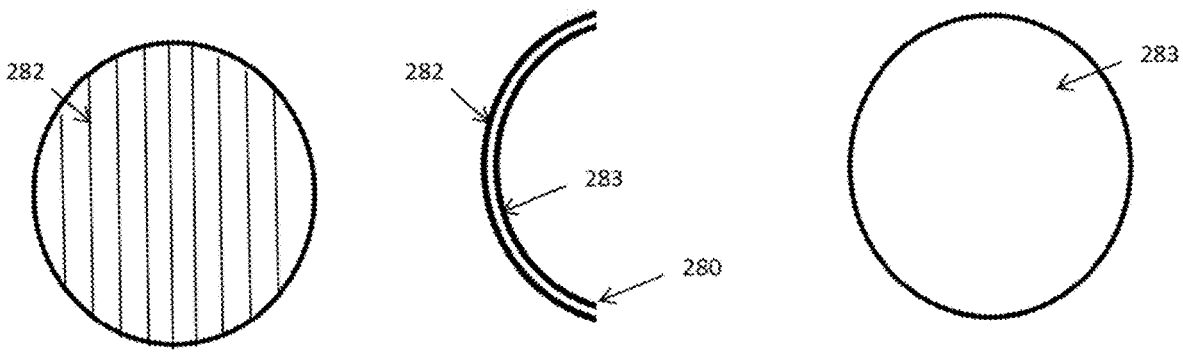
FIG. 30 is schematic views of a transducer as viewed from a convex side, side view cross section, and concave side various embodiments of the present invention.

FIG. 30 illustrates an embodiment of a transducer 280 comprising a striped convex side 282 and a solid, coated concave side 283, where the stripes comprise first poled and second poled regions, wherein a poled region is a positive, negative, or unpoled. FIG. 30 illustrates an embodiment of a transducer 280 comprising a striped convex side 282 and a solid, coated concave side 283, where the stripes comprise first regions and second regions, wherein a region can comprising a coating or no coating.

Figure 31:
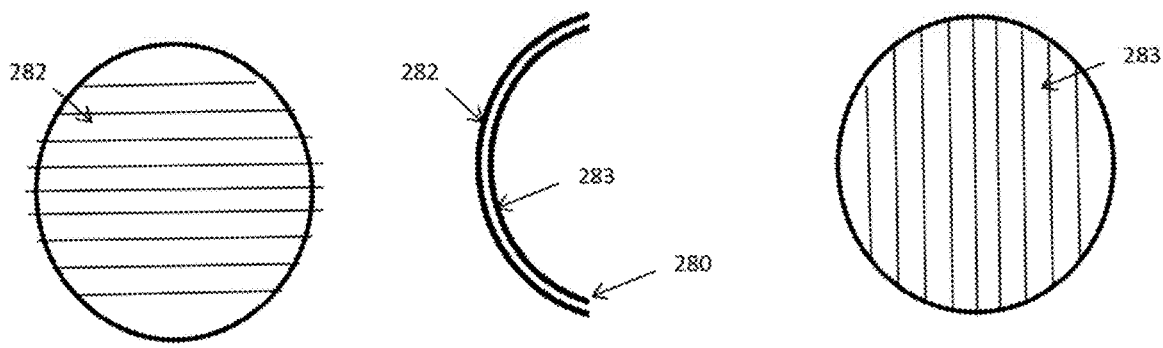
FIG. 31 is schematic views of a transducer as viewed from a convex side, side view cross section, and concave side various embodiments of the present invention.

FIG. 31 illustrates an embodiment of a transducer 280 comprising a striped convex side 282 and a striped concave side 283, where the stripes comprise first poled and second poled regions, wherein a poled region is a positive, negative, or unpoled, wherein the striped regions are rotated in an orientation of about 90 degrees with respect to each other. FIG. 31 illustrates an embodiment of a transducer 280 comprising a striped convex side 282 and a solid, coated concave side 283, where the stripes comprise first regions and second regions, wherein a region can comprising a coating or no coating, and wherein the stripes are rotated about 90 degrees with respect to each other.

Figure 32:
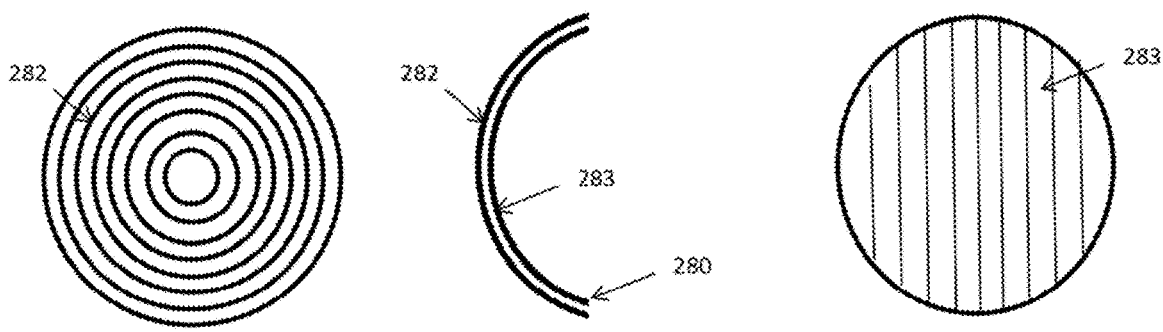
FIG. 32 is schematic views of a transducer as viewed from a convex side, side view cross section, and concave side various embodiments of the present invention.

FIG. 32 illustrates an embodiment of a transducer 280 comprising an annular convex side 282 and a striped concave side 283, where the stripes comprise first poled and second poled regions, wherein a poled region is a positive, negative, or unpoled. FIG. 32 illustrates an embodiment of a transducer 280 comprising an annular convex side 282 and a striped concave side 283, where the stripes comprise first regions and second regions, wherein a region can comprising a coating or no coating.

Figure 33:
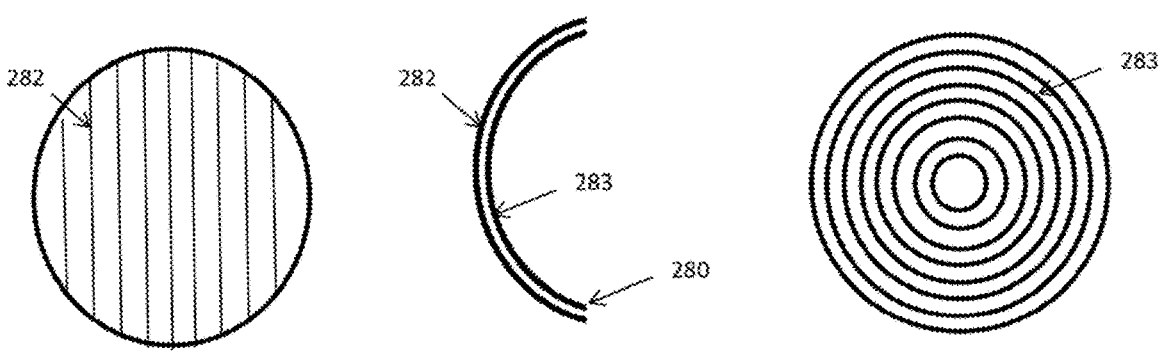
FIG. 33 is schematic views of a transducer as viewed from a convex side, side view cross section, and concave side various embodiments of the present invention.

FIG. 33 illustrates an embodiment of a transducer 280 comprising a striped convex side 282 and an annular concave side 283, where the stripes comprise first poled and second poled regions, wherein a poled region is a positive, negative, or unpoled. FIG. 33 illustrates an embodiment of a transducer 280 comprising a striped convex side 282 and an annular concave side 283, where the stripes comprise first regions and second regions, wherein a region can comprising a coating or no coating. In some embodiments, the system comprises various features that are present as single features (as opposed to multiple features). For example, in one embodiment, the system comprises, consists essentially of, or consists of a single ultrasound transduction element that is adapted to provide two simultaneous treatment zones via dithering. Multiple features or components are provided in alternate embodiments.

Some embodiments and the examples described herein are examples and not intended to be limiting in describing the full scope of compositions and methods of these invention. Equivalent changes, modifications and variations of some embodiments, materials, compositions and methods can be made within the scope of the present invention, with substantially similar results.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "coupling a transducer module with an ultrasonic probe" include "instructing the coupling of a transducer module with an ultrasonic probe." The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 25 mm" includes "25 mm."

What is claimed is:

1. An ultrasound treatment and imaging system configured for reducing imaging misalignment and further configured for applying precise ultrasonic therapy for lifting a brow, comprising:

an ultrasonic probe adapted for placement at a skin surface of a face at the brow, the ultrasonic probe comprising:

a hand wand and a removable transducer module, the removable transducer module configured for interchangeable coupling to the hand wand, the removable transducer module comprising an ultrasound therapy transducer, the ultrasound therapy transducer comprising a piezoelectrically active material, the piezoelectrically active material having a focal length, adapted to focus ultrasonic therapy to a tissue below the skin surface of the brow, the tissue comprising one or more of: a dermis, a hypodermis, a superficial muscular aponeurotic system ("SMAS"), and a muscle, wherein the ultrasound therapy transducer is configured to focus the ultrasonic therapy at a thermal coagulation point with an acoustic power in a range of 1 W to 100 W at a treatment frequency range selected from the group consisting of: 4 MHz, 7 MHz, and 10 MHz to thermally heat the tissue to cause coagulation to form a lesion at the thermal coagulation point, an ultrasound imaging transducer adapted for imaging the tissue at the brow, wherein the ultrasonic therapy is applied at the thermal coagulation point to form the lesion based on precise imaging alignment of the imaging of the tissue from the ultrasound imaging transducer to improve the effectiveness and safety of the ultrasonic therapy at the tissue at the brow comprising the one or more of: the dermis, the hypodermis, the SMAS, and the muscle;

wherein the ultrasound therapy transducer and ultrasound imaging transducer are co-housed imaging/therapy transducers in an imaging-and-treatment module; and a motion mechanism configured for moving the co-housed imaging/therapy transducers within the imaging-and-treatment module in a first direction and a second direction configured for forming a plurality of the thermal coagulation points at the tissue at the brow, wherein the plurality of thermal coagulation points forms a plurality of the lesions at the tissue at the brow with a treatment spacing in a range from 0.01 mm to 25 mm, wherein the co-housed imaging/therapy transducers within the imaging-and-treatment module are mechanically attached to the motion mechanism, wherein the first direction is linear, wherein the second direction is linear, wherein the first direction is parallel to the second direction, wherein the first direction is opposite the second direction, wherein the ultrasound imaging transducer images with a first focal zone sequence order $(f_1, \ldots, f_N)$ or $(f_N, \ldots, f_1)$, where N>1 when travelling in the first direction, wherein the ultrasound imaging transducer images with a second focal zone sequence order $(f_N, \ldots, f_1)$ or $(f_1, \ldots, f_N)$ when travelling in the second direction, wherein a spatial registration between the ultrasound imaging transducer images with the first focal zone sequence order $(f_1, \ldots, f_N)$ or $(f_N, \ldots, f_1)$ in the first direction and the ultrasound imaging transducer images with the second focal zone sequence order $(f_N, \ldots, f_1)$ or $(f_1, \ldots, f_N)$ in the second direction is improved by staggering a triggering location, wherein the spatial registration improved by staggering the triggering location provides a better correlation between the ultrasound imaging transducer images at the brow with the first focal zone sequence order $(f_1, \ldots, f_N)$ or $(f_N, \ldots, f_1)$ in the first direction and the ultrasound imaging transducer images with the second focal zone sequence order $(f_N, \ldots, f_1)$ or $(f_1, \ldots, f_N)$ in the second direction, wherein the staggering comprises triggering an image acquisition at the brow at the triggering location over a time period, wherein the imaging-and-treatment module employs a directionally dependent focal zone sequencing of $(f_1\text{-}\ldots\text{-}f_N)$ and $(f_1\text{-}\ldots\text{-}f_N)$ or alternating between $(f_1\text{-}\ldots\text{-}f_N)$ and $(f_N\text{-}\ldots\text{-}f_1)$ on consecutive A-lines; and a control module coupled to the ultrasonic probe configured for controlling the ultrasound therapy transducer for treatment at the tissue at the brow and the ultrasound imaging transducer for imaging the tissue at the brow.

2. The ultrasound treatment and imaging system of claim 1,
wherein the second direction is the reversed path of the first direction,
wherein the coagulation occurs at a treatment depth selected from the group consisting of: 4.5 mm, 3 mm, and 1.5 mm.

3. The ultrasound treatment and imaging system of claim 1, wherein the first direction of motion occurs in multiple dimensions and the second direction is the reversed path of the first direction.

4. The ultrasound treatment and imaging system of claim 1, wherein the ultrasound imaging transducer images with the first focal zone sequence order is specified as $(f_1, \ldots, f_N)$, where N>2.

5. The ultrasound treatment and imaging system of claim 1, wherein the ultrasound therapy transducer is configured for treatment of tissue at a first set of locations that is positioned within a first cosmetic treatment zone and a second set of locations that is positioned within a second cosmetic treatment zone, the first zone being different from the second zone.

6. The ultrasound treatment and imaging system of claim 1, wherein the ultrasound therapy transducer is adapted to apply the ultrasonic therapy using amplitude modulation whereby a plurality of portions of the ultrasound therapy transducer are adapted to emit ultrasonic therapy at a plurality of amplitudes of acoustic intensity, wherein a first amplitude is different than a second amplitude.

7. The ultrasound treatment and imaging system of claim 6, wherein at least one portion of the ultrasound therapy transducer is adapted to emit the ultrasonic therapy at two or more amplitudes of acoustic intensity, and wherein the amplitude of the ultrasonic therapy emitted by the at least one portion of the ultrasound therapy transducer varies over time.

8. The ultrasound treatment and imaging system of claim 6, wherein the plurality of portions of the ultrasound therapy transducer are adapted to create a plurality of corresponding piezoelectric material variations in response to an electric field applied to the ultrasound therapy transducer.

9. The ultrasound treatment and imaging system of claim 8, wherein the plurality of piezoelectric material variations comprise at least one of expansion of the piezoelectrically active material of the plurality of portions of the ultrasound therapy transducer and contraction of the piezoelectrically active material of the plurality of portions of the ultrasound therapy transducer.

10. The ultrasound treatment and imaging system of claim 1, wherein the ultrasound therapy transducer is adapted to apply the ultrasonic therapy via phase shifting whereby a plurality of portions of the ultrasound therapy transducer are adapted to emit the ultrasonic therapy at a plurality of phases of acoustic intensity, wherein a first phase is different than a second phase.

11. The ultrasound treatment and imaging system of claim 1, wherein the ultrasound therapy transducer is adapted to apply an ultrasonic therapy using amplitude modulation,
whereby a plurality of portions of the ultrasound therapy transducer are adapted to emit ultrasonic therapy at a plurality of amplitudes of acoustic intensity, wherein a first amplitude is different than a second amplitude; and
whereby the plurality of portions of the ultrasound therapy transducer are adapted to emit ultrasonic therapy at a plurality of phases of acoustic intensity, wherein a first phase is different than a second phase.

12. The ultrasound treatment and imaging system of claim 1, wherein the ultrasound imaging transducer images with the first focal zone sequence order is specified as $(f_1, \ldots, f_N)$, where N>3.

13. A method of reducing imaging misalignment in a bidirectionally moving ultrasound probe and performing precise ultrasonic therapy for lifting a brow, comprising:

placing an ultrasound probe at a skin surface of a face at the brow, the ultrasound probe comprising a hand wand and a removable transducer module, the removable transducer module configured for interchangeable coupling to the hand wand, the removable transducer module comprising an ultrasound therapy transducer and an ultrasound imaging transducer;

the ultrasound therapy transducer comprising a piezoelectrically active material, staggering a triggering location of a spatial registration between images from an ultrasound imaging transducer with a first focal zone sequence order ($f_1, \ldots, f_N$) or ($f_N, \ldots, f_1$) in a first direction and with a second focal zone sequence order ($f_N, \ldots, f_1$) or ($f_1, \ldots, f_N$) in a second direction with the ultrasound imaging transducer, wherein the staggering comprises triggering an image acquisition at the triggering location over a time period to improve the spatial registration by providing a better correlation between the ultrasound imaging transducer images with the first focal zone sequence order ($f_1, \ldots, f_N$) or ($f_N, \ldots, f_1$) in the first direction and the ultrasound imaging transducer images with the second focal zone sequence order ($f_N, \ldots, f_1$) or ($f_1, \ldots, f_N$) in the second direction, applying ultrasonic therapy to tissue below the skin surface at the brow, wherein the ultrasonic therapy is applied based on precise imaging alignment of the imaging of the tissue from the ultrasound imaging transducer to improve the effectiveness and safety of the ultrasonic therapy at the tissue below the skin surface at the brow, thereby thermally heating the tissue to cause coagulation at a thermal coagulation point to form a lesion by applying an acoustic power from the ultrasound therapy transducer in a range of 1 W to 100 W at a treatment frequency range selected from the group consisting of: 4 MHz, 7 MHz, and 10 MHz, wherein the ultrasound therapy transducer and ultrasound imaging transducer are co-housed imaging/therapy transducers, and a motion mechanism is configured for moving the co-housed imaging/therapy transducers in the first direction and the second direction, wherein the co-housed imaging/therapy transducers is mechanically attached to the motion mechanism, wherein the first direction is linear, wherein the second direction is linear, wherein the first direction is parallel to the second direction, wherein the first direction is opposite the second direction, wherein the ultrasound imaging transducer images with the first focal zone sequence order ($f_1, \ldots, f_N$) or ($f_N, \ldots, f_1$), with N>2, when travelling in the first direction, wherein the ultrasound imaging transducer images with the second focal zone sequence order ($f_N, \ldots, f_1$) or ($f_1, \ldots, f_N$) when travelling in the second direction, wherein the staggering comprises such that a region of interest is registered between the first focal zone sequence order ($f_1, \ldots, f_N$) or ($f_N, \ldots, f_1$) and the second focal zone sequence order ($f_N, \ldots, f_1$) or ($f_1, \ldots, f_N$).

14. The method of claim 13, wherein N=any one of the group consisting of: 3, 4, 5, 6, 7, 8, 9, and 10, wherein the coagulation occurs at a treatment depth selected from the group consisting of: 4.5 mm, 3 mm, and 1.5 mm.

15. The method of claim 13, wherein the ultrasound therapy transducer is adapted to apply ultrasonic therapy via phase shifting whereby a plurality of portions of the ultrasound therapy transducer are adapted to emit the ultrasonic therapy at a plurality of phases of acoustic intensity, wherein a first phase is different than a second phase.

16. An ultrasound module configured for reducing imaging misalignment and further configured for applying precise ultrasonic therapy for lifting a brow on a face, comprising:

an ultrasound therapy transducer adapted for placement at a skin surface on the face at the brow, the ultrasound therapy transducer being adapted to apply ultrasonic therapy to tissue below the brow, the tissue comprising one or more of: an epidermis, a dermis, a hypodermis, and a superficial muscular aponeurotic system ("SMAS"), wherein the ultrasound therapy transducer is configured to apply the ultrasonic therapy at an acoustic power in a range of 1 W to 100 W at a frequency range selected from the group consisting of: 4 MHz, 7 MHz, and 10 MHz to thermally heat the tissue below the brow to cause coagulation forming a lesion at a thermal coagulation point, wherein the ultrasonic therapy is applied based on precise imaging alignment of the imaging of the tissue from an ultrasound imaging transducer to improve the effectiveness and safety of the ultrasonic therapy at the tissue comprising the one or more of: the dermis, the hypodermis, the fascia, and the superficial muscular aponeurotic system;

the ultrasound imaging transducer adapted for imaging the tissue, wherein the ultrasound therapy transducer and ultrasound imaging transducer are co-housed imaging/therapy transducers in an imaging-and-treatment module; and a linear motion mechanism configured for moving the co-housed imaging/therapy transducers in a first linear direction and a second linear direction, wherein the co-housed imaging/therapy transducers are mechanically attached to the linear motion mechanism, wherein the linear motion mechanism forms a plurality of the thermal coagulation points, wherein the plurality of thermal coagulation points forms a plurality of the lesions with a treatment spacing in a range from 0.01 mm to 25 mm, wherein the first linear direction is opposite the second linear direction, wherein the ultrasound imaging transducer images with a first focal zone sequence order ($f_1, \ldots, f_N$) or ($f_N, \ldots, f_1$), where N>1 when travelling in the first linear direction, wherein the ultrasound imaging transducer images with a second focal zone sequence order ($f_N, \ldots, f_1$) or ($f_1, \ldots, f_N$) when travelling in the second linear direction, wherein a spatial registration between imaging in the first linear direction and the second linear direction is improved by staggering a triggering location such that a region of interest is registered between the first focal zone sequence order ($f_1, \ldots, f_N$) and the second focal zone sequence order ($f_N, \ldots, f_1$) or ($f_1, \ldots, f_N$), wherein the spatial registration improved by staggering the triggering location provides a better correlation between the ultrasound imaging transducer images with the first focal zone sequence order $(f_1, \ldots, f_N)$ or $(f_N, \ldots, f_1)$ in the first linear direction and the ultrasound imaging transducer images with the second focal zone sequence order $(f_N, \ldots, f_1)$ or $(f_1, f_N)$ in the second linear direction, wherein the staggering comprises triggering an image acquisition at the triggering location over a time period, wherein the ultrasound module employs a directionally dependent focal zone sequencing of $(f_1\text{-}\ldots\text{-}f_N)$ and $(f_1\text{-}\ldots\text{-}f_N)$ or alternating between $(f_1\text{-}\ldots\text{-}f_N)$ and $(f_N\text{-}\ldots\text{-}f_1)$ on consecutive A-lines.

17. The ultrasound module of claim 16, wherein the ultrasound therapy transducer is adapted to apply ultrasonic therapy using amplitude modulation whereby a plurality of portions of the ultrasound therapy transducer are adapted to emit ultrasonic therapy at a plurality of amplitudes of acoustic intensity, wherein a first amplitude is different than a second amplitude.

18. The ultrasound module of claim 16, wherein the ultrasound therapy transducer is adapted to apply ultrasonic therapy via phase shifting whereby a plurality of portions of the ultrasound therapy transducer are adapted to emit ultrasonic therapy at a plurality of phases of acoustic intensity, wherein a first phase is different than a second phase.

* * * * *